United States Patent
Henderson et al.

(10) Patent No.: US 8,182,511 B2
(45) Date of Patent: May 22, 2012

(54) CRANIOSPINAL FUSION METHOD AND APPARATUS

(75) Inventors: Fraser Cummins Henderson, Upper Marlboro, MD (US); John W. Newman, Newtown Square, PA (US)

(73) Assignee: Polaris Biotechnology, Inc., Newtown Square, PA (US)

( * ) Notice: Subject to any disclaimer, the term of this patent is extended or adjusted under 35 U.S.C. 154(b) by 192 days.

(21) Appl. No.: 12/688,848

(22) Filed: Jan. 15, 2010

(65) Prior Publication Data
US 2010/0179597 A1    Jul. 15, 2010

Related U.S. Application Data

(63) Continuation-in-part of application No. 12/350,936, filed on Jan. 8, 2009, which is a continuation-in-part of application No. 11/832,643, filed on Aug. 1, 2007, now Pat. No. 8,043,342, which is a continuation-in-part of application No. 11/832,646, filed on Aug. 1, 2007, now Pat. No. 8,083,743.

(60) Provisional application No. 61/019,622, filed on Jan. 8, 2008, provisional application No. 61/098,456, filed on Sep. 19, 2008, provisional application No. 61/104,862, filed on Oct. 13, 2008, provisional application No. 61/122,506, filed on Dec. 15, 2008, provisional application No. 61/138,031, filed on Dec. 16, 2008, provisional application No. 60/887,022, filed on Jan. 29, 2007.

(51) Int. Cl.
*A61B 17/70* (2006.01)

(52) U.S. Cl. ............ 606/246; 606/279; 623/17.19
(58) Field of Classification Search ............ 606/60, 606/71, 264, 279, 280, 246–249, 285, 151–157; 623/17.11–17.16, 17.19
See application file for complete search history.

(56) References Cited

U.S. PATENT DOCUMENTS

| | | | |
|---|---|---|---|
| 1,135,699 A | 4/1915 | Knauber |
| 1,739,009 A | 12/1929 | Lorber |
| 1,750,769 A | 3/1930 | Austin |
| 2,669,405 A | 2/1954 | Donnelly |
| 3,073,022 A | 1/1963 | Bush et al. |
| 4,456,005 A | 6/1984 | Lichty |

(Continued)

FOREIGN PATENT DOCUMENTS

DE    102004061280    6/2006

(Continued)

OTHER PUBLICATIONS

Naderi, Sait, et al., "Biomechanical Comparison of C1-C2 Posterior Fixations: Cable, Graft, and Screw Combinations", Spine, 1998; 23(18): 1946-1955.

(Continued)

*Primary Examiner* — Eduardo C Robert
*Assistant Examiner* — Christina Negrelli
(74) *Attorney, Agent, or Firm* — Knoble Yoshida & Dunleavy, LLC

(57) ABSTRACT

A spinal stabilization system that may be used to fix craniocervical junction. The system includes a cranial spinal attachment system that anchors one or more surgical instruments to a cranial surface using at least one cranial clamp and cranial fastener. The cranial spinal attachment system may be positioned along a perimeter of a cranial defect.

20 Claims, 35 Drawing Sheets

U.S. PATENT DOCUMENTS

| | | |
|---|---|---|
| 4,653,481 A | 3/1987 | Howland et al. |
| 4,655,199 A | 4/1987 | Steffee |
| 4,762,122 A | 8/1988 | Slocum |
| 4,790,702 A | 12/1988 | Maganias |
| 4,800,874 A | 1/1989 | David et al. |
| 4,805,602 A | 2/1989 | Puno et al. |
| 5,030,220 A | 7/1991 | Howland |
| 5,034,011 A | 7/1991 | Howland |
| 5,129,900 A | 7/1992 | Asher et al. |
| 5,133,716 A | 7/1992 | Plaza |
| 5,176,680 A | 1/1993 | Vignaud et al. |
| 5,269,784 A | 12/1993 | Mast |
| 5,360,429 A | 11/1994 | Jeanson et al. |
| 5,470,333 A | 11/1995 | Ray |
| 5,507,745 A | 4/1996 | Logroscino et al. |
| 5,545,164 A | 8/1996 | Howland |
| 5,545,228 A | 8/1996 | Kambin |
| 5,558,674 A | 9/1996 | Heggeness et al. |
| 5,611,354 A | 3/1997 | Alleyne |
| 5,643,261 A | 7/1997 | Schafer et al. |
| 5,653,710 A | 8/1997 | Harle |
| 5,733,285 A | 3/1998 | Errico et al. |
| 5,800,435 A | 9/1998 | Errico et al. |
| 5,968,047 A | 10/1999 | Reed |
| 6,039,738 A | 3/2000 | Sanders et al. |
| 6,056,753 A | 5/2000 | Jackson |
| 6,059,786 A | 5/2000 | Jackson |
| 6,080,579 A | 6/2000 | Hanley, Jr. et al. |
| 6,102,913 A | 8/2000 | Jackson |
| 6,125,526 A | 10/2000 | Wierzchon |
| 6,129,728 A | 10/2000 | Schumacher et al. |
| 6,129,730 A | 10/2000 | Bono et al. |
| 6,146,382 A | 11/2000 | Hurlbert |
| 6,179,841 B1 | 1/2001 | Jackson |
| 6,193,719 B1 | 2/2001 | Gournay et al. |
| 6,221,073 B1 | 4/2001 | Weiss et al. |
| 6,224,596 B1 | 5/2001 | Jackson |
| 6,238,396 B1 | 5/2001 | Lombardo |
| 6,319,254 B1 | 11/2001 | Giet et al. |
| 6,325,803 B1 | 12/2001 | Schumacher et al. |
| 6,355,043 B1 | 3/2002 | Adam |
| 6,423,067 B1 | 7/2002 | Eisermann |
| 6,454,768 B1 | 9/2002 | Jackson |
| 6,454,772 B1 | 9/2002 | Jackson |
| 6,520,990 B1 | 2/2003 | Ray |
| 6,524,315 B1 | 2/2003 | Selvitelli et al. |
| 6,547,790 B2 | 4/2003 | Harkey, III et al. |
| 6,565,566 B1 | 5/2003 | Wagner et al. |
| 6,623,486 B1 | 9/2003 | Weaver et al. |
| 6,726,687 B2 | 4/2004 | Jackson |
| 6,761,721 B2 | 7/2004 | Burgess et al. |
| 6,783,527 B2 | 8/2004 | Drewry et al. |
| 6,902,565 B2 | 6/2005 | Berger et al. |
| 6,928,900 B2 | 8/2005 | Dall et al. |
| 6,997,927 B2 | 2/2006 | Jackson |
| 7,018,379 B2 | 3/2006 | Drewry |
| 7,033,358 B2 | 4/2006 | Taylor et al. |
| 7,052,499 B2 | 5/2006 | Steger et al. |
| 7,083,621 B2 | 8/2006 | Shaolian et al. |
| 7,083,622 B2 | 8/2006 | Simonson |
| 7,131,303 B1 | 11/2006 | Champaigne |
| 7,213,999 B2 | 5/2007 | Haas |
| 7,235,079 B2 | 6/2007 | Jensen et al. |
| 7,250,052 B2 | 7/2007 | Landry et al. |
| 7,303,563 B2 | 12/2007 | Poyner et al. |
| 7,354,442 B2 | 4/2008 | Sasso et al. |
| 7,537,596 B2 | 5/2009 | Jensen |
| 7,575,588 B2 | 8/2009 | Barker et al. |
| 7,635,365 B2 | 12/2009 | Ellis et al. |
| 7,766,940 B2 | 8/2010 | Kwak et al. |
| 2001/0020168 A1 | 9/2001 | Hermann et al. |
| 2002/0120268 A1 | 8/2002 | Berger |
| 2003/0153913 A1 | 8/2003 | Altarac et al. |
| 2003/0176863 A1 | 9/2003 | Ueyama et al. |
| 2004/0030388 A1 | 2/2004 | Null et al. |
| 2004/0153070 A1 | 8/2004 | Barker et al. |
| 2005/0038438 A1 | 2/2005 | Anderson et al. |
| 2005/0080417 A1 | 4/2005 | Alexis et al. |
| 2005/0124994 A1 | 6/2005 | Berger et al. |
| 2005/0143737 A1 | 6/2005 | Pafford et al. |
| 2005/0159750 A1 | 7/2005 | Doherty |
| 2005/0216001 A1 | 9/2005 | David |
| 2005/0240185 A1* | 10/2005 | Boomer et al. ............ 606/69 |
| 2005/0283153 A1 | 12/2005 | Poyner et al. |
| 2005/0283248 A1 | 12/2005 | Gordon et al. |
| 2005/0288669 A1 | 12/2005 | Abdou |
| 2006/0004363 A1 | 1/2006 | Brockmeyer et al. |
| 2006/0058790 A1 | 3/2006 | Carl et al. |
| 2006/0079895 A1 | 4/2006 | McLeer |
| 2006/0173543 A1 | 8/2006 | Brau et al. |
| 2006/0217710 A1* | 9/2006 | Abdou ............ 606/54 |
| 2006/0224242 A1 | 10/2006 | Swords et al. |
| 2006/0264946 A1 | 11/2006 | Young |
| 2006/0264948 A1 | 11/2006 | Williams |
| 2006/0293660 A1 | 12/2006 | Lewis |
| 2007/0016189 A1 | 1/2007 | Lake et al. |
| 2007/0118121 A1 | 5/2007 | Purcell et al. |
| 2007/0219554 A1 | 9/2007 | Landry et al. |
| 2007/0270840 A1 | 11/2007 | Chin et al. |
| 2007/0299441 A1* | 12/2007 | Hoffman et al. ............ 606/61 |
| 2008/0039843 A1 | 2/2008 | Abdou |
| 2008/0045957 A1 | 2/2008 | Landry et al. |
| 2008/0051783 A1* | 2/2008 | Null et al. ............ 606/61 |
| 2008/0086124 A1 | 4/2008 | Forton et al. |
| 2008/0125781 A1* | 5/2008 | Hoffman et al. ............ 606/69 |
| 2008/0200953 A1 | 8/2008 | Reiley et al. |
| 2008/0234755 A1 | 9/2008 | Henderson, Sr. et al. |
| 2008/0234766 A1 | 9/2008 | Henderson, Sr. et al. |
| 2009/0018584 A1 | 1/2009 | Henderson, Sr. et al. |
| 2009/0036894 A1 | 2/2009 | Henderson, Sr. et al. |
| 2009/0177230 A1 | 7/2009 | Henderson, Sr. et al. |
| 2010/0010541 A1* | 1/2010 | Boomer et al. ............ 606/246 |
| 2010/0152575 A1 | 6/2010 | Henderson et al. |
| 2010/0222815 A1 | 9/2010 | Simonson |

FOREIGN PATENT DOCUMENTS

| | | |
|---|---|---|
| WO | 2004069038 | 8/2004 |
| WO | 2007005561 | 1/2007 |
| WO | 2007044716 | 4/2007 |
| WO | 2010002409 | 1/2010 |

OTHER PUBLICATIONS

Osterling, Julie, et al., "Early Recognition of Children with Autism: A Study of First Birthday Home Videotapes", J Autism Dev Disorders, 1994: 24(3): 247-257.

Pang, Dachling, et al., "Tethered cord syndrome in adults", J Neurosurg, 1982. 57(1): 32-47.

Piek, Jan P., et al., "Sensory-motor deficits in children with developmental coordination disorder, attention deficit hyperactivity disorder and autistic disorder", Hum Move Science, 2004. 23: 475-488.

Povlishock, John T., "Traumatically Induced Axonal Injury: Pathogenesis and Pathobiological Implications", Brain Pathology, 1992. 2(1): 1-12.

Povlishock, John T., et al., "The Pathobiology of Traumatically Induced Axonal Injury in Animals and Humans: A Review of Current Thoughts", J Neurotrama, 1995. 12(4): 555-564.

Rapin, Isabelle, "Appropriate investigations for clinical care versus research in children with autism", Brain & Develop, 1999. 21: 152-156.

Reich, D.S., et al., "Quantitative Characterization of the Corticospinal Tract at 3T", Am J Neuroradiol, 2006. 27: 2168-2178.

Resnick, Daniel K., et al., "Anatomic Suitability of the C1-C2 Complex for Pedicle Screw Fixation", Spine, 2002. 27 (14): 1494-1498.

Riggs, Jack E., et al., "Spastic Quadriparesis, Dysarthria, and Dysphagia following Cervical Hyperextension: A Traumatic Pontomedullary Syndrome", Military Medicine, 1995. 160(2): 94-95.

Rodier, Patricia M., "Converging evidence for brain stem injury on autism", Develop and Psychopath, 2002. 14: 537-557.

Rutter, Michael, et al., "Genetics and Child Psychiatry: II Empirical Research Findings", J Child Psychol Psychiatry, 1999. 40(1): 19-55.

Scahill, Lawrence, et al., "Children's Yale-Brown Obsessive Compulsive Scale: Reliability and Validity", J Am Acad Child Adol Psychiatry, 1997. 36(6): 844-852.

Scoville, W. B., et al., "The Cervical Ruptured Disc; Report of 115 Operative Cases", Trans Am Neurol Assoc, 1951. 56: 222-224.

Schneider, Richard C., et al., "The Syndrome of Acute Central Cervical Spinal Cord Injury", J Neurol Neurosurg Psychiatry, 1958. 21: 216-227.

Shuman, Sheri L., et al., "Apoptosis of Microglia and Ogliodendrocytes After Spinal Cord Contusion in Rats", J Neurosci Research, 1997. 50: 798-808.

Smith, C. G., "Changes in Length and Position of the Segments of the Spinal Cord with Changes in Posture in the Monkey", Radiology, 1956. 66(2): 259-265.

Stein, Mark A., et al., "Psychometric Properties of the Children's Atypical Development Scale", J Abnorm Child Psych, 1994. 22(2): 167-176.

Szatmari, Peter, "The Classification of Autism, Asperger's Syndrome, and Persuasive Developmental Disorder", Can J Psychiatry, 2000. 45(8): 731-738.

Szatmari, Peter, "The causes of autism spectrum disorders", BMJ, 2003. 326: 173-174.

Tachibana, Shigekuni, et al., "Spinal Cord Intramedullary Pressure. A Possible Factor in Syrinx Growth", Spine, 1994. 19(19): 2174-2179.

Tunturi, Archie R., "Elasticity of the spinal cord, pia, and denticulate ligament in the dog", J Neurosurg, 1978. 48: 975-979.

Wakefield, A J, et al., "Ileal-lymphoid-nodular hyperplasia, non-specific colitis, and pervasive developmental disorder in children", The Lancet, 1998. 351: 637-641.

Wing, Lorna, "Chapter 7—The Continuum of Autistic Characteristics", Diagnosis and Assessment in Autism, 1993. 91-110.

Wolf, John A., et al., "Traumatic Axonal Injury Induces Calcium Influx Modulated by Tetrodotoxin-Sensitive Sodium Channels", J Neurosci, 2001. 21(6): 1923-1930.

Zeegers, Mijke, et al., "Radiological findings in autistic and developmentally delayed children", Brain & Develop, 2006. 28: 495-499.

Corbett, J. J., et al., "'Sneeze syncope,' basilar invagination and Arnold-Chiari type 1 malformation", J Neurol, Neurosurg, and Psych, 1976; 39: 381-384.

Geddes, J. F., et al., "Neuropathology of inflicted head injury in children. II: Microscopic brain injury in infants", Brain, 2001: 124: 1299-1306.

Goel, Atul, "Treatment of basilar invaginations by atlantoaxial joint distraction and direct lateral mass fixation", J Neurosurg, 2004. 3: 281-286.

Goel, Atul, et al., "Craniovertebral Junction Realignment for the Treatment of Basilar Invagination With Syringomyelia: Preliminary Report of 12 Cases", Neurol Med Chir, 2005. 45: 512-518.

Grabb, Paul A., et al., "Ventral Brain Stem Compression in Pediatric and Young Adult Patients with Chiari 1 Malformations", Neurosurgery, 1999. 44(3): 520-528.

Kim, Louis J., et al., "Treatment of basilar invagination associated with Chiari 1 malformations in the pediatric population: cervical reduction and posterior occipitocervical fusion", J Neurosurg, 2004. 101: 189-195.

Levine, David N., "Pathogenesis of cervical spondylotic myelopathy", J Neurol, Neurosrug, and Psych, 1997. 62: 334-340.

Phillips, Douglas G., "Surgical treatment of myelopathy with cervical spondylosis", J Neurol, Neurosrug, and Psych, 1973. 36: 879-884.

Rossignol, Daniel A., et al., "The effects on hyperbaric oxygen therapy on oxidative stress, inflammation, and symptoms in children with autism: an open-label pilot study", BMC Pediatrics, 2007. 7: 36.

Ryken, Timothy C., et al., "Cervicomedullary compression in achondroplasia", J Neurosurg, 1994. 81: 43-48.

Stradling, J R, et al., "Changes in ventilation and its components in normal subjects during sleep", Thorax, 1985. 40: 364-370.

Tassanwipas, A, et al., "Magnetic resonance imaging study of the craniocervial junction", J Ortho Surg, 2005. 13(3): 228-231.

Grob, D., et al., "Posterior Occipitocervical Fusion a Preliminary Report of a New Technique," Spine, vol. 16, No. 3 Supplement, Jan. 1, 1991, pp. S17-S24.

Sandhu, Faheem A., MD, PhD, et al., "Occipitocervical Fusion for Rheumatoid Arthritis Using the Inside-Outside Stabilzation Technique," SPINE, 2003, pp. 414-419, vol. 28, No. 4.

Kumar, Raj et al., "Management of Pediatric Congenital Atlantoaxial Dislocation: A Report of 23 Cases from Northern India," Pediatric Neurosurgery, 2002, pp. 197-208, vol. 36.

Co-Pending U.S. Appl. No. 12/638,930, filed Dec. 15, 2009.

Aman, Michael G., et al., "The Aberrant Behavior Checklist: A Behavior Rating Scale for the Assessment of Treatment Effects", Am J Ment Defic, 1985: 89(5): 485-491.

Aman, Michael G., et al., "Psychometric Characteristics of the Aberrant Behavior Checklist", Am J Ment Defic, 1985: 89(5): 492-502.

Arundine, Mark, et al., "Vulnerability of Central Neurons to Secondary Insults after in Vitro Mechanical Stretch", J Neurosci, 2004. 24(37): 8106-8123.

Bain, Allison C., et al., "Tissue-Level Thresholds for Axonal Damage in an Experimental Model of Central Nervous System White Matter Injury", J Biomech Eng, 2000. 122: 615-622.

Bilston, Lynne E., et al., "The Mechanical Properties of the Human Cervical Spinal Cord In Vitro", Ann Biomed Eng, 1996. 24: 67-74.

Breig, A., "Overstretching of and Circumscribed Pathological Tension in the Spinal Cord—A Basic Cause of Symptoms in Cord Disorders", J Biomech, 1970. 3: 7-9.

Sawin, Paul D., et al., "Basilar invagination in osteogenesis imperfecta and related osteochondrodysplasias: medical and surgical management", J Neurosurg, 1997. 86: 950-960.

Brill, Charles B., et al., "Chiari I Malformation: Association With Seizures and Developmental Disabilities", J Child Neurog, 1997. 12(2): 101-106.

Brooks, Arthur L., et al., "Atlanto-axial arthrodesis by the wedge compression method", J Bone Joint Surg Am, 1978. 60(3): 279-284.

Bunge, Richard P., et al., "Observations on the Pathology of Human Spinal Cord Injury. A Review and Classification of 22 New Cases with Details from a Case of Chronic Cord Compression with Extensive Focal Demyelination", Adv Neurol, 1993. 59: 75-89.

Bunge, Richard P., et al., "Observations on the Pathology of Several Types of Human Spinal Cord Injury, with Emphasis on the Astrocyte Response to Penetrating Injuries", Adv Neurol, 1997. 72: 305-315.

Charman, Tony, et al., "Practitioner Review: Diagnosis of autism spectrum disorder in 2- and 3-year-old children", J Child Psychol Psychiatry, 2002. 43(3): 289-305.

Coyne, Terry J., et al., "C1-C2 Posterior Cervical Fusion: Long-term Evaluation of Results and Efficacy", Neurosurgery, 1995. 37(4): 688-693.

Crowe, Maria J., et al., "Apoptosis and delayed degeneration after spinal cord injury in rats and monkeys", Nat Med, 1997. 3(1): 73-76.

Cushing, K E, et al., "Tethering of the vertebral artery in the congenital arcuate foramen of the atlas vertebra: a possible cause of vertebral artery dissection in children", Dev Med Child Neurol, 2001. 43(7): 491-496.

Dickman, Curtis A., et al., "Posterior C1-C2 Transarticular Screw Fixation for Atlantoaxial Arthrodesis", Neurosurgery, 1998. 43(2): 275-280.

Dyste, Gregg N., et al., "Presentation and Management of Pediatric Chiari Malformations without Myelodysplasia", Neurosurgery, 1988. 23(5): 589-597.

Eleraky, Mohammed Aly, et al., "Posterior atlantoaxial facet screw fixation in rheumatoid arthritis", J Neurosurg, 1998. 89: 8-12.

Fein, Deborah, et al., "Clinical Correlates of Brainstem Dysfunction in Autistic Children", J Autism and Dev Disorders, 1981. 11(3): 303-315.

Fombonne, Eric, "The epidemiology of autism: a review", Psych Med, 1999. 29: 769-786.

Fombonne, Eric, "The Prevalence of Autism", JAMA, 2003. 289(1): 87-89.

Fombonne, Eric, et al., "MMR and autistic enterocolitis: consistent epidemiological failure to find an association", Mol Psychiatry, 2003. 8: 133-134.

Gaffney, Gary R., et al., "Morphological Evidence for Brainstem Involvement in Infantile Autism", Biol Psychiatry, 1988. 24: 578-586.

Galbraith, J. A., et al., "Mechanical and Electrical Responses of the Squid Giant Axon to Simple Elongation", J Biomech Eng, 1993. 115: 13-22.

Gallie, W. E., "Fractures and Dislocations of the Cervical Spine", Am J Surg, 1939. 46: 495-499.

Geddes, J. F., et al., "Traumatic axonal injury: practical issues for diagnosis in medicolegal cases", Neuorpath Appl Neurobio, 2000. 26: 105-116.

Grob, Dieter, et al., "Biomechanical Evaluation of Four Different Posterior Atlantoaxial Fixation Techniques", Spine, 1992. 17(5): 480-490.

Haid, Jr., Regis W., et al., "C1-C2 Transarticular Screw Fixation for Atlantoaxial Instability: A 6-year Experience", Neurosurgery, 2001. 49(1): 65-70.

Harms, Jurgen, et al., "Posterior C1-C2 Fusion With Polyaxial Screw and Rod Fixation", Spine, 2001. 26(22): 2467-2471.

Hasan, Mandi, et al., "Posterolateral tunnels and ponticuli in human atlas vertebrae", J Anat, 2001. 199(3): 339-343.

Henderson, Fraser C., et al., "Neuropathology of the brainstem and spinal cord in end stage rheumatoid arthritis: implications for treatment.", Ann Rheum Dis, 1993. 52(9): 629-637.

Henderson, Fraser C., et al., "Stretch-Associated Injury in Cervical Spondylotic Myelopathy: New Concept and Review", Neurosurgery, 2005. 56(5): 1101-1113.

Henriques, Thomas, et al., "Biomechanical Comparison of Five Different Atlantoaxial Posterior Fixation Techniques", Spine, 2000. 25(22): 2877-2883.

Holness, Renn O., et al., "Posterior Stabilization with an Interlaminar Clamp in Cervical Injuries: Technical Note and Review of the Long Term Experience with the Method", Neurosurgery, 1984. 14(3): 318-322.

Hong, Xia, et al., "Posterior Screw Placement on the Lateral Mass of Atlas: An Anatomic Study", Spine, 2004. 29(5): 500-503.

Howlin, Patricia, et al., "Diagnosis in Autism: A Survey of Over 1200 Patients in the UK", autism, 1997. 1(2): 135-162.

Ichihara, Kazuhiko, et al., "Gray Matter of the Bovine Cervical Spinal Cord is Mechanically More Rigid and Fragile than the White Matter", J Neurotrama, 2001. 18(3): 361-367.

Ichihara, Kazuhiko, et al., "Mechanism of the spinal cord injury and the cervical spondylotic myelopathy: new approach based on the mechanical features of the spinal cord white and gray matter", J Neurosurg: Spine, 2003. 99: 278-285.

Iwasaki, Motoki, et al., "Cervical Kyphosis: Predictive Factors for Progression of Kyphosis and Myelopathy", Spine, 2002. 27(13): 1419-1425.

Iwata, Akira, et al., "Traumatic Axonal Injury Induces Proteolytic Cleavage of the Voltage-Gated Sodium Channels Modulated by Tetrodotoxin and Protease Inhibitors", J Neuroscience, 2004. 24(19): 4605-4613.

Jafari, Saeed S., et al., "Axonal Cytoskeletal Changes After Nondisruptive Axonal Inury. II. Intermediate Sized Axons", J Neurotrama, 1998. 15(11): 955-966.

Johansson, Maria, et al., "Autistic spectrum disorders in Mobius sequence: a comprehensive study of 25 individuals", Dev Med Child Neurology, 2001. 43: 338-345.

Kitahara, Yukio, et al., "Effect of Spinal Cord Stretching due to Head Flexion on Intramedullary Pressure", Neurol Med Chir (Tokyo), 1995. 35: 285-288.

Kocak, Ayhan, et al., "A New Model for Tethered Cord Syndrome: A Biochemical, Electrophysiological, and Electron Microscopic Study", Pediatr Neurosurg, 1997. 26(3): 120-126.

Le Couteur, Ann, et al., "National Autism Plan for Children (NAPC)", National Initiative for Autism: Screening and Assessment (NIASA), 2003.

Lusardi, Theresa A., et al., "The separate roles of calcium and mechanical forces in mediating cell death in mechanically injured neurons", Biorheology, 2003. 40: 401-409.

Magerl, F., et al., "Stable Posterior Fusion of the Atlas and Axis by Transarticular Screw Fixation", Cervical Spine, 1987. 1: 322-327.

Maxwell, William L., et al., "Post-Acute Alterations in the Axonal Cytoskeleton after Traumatic Axonal Injury", J Neurotrama, 2003. 20(2): 151-168.

Menezes, Arnold H., et al., "Transoral-transpharyngeal approach to the anterior craniocervical junction. Ten-year experience with 72 patients.", J Neurosurg, 1988. 69: 895-903.

Milhorat, Thomas H., et al., "Chiari I Malformation Redefined: Clinical and Radiographic Findings for 364 Symptomatic Patients", Neurosurgery, 1999. 44(5): 1005-1017.

International Search Report and Written Opinion for International Application No. PCT/US2011/021351 dated Sep. 21, 2011.

Co-pending U.S. Appl. No. 13/163,650, filed Jun. 17, 2011.

* cited by examiner

FIG. 14
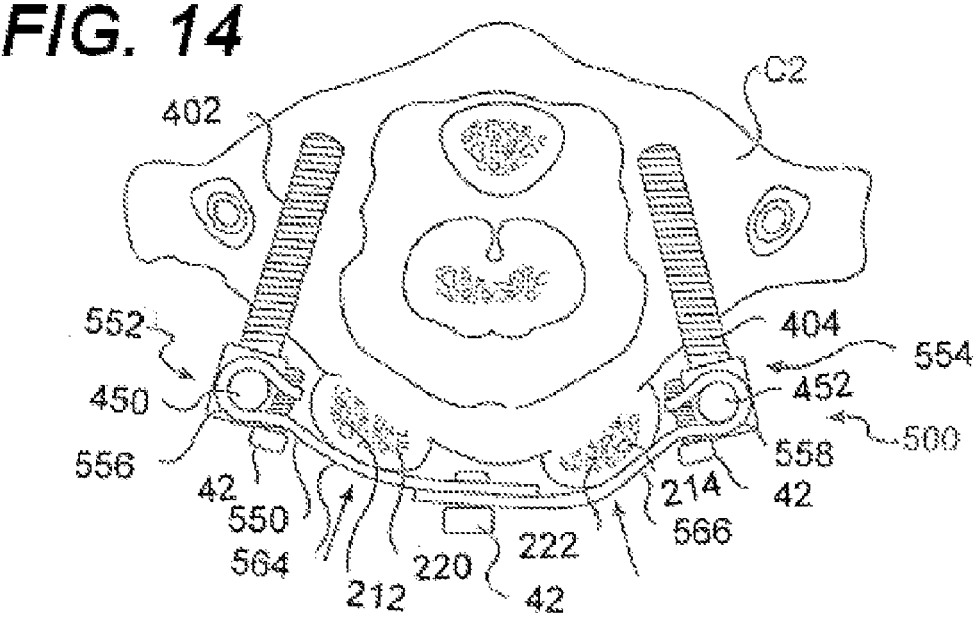
FIG. 15
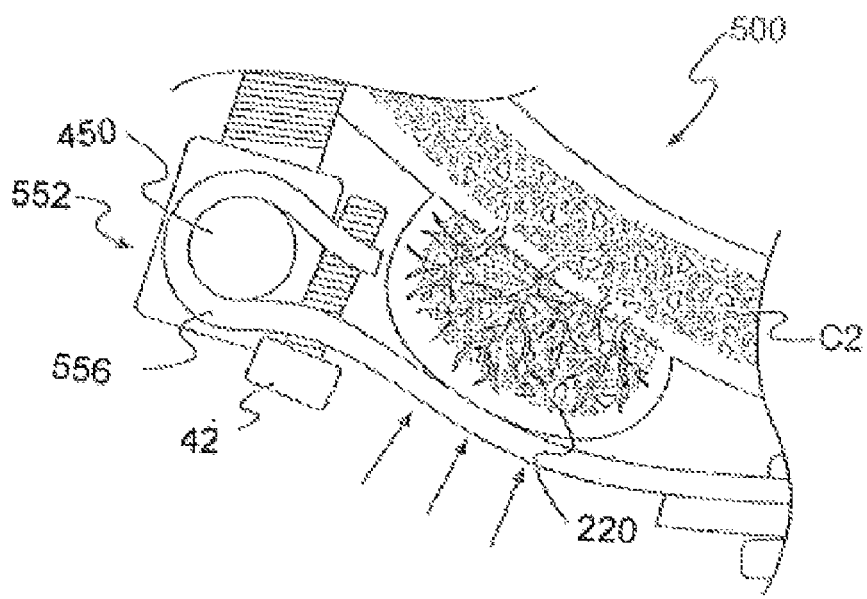
FIG. 16

CRANIOSPINAL FUSION METHOD AND APPARATUS

This application is a continuation in part of U.S. patent application Ser. No. 12/350,936, filed Jan. 8, 2009, which, in turn, claims benefit of priority to U.S. Provisional Patent Application No. 61/019,622, filed Jan. 8, 2008, U.S. Provisional Patent Application No. 61/098,456, filed Sep. 19, 2008, U.S. Provisional Patent Application No. 61/104,862, filed Oct. 13, 2008, U.S. Provisional Patent Application No. 61/122,506, filed Dec. 15, 2008 and U.S. Provisional Patent Application No. 61/138,031, filed Dec. 16, 2008; continuation in part of U.S. patent application Ser. No. 11/832,643, filed on Aug. 1, 2007, which in turn claims the benefit of U.S. Provisional Patent Application No. 60/887,022, filed on Jan. 29, 2007; continuation in part of U.S. patent application Ser. No. 11/832,646, filed on Aug. 1, 2007, which in turn claims the benefit of U.S. Provisional Patent Application No. 60/887,022, filed on Jan. 29, 2007; the entire disclosures of which are incorporated herein by reference.

BACKGROUND OF THE INVENTION

1. Field of the Invention

The present invention relates to a system and method for spinal fixation, stabilization and/or fusion of the human occipito-cervical junction. Additionally, the invention is further directed to an apparatus and method for the treatment of an abnormal neuraxial angle, abnormal clivo-axial angle and mitigation of neurological conditions underlying neurobehavioral disorders arising as a result of abnormalities of the neuraxial angle, clivo-axial angle, skull base, craniocervical, posterior fossa and combinations thereof, which, without wishing to be bound by theory in a subset of individuals, cause neuro-behavioral disorders such as autism, autism spectrum of disorders, bipolar disorder and other neurological disorders. The present invention is directed to the treatment of these neurological disorders through the recognition, diagnosis, and normalization of the craniospinal relationship by fixation, stabilization and/or fusion of the human occipito-cervical junction.

2. Description of the Related Technology

The normal range of motion of the craniospinal junction includes about 27° of flexion and extension, and 90° of lateral rotation; the craniospinal junction is thus the most mobile and articulating part of the human body. It is also the most active part of the human body in movement throughout the day, typically performing greater than 3 million motions a year. Because the craniospinal junction transmits the entire nervous structure to the body (with the exception of the vagus nerve), and is thus unfortunately susceptible to a host of degenerative disorders that can cause cranio-cervical instability. Common causes of cranio-cervical instability, include traumatic fractures, which account for approximately 3,000 fractures of the upper spine related to head trauma each year; congenital diseases, such as Ehlers Danlos syndrome, Down's syndrome, Morquio's syndrome and spondyloepiphyseal dysplasia syndrome, with a prevalence of at least 50,000; and osteogenesis imperfecta, with a prevalence of 7,000 patients. Additionally there are numerous causes of bone softening related to malabsorption syndromes and other renal/metabolic and endocrine syndromes that result in abnormal craniospinal relationships. Cancer and infections that involve the craniocervical junction can also cause destruction of the stabilizing elements.

Surgical intervention is often necessary to stabilize the craniocervical junction, restore neurologic function and prevent further neurologic deterioration. Hitherto, patients undergoing craniospinal stabilization have required an extensive surgical correction. Some patients undergo decompressive surgery from the front of the neck (transoral resection of the uppermost part of the spine), followed by fusion in the back of the neck and 3 months of stabilization in a halo brace, which encompasses the head (held by 4 screws in the skull) and the upper body. Other traditional fixation devices and methods are described in U.S. Pat. Nos. 5,030,220; 5,034,011; 5,545,164; 5,507,745; 6,547,790; 6,524,315 and 6,902,565 B2 as well as U.S. Published Patent Applications US2005/0288669 A1, US2005/0283153 A1 and US2005/0080417 A1.

These conventional fixation systems and methods, however, are not suitable for circumstances wherein problems arise due to poor bone quality or bone defects, such as an inadequate amount of bone to which a fixation system may be anchored. For example, approximately 70,000 suboccipital craniotomies have been preformed for Chiari malformation, of which about half require revision involving the reduction of the clivo-axial angle and fusion stabilization. Traditional fixation and cranial attachment devices are unsuitable in these circumstances in view of the limited amount of remaining bone, the width of the craniotomy defect or the thinness of the overlying scalp toward the midline. Furthermore the width and height of the cranial defect does not leave enough space to fasten a device below the transverse sinus of the calvarium. Therefore, there exists a need for an improved system and methodology that enables craniospinal stabilization in patients suffering from poor bone quality and bone defects.

SUMMARY OF THE INVENTION

Accordingly, it is an object of the invention to provide a cranial attachment device including: a clamp having a first member for engaging an upper surface of a cranial bone, wherein the first member includes a first hole; a second member for engaging a lower surface of the cranial bone, wherein the second member is spaced apart from and opposes said first member; and a third member for engaging an edge of the cranial bone, wherein the third member is connected to the first and second members; and a fastener including a second hole positioned through a width of the fastener, wherein the second hole is adapted to receive a spinal stabilization rod member, and wherein the fastener extends through the first hole and anchors the clamp to a cranial bone.

In an alternative embodiment, the invention is directed to a spinal stabilization system including: a rod member for use in spinal stabilization; a cranial attachment device having a clamp including a first member for engaging an upper surface of a cranial bone, wherein the first member has a first hole; a second member for engaging a lower surface of the cranial bone, wherein the second member is spaced apart from and opposes the first member; and a third member that engages an edge of the cranial bone, wherein the third member is connected to the first and second members and a fastener attached to the rod member and the clamp, wherein the fastener is inserted through the first hole and wherein the fastener anchors the clamp and the rod member to the cranial bone.

In yet another embodiment, the invention is directed to a method for using a spinal stabilization system including the steps of: attaching a clamp to a cranial bone, wherein the clamp includes a first member that contacts an upper surface of the said cranial bone and wherein the first member includes a first hole, a second member that contacts a lower surface of the cranial bone and a third member that contacts an edge of the cranial bone, wherein the third member is connected to said first and second members. The method further involves attaching the clamp to the cranial bone by inserting a fastener through the first hole and into the cranial bone and anchoring a first surgical instrument to the cranial bone by operatively associating the fastener to the first surgical instrument.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 14 is a cross-sectional view depicting certain components of the system that is shown in FIG. 1;

FIG. 15 is a fragmentary cross-sectional view depicting certain components of the portion of the system shown FIG. 1 that is depicted in FIG. 14;

FIG. 16 is a diagrammatical depiction of certain components of the portion of the system that is shown in FIG. 14;

FIG. 22(c) is a perspective view of the attachment system of FIG. 21(a) with an applied bone graft material;

FIG. 31(*b*) is a cross-section of an exemplary modular embodiment of the osteointegration apparatus with a plurality of independently movable segments;

FIG. 33(*b*) is a fragmentary perspective of the C1 vertebral attachment system engaging the osteointegration apparatus;

DETAILED DESCRIPTION OF THE PREFERRED EMBODIMENT(S)

Figure 1:
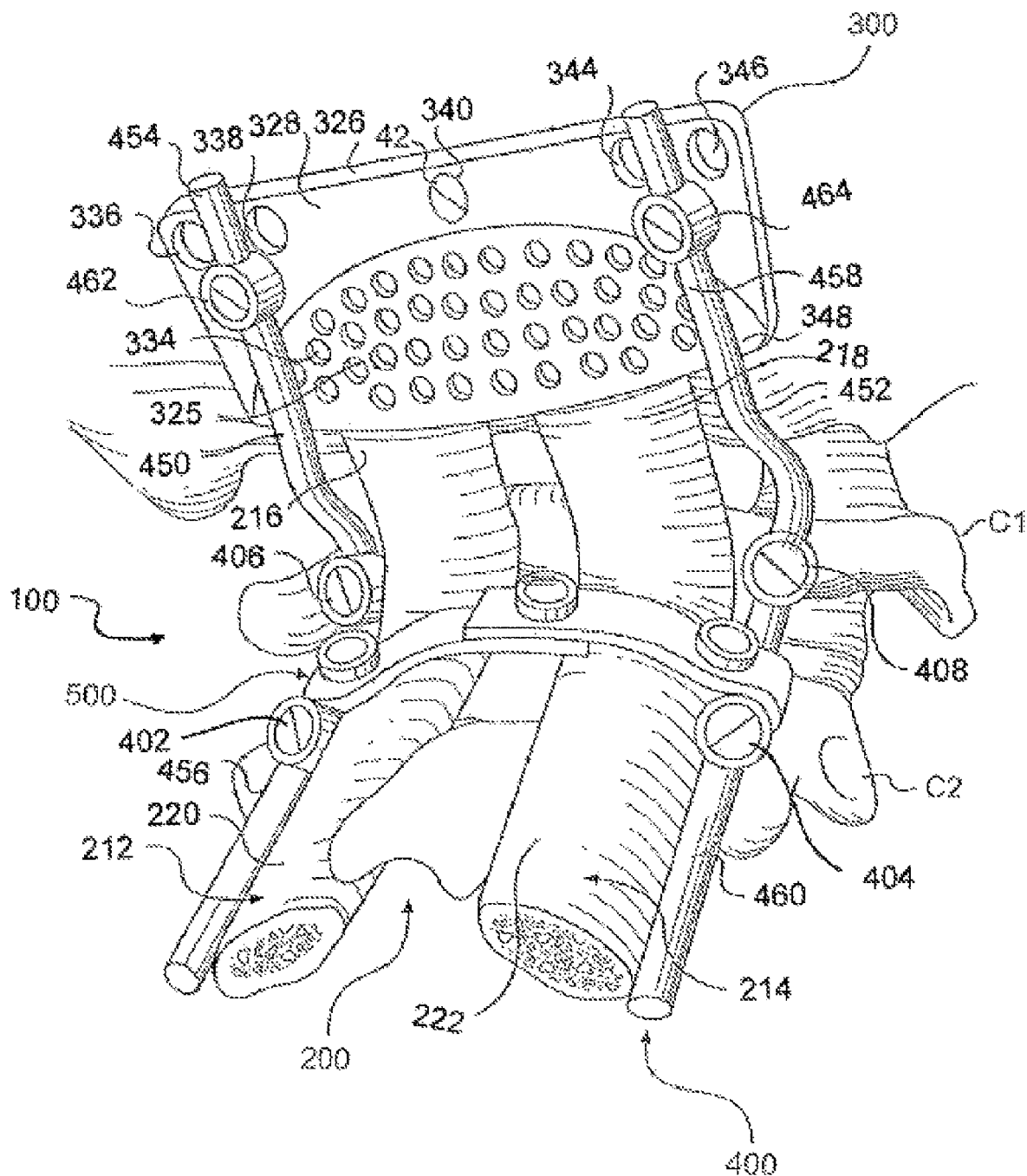
FIG. 1 is a fragmentary perspective view of a system for effecting fusion of the human occipitocervical junction according to an exemplary embodiment of the invention.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Thus, for example, reference to "a neurological disorder" may include a plurality of neurological disorders and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

For purposes of the present invention, "clivo-axial angle", as used herein refers to the angle between the dorsal aspect of the clivus and the dorsal aspect of the axis, i.e. C2 vertebra. Also known as the clivo-vertebral angle, clivus spinal angle, and clival canal angle, the clivo-axial angle is a surrogate measurement of the neuraxis and reflects the concomitant angulation of the neuraxis, i.e. curvature of the neuraxis, resulting from abnormalities of the craniocervical junction and a central component of the measurement of brainstem stress. A normal clivo-axial angle is approximately 165°±about 10° in the neutral position and about 145°±about 10° when fully flexed, reflects a normal relationship between the cranium and the spine, and therefore a normal alignment of the central nervous system, or the neuraxis, i.e. brainstem and spinal cord. This angle becomes more acute in the presence of platybasia, basilar invagination, retroflexed odontoid, and functional cranial settling. The presence of a relatively acute clivo-axial angle, for example an angle less than about 140°, results in deformative stresses within the neuraxis.

For purposes of the present invention, "neuraxial angle", as used herein refers to the angle between the medulla oblongata and upper spinal cord. The neuraxial angle and clivo-axial angle are directly related such that the neuraxial angle decreases as the clivo-axial angle decreases.

As referred to herein, "neurological disorder" refers to any neurological disease, neurological illness, neurological condition, neurological behavior, and/or any symptom related thereto. Additionally, as used herein, a method for "treating neurological disorders" refers to any method for preventing, reducing the incidence of, improving the condition of, improving a symptom associated with and/or, curing a neurological disorder or combinations thereof. Exemplary neurological disorders that may be treated using the method of the present invention may include but is not limited to: cortical motor function disorders, such as spasticity, paresis, clonus, and hyperreflexia; cortical sensory perception disorders, such as vestibular function disorders, balance and coordination disorders, dizziness, gait problems, dyslexia, clumsiness, development delay, audition discrimination and modulation disorders, delayed and mechanical speech disorders, vision problems, eye movement and coordination disorders, and sensory disturbance disorders; lower cranial nerve dysfunctions, such as lack of coordination between speech, swallowing and smooth articulation; bowel function disorders, such as gastro-esophageal sphincter control problems; abnormal urinary functioning, such as enuresis, bedwetting, and urinary bladder control disorders; psychological problems, such as anxiety, bipolar disorder, scizophrenia, and depression; respiratory dysfunctions, such as excessive snoring, obstructive or central apnea, and abnormal respiratory response to oxygen and carbon dioxide levels; sleep-disordered breathing, such as sleep apnea, muscular dysfunction, and sudden infant death; congenital diseases, such as Down's Syndrome, Ehlers Danlos Syndrome, Morquio's syndrome, spondyloepiphyseal dysplasia, achondroplasia, and osteogenesis; developmental disorders, such as Chiari Malformation, autism spectrum disorders, such as autism, Asperger Syndrome, and pervasive developmental disorder-not otherwise specified, and Attention Deficit Hyperactivity Disorder; anatomic conditions, such as platybasia, retroflexed odontoid, basilar invagination, and foramen magnum stenosis; acquired bone-softening conditions, such as Rickets, Paget's disease, and hyperparathyroidism; and metabolic bone disorders; connective tissue disorders; renal, metabolic, and endocrine syndromes. The invention may also be used to treat autonomic neural function disorders that cause abnormal blood flow to the skin, abnormal sexual response, GERDS, dyspraxia, idiopathic scoliosis, headaches, neck pain, back pain, head pain, encephalomyelopathy in the setting of trauma, neoplasm, positional orthostatic tachycardia, and bulbar findings.

As used herein, the term "spinal stabilization" may refer to any system or method for stabilizing the craniospinal junction and/or any other portion of the spine. In an exemplary embodiment, spinal stabilization may refer to any system or method for spinal and/or craniospinal alignment, spinal and/or craniospinal adjustment, correction of any spinal and/or craniospinal deformity or a combination thereof. An exemplary spinal stabilization system or method may involve fixation of the occipitocervical junction or fixation of one or more vertebra.

The present invention relates to a novel system and method for spinal stabilization. In an exemplary embodiment, the invention is directed to a system for stabilizing the craniospinal junction and a method for treating an abnormal neuraxial angle or clivo-axial angle as well as a wide variety of neurological disorders that may arise from the imposition of abnormal biomechanical stress and/or strain on the brainstem. The technology of the present invention may be predicated upon: reducing spinal deformities, particularly deformities at the craniospinal junction, which in an exemplary embodiment may be accomplished by correcting the relationship between the cranium and spine, and thereby normalizing the shape and geometry of the brainstem and spinal cord. This geometry may be described by the angulation between skull and spine (the clivo-axial angle), or the inherent angle between the medulla oblongata and spinal cord (the medullospinal angle). The present invention minimizes the invasive nature of the surgical procedure and provides sufficient surface area and milieu to render the surface conducive to fixation or osteointegration. This may be accomplished in part by increasing the available bone surface area for fixation and/or by applying a load to a bone graft. Furthermore, using novel surgical tools, such as a triple screw, posterior attachment devices, oblique trajectory instruments and trans-vertebral drills, the spinal stabilization system and method of the present invention may minimize surgical exposure and complications, resulting in a shorter surgery with fewer risks in comparison to conventional procedures. Consequently, the invention may decrease the risk of morbidity and the duration of a patient's hospital stay.

Referring now to the drawings, wherein like reference numerals designate corresponding structure throughout the various views, and referring in particular to FIG. 1, an exemplary embodiment of spinal stabilization system 100 of the present invention may include a bone scaffold system 200, a plate 300, a connection system 400 and a vertebral attachment system 500. In another embodiment, spinal stabilization system 100 may include a trans-vertebral stabilization system 600, osteointegration apparatus 700 and cranial attachment system 900. Spinal stabilization system 100 may be designed for a wide variety of applications and therefore include any combination of the aforementioned components. Spinal stabilization system 100 may be modular and/or modified for use in a wide variety of spinal stabilization applications. In an exemplary embodiment, it may be used to surgically fuse the occipito-cervical junction and/or treat a neurological disorder by minimizing or eliminating abnormal biomechanical stresses of the central nervous system and/or any deformities of the neuraxial angle.

Bone Scaffold System

Spinal stabilization system 100 may include a bone scaffold system 200 that may enhance fixation, osteointegration and/or load bearing capabilities of spinal stabilization system 100. This system may include one or more scaffold members 212, 214 that may facilitate fusion between spinal stabilization system 100 and biological tissue, such as a vertebra and/or cranium. Additionally, the scaffold members may further connect various components of spinal stabilization system 100 and/or multiple biological tissues.

Scaffold members 212, 214 may have any structural configuration and material composition to facilitate fixation, osteointegration and/or load bearing capability of one or more components of spinal stabilization system 100. In the exemplary embodiment of FIG. 1, bone scaffold system 200 may include one or more scaffold members 212, 214 that are at least partially porous and have a large surface area suitable for osteointegration. These scaffold members 212, 214 may be secured between any anatomical tissue, such as a vertebra or cranium, and one or more components of spinal stabilization system 100, such as plate 300, flange 325, connection system 400 and/or vertebral attachment system 500. The scaffold member 212, 214 may have a thickness that substantially spans the distance between a biological tissue and a surface of a spinal stabilization system 100 component such that the scaffold member 212, 214 may be tight secured therebetween. A component of spinal stabilization system 100 may apply a compressive force against the scaffold member 212, 214 such that the scaffold member is substantially positioned in continuous contact with or otherwise tightly held against an anatomical tissue. In an exemplary embodiment, the scaffold member 212, 214 may have a thickness of about 1 cm$^2$. The scaffold member 212, 214 may further have a length that spans one or more spinal vertebrae and/or spans the distance between the cranium and one or more spinal vertebrae.

A first scaffold member 212 and a second scaffold member 214 may facilitate the support, positioning and fixation of connection system 400 to portions of the spine and/or cranium. The first scaffold member 212 may have a first portion 220 that is positioned and biased against at least one portion of a vertebra so as to promote osteointegration and fusion therebetween. Similarly, the second scaffold member 14 may have a first portion 222 that is positioned and biased against at least one portion of a vertebra so as to promote osteointegration and fusion therebetween. First portions 220, 222 may be fused to any vertebrae. For purposes of spinal cranial fixation, in one embodiment, first portions 220, 222 may be fused to at least one portion of the cervical vertebra, preferably, a portion of the C1 vertebra and/or C2 vertebra. As shown in FIG. 1, the scaffold members cooperate with plate 300, flange 325 and vertebral attachment system 500 to enhance the fixation of connection system 400.

Scaffold members 212, 214 may further include one or more additional portions that enable fusion with other vertebrae and/or portions of the cranium to facilitate spinal stabilization. In an exemplary embodiment, scaffold member 212, 214 may include second portions 216, 218 that are positioned and biased against at least one portion of the cranium so as to promote cranial bone fusion and osteointegration.

Figure 2:
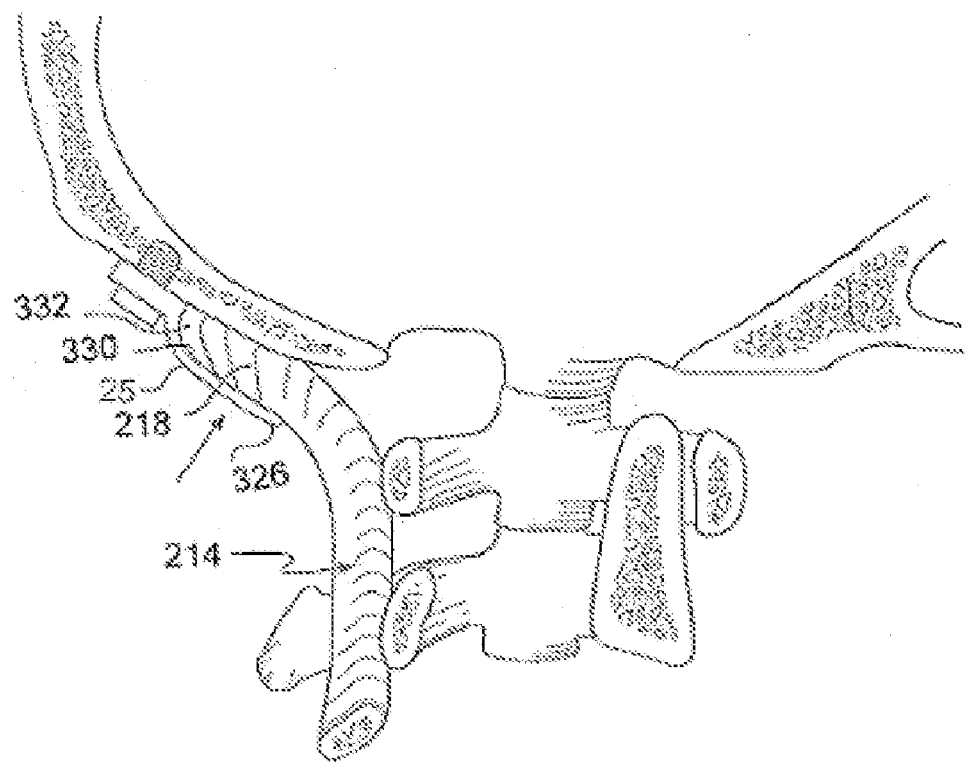
FIG. 2 is a fragmentary cross-sectional view of a portion of the system that is depicted in FIG. 1.

As is shown in FIG. 2, the second portion 218 of second scaffold member 214 is preferably positioned within the graft accommodation space 332 defined by the flange 325 so that the inner surface 330 of the plate 300 is biased to provide compressive pressure against second scaffold member 14. This compression will facilitate bone fusion between the second scaffold member 14 and the cranium. As shown in FIG. 1, the second portion 216 of the first scaffold member 212 is similarly positioned within the graft accommodation space 332 and impressively biased against the cranial bone to promote bone fusion. Plate 300 may be fabricated so as to include more than one graft accommodation space 332, so that each of the two scaffold members 212, 214 could be separately positioned within different spaces 332 defined by separate regions of the inner surface 330 of the plate 300.

Bone scaffold system 200 may be fabricated from any suitable biocompatible material that facilitates osteointegration, osteogenesis, fixation or a combination thereof. The scaffold members 212, 214 may be bone grafts that are harvested from another part of the patient's body, such as a rib, grafts from a cadaver, or a material that is constructed and arranged to facilitate the growth of bone. The invention is accordingly not limited to bone, but may use bone substitutes or non-osseous materials to accomplish long-term fixation of the cranium to the spine. For example, the scaffold members 212, 214 may be fabricated from a metallurgically bonded porous metal coating that is constructed and arranged to encompass and contain bone graft material, such as the material that is marketed under the trade name TRABECULAR METAL™ by Zimmer Inc. of Warsaw, Ind.

The scaffold members 212, 214 may alternatively be fabricated from a bone forming material such as a bone substitute having a collagen base and containing bone forming materials, or bone enhancing chemicals. Thus a bone forming material could be embodied as a fabricated mesh that functions as a bone conductor (that a form into which bone growth would occur, or as a bone-like medium such as coralline hydroxyapatite, which serves as an osteoconductor for blood vessel formation and subsequent deposition of bone, which could be injected or poured into the space between the bones to be fused.

Alternatively, the scaffold members may be fabricated from a metallic mesh-like substance that encourages or enables bone growth, such as tantalum mesh, which could be molded to fit into the space between the occiput and the spine, a bone allograft or a xenograft.

Plate

Spinal stabilization system 100 may include one or more plates 300 that facilitate spinal fixation, facilitate osteointegration and/or minimize wear and inflammation. Plate 300 may have any shape, size or configuration suitable for fixation to any bone structure. For example, plate 300 may be ovoid, rectangular, polyhedral or may have any shape comprising a composite of straight and curved edges. In an exemplary embodiment, plate 300 may be preformed to conform to a surface of one or more spinal, cranial or facial bones. Alternatively, plate 300 may be modular such that the shape of plate 300 may be manipulated to conform to a surface of a bone.

As shown in the exemplary embodiment of FIGS. 1-2, plate 300 may be a monolithic cranial plate sized and configured to enable secure fixation of the cranium to one or more vertebrae. The surface of plate 300 may be slightly curved to correspond to a surface of the cranium. In an exemplary embodiment, plate 300 may be further configured to define a space 332 for accommodating one or more osteogenic materials, particularly bone scaffold system 200. As shown in FIG. 2, space 332 may be at least partially positioned between plate 300 and the cranium. As best shown in FIGS. 1-2, plate 300 may include one or more edges 326, an outer surface 328 and an inner surface 330. Edge 326 may be curved and plate 300 may have a low profile so as to have no substantially sharp edges or protuberances in order to minimize wear, inflammation and stresses fractures. In an exemplary embodiment, edge 326 may have thickness of about 1 mm to about 1 cm. Additionally, plate 300 may vary in thickness along various regions of its body. For example, at least portion of edge 326 may be about 1 mm while the central portion of plate 300 may gradually increase in thickness to about 15 mm. Plate 300 may further include a plurality of perforations 334 to facilitate the growth of blood vessels within the newly formed bone tissue. Perforations 334 may be uniform or may vary in size and shape. These perforations 334 may be positioned in one or more regions or throughout the entire body of plate 300. In an exemplary embodiment, perforations 334 may have a diameter of at least 400 microns. A portion 348 of the outer surface 328 of the plate 300 may be grooved in order to accommodate instrumentation, as will be described in greater detail below.

Plate 300 may be composed from any biocompatible material having the material and mechanical properties suitable for bone fixation and load bearing applications. The material may be non-porous, porous or include porous and non-porous regions. In an exemplary embodiment, plate 300 may be at least partially porous and may be constructed and arranged to encompass and contain bone graft material, such as TRABECULAR METAL™. Additionally, plate 300 may be composed of a biocompatible material that is either chemically inert or may induce osteointegration. Exemplary materials may be metals, metal alloys, ceramics, polymers, such as a polymer from the polyaryl ether ketone family (PAEK), such as poyetheretherketones (PEEK) or polyether ketone ketone (PEKK), bio-absorbable compounds, bone, bone substitutes or a combination thereof. Preferably, the material may include a metal alloy, such as stainless steel and/or titanium. In an exemplary embodiment, one or more regions of plate 300, such as inner surface 330 and outer surface 328, may be composed of and/or coated with the same or different materials. In an exemplary embodiment, inner surface 330 may be composed of and/or coated with a material that promotes bone fusion, such as any conventional bone growth promoting substances. Optionally, the surface of plate 300 may be treated to adjust its frictional, wear or biocompatibility properties. In one embodiment, at least one portion of plate 300 may be coated with a material, shaped and/or textured to limit a range of motion of plate 300 relative to a cranial surface and/or one or more components of cranial stabilization system 900. At least one surface of plate 300 may be optionally coated with a material capable of enhancing, accelerating and/or promoting osteogenesis and/or promote bone fusion. In an exemplary embodiment, plate 300 may optionally have a metallurgically bonded porous metal coating, such as osteointegration apparatus 700.

Plate 300 may further include one or more flanges 325 that may be integrally formed with or subsequently attached to plate 300 to facilitate fixation and/or osteointegration. Flange 325 may also function to incorporate, enclose or provide a fulcrum in which a bone scaffold system 200, bone graft materials or bone substitutes may be held for the purpose of achieving a bone union or other permanent rigid or non-rigid attachment between the cranium and the spine. By entrapping the bone forming substances or other structural members in close union with the underlying cranium, flange 325 may facilitate morphogenesis through application of load; that is, through pressure and stabilization of the bone forming substances to enhance the milieu favoring new bone formation. In an exemplary embodiment, flange 325 may serve to provide a non-osseous or osseous union between the cranium and spine. Thus flange 325 thus may have both a physiological function and a mechanical function.

While an exemplary embodiment of flange 325 may have curved surfaces and edges as well as an unobtrusive low profile that conforms to an anatomic contour flange 325 may have any suitable shape, size, configuration or material composition that would facilitate fixation and/or osteointegration. Exemplary flanges 325 may be ovoid, rectangular, cubical, box-like or polyhedral in shape. In one embodiment, flange 325 may be curved and constructed to have a low profile suitable for being positioned over the cranium of an asthenic child where the thickness of skin and muscle contraindicate thickness of construct. In another exemplary embodiment, flange 325 may be a larger box-like adaptation for adolescences or adults, designed to facilitate the incorporation of rectangular, synthetic bone-forming substances or other non-osseous compounds. It is thus envisioned that flange 325 may have a plurality of configurations suitable for a wide variety of applications and may conform to different anatomical morphologies.

Flange 325 may be a preformed structure having a shape that corresponds to a bone surface. Alternatively, flange 325 may be a modular structure capable of being mechanically altered in shape to conform to an anatomical surface and/or compress or retain a bone graft material. Furthermore, flange 325 may have a non-porous structure, include one or more porous regions or may be an entirely porous structure with a plurality of perforation 334 to facilitate osteointegration. The perforations 334 may be uniform or different in size and/or shape so as to create a mesh-like construction that allows in-growth of bodily tissue or blood vessels. In one embodiment, flange 325 may have both porous and non-porous regions, wherein the porous region may be about more than 15% of the area of plate 300.

As shown in FIG. 1, flange 325 may be positioned adjacent to an edge 326 and/or centrally positioned in plate 300. Additionally, flange 325 may be partially or completely surrounded by or incorporated within plate 300 so as to create a substantially continuous and low profile structure. In an exemplary embodiment, flange 325 may have a thickness of about 0.5 to about 5 mm thickness.

In one embodiment, flange 325 and/or plate 300 may partially or completely cover a cranial defect, such as a hole in the cranium caused by trauma, disease or craniotomy, wherein screws may be placed in flange 325 and/or plate 300 rostral to the cranial defect. In an alternative embodiment, screws may be placed along a perimeter of the cranial defect as well as a perimeter of flange 325 and/or plate 300. For example, flange 325 and/or plate 300 may be configured to substantially span the width of the occiput, wherein the screws may be placed on either side of flange 325 and/or plate 300 and allow screw purchase on either side of the occiput to accommodate the situation where a central part of the occiput has been removed, for example, as a result of an occipital craniotomy.

Flange 325 may also at least partially define a boundary of space 332, as shown in FIG. 2. In an exemplary embodiment, flange 325 may have an elevated contour that arises from a caudal edge 326 of plate 300 away from the cranium so that space 332 forms a tunnel with one or more open ends. Flange 325 may arise from any portion of plate 300, including a lower, a central, an upper and/or a side region of plate 300. In an exemplary embodiment, flange 325 may rise from a region of plate 300 in direct contact with the cranial bone for a distance that is more than about 5 mm. The elevation of flange 325 exposes the underlying cranial bone surface, making this surface available for fusion to the overlying bone graft. The elevation may be sized to allow placement of a bone scaffold system 200 or a sufficient amount of bone graft materials or bone substitutes adequate to provide stability for growth. As shown in FIG. 2, the inner surface of flange 325 is substantially parallel to and spaced apart from the cranium, defining a graft accommodation space between the inner flange surface and the cranium when the plate 300 has been secured to the cranium. It is envisioned that malleable, or woven-bone forming substrates could be used to promote fusion, or provide the scaffolding itself for fusion. Conversely, other materials could be used beneath the flange 325 to provide non-osseous, non-rigid fixation.

The flange 325 may be constructed from any suitable material to facilitate fixation or osteointegration. In one embodiment, flange 325 may be composed of the same material as a portion of plate 300. Alternatively, flange 325 may be composed of a different material than plate 300. Plate 300 and/or flange 325 may include one or more apertures 336, 338, 340, 344, 346 that receive fastener 42 to enable fixation of plate 300 and/or flange 325 to a bone and/or one or more fastener assemblies 462, 464 to connect plate 300 and/or flange 325 with one or more components of spinal stabilization system 100, such as support rods 450, 452. A plurality of apertures 336, 338, 340, 344, 346, 372 may be arranged in any formation, such as clusters, arcs or lines, contiguously oriented, positioned in disparate locations, randomly positioned, uniformly positioned, overlying one another or a combination thereof. In one embodiment, one or more of these apertures 336, 338, 340, 344, 346, 372 may be placed around an edge or perimeter of the flange 325 and/or plate 300. The apertures 336, 338, 340, 344, 346, 372 may also be positioned on a flat or curved surface of plate 300. Additionally, these apertures may be reinforced with extra thickness to secure attachment and may further be threaded, partially threaded or free from threads. In one embodiment, two or more apertures may have a different size, shape or dimension designed to engage with different fasteners 42, which may be any device that enables fixation, such as a threaded component, hook, latch, pin, nail, wire, tether, or combinations thereof. Exemplary fasteners 42 may include a screw, rivet, bolt, triple screw 70 or combination thereof.

In an exemplary embodiment, one or more centrally positioned apertures 340, when coupled with fastener 42, will serve to anchor plate 300 and/or flange 325 to the cranium. A central aperture 340 may lie approximately in the midline of the patient's body and cranium in order to permit placement of fastener 42 into the thickest part of the skull, which usually runs from the inion to the opisthion. Centrally positioned apertures 340 may be threaded, partially threaded or not threaded. On each side of the midline, additional apertures 336, 338, 344, 346, 372 which may also be treaded, partially threaded or not threaded, can be positioned to receive fastener 42.

When coupled to centrally positioned aperture 340, fastener 42 may provide a primary attachment of plate 300 and/or flange 325 or to the skull. In this embodiment, fastener 42 may be a robust, cortically threaded screw of variable length, preferably having a month within a range of about 7 mm to about 12 mm. The screw preferably has a thickness within a range of about 2 mm to about 10 mm, with a blunted end. It may have an optional spiral lock feature that locks the screw into plate 300 and/or flange 325. The screw may also be optionally lagged to provide increased loading pressure on plate 300 and/or flange 325. In an exemplary embodiment, the screw may be made of titanium alloy, of bone, or of a bone forming or bone compatible substance. For example, a ceramic, or hydroxyl-apatite composite or metal alloy/bone composite could be used.

Figure 3:
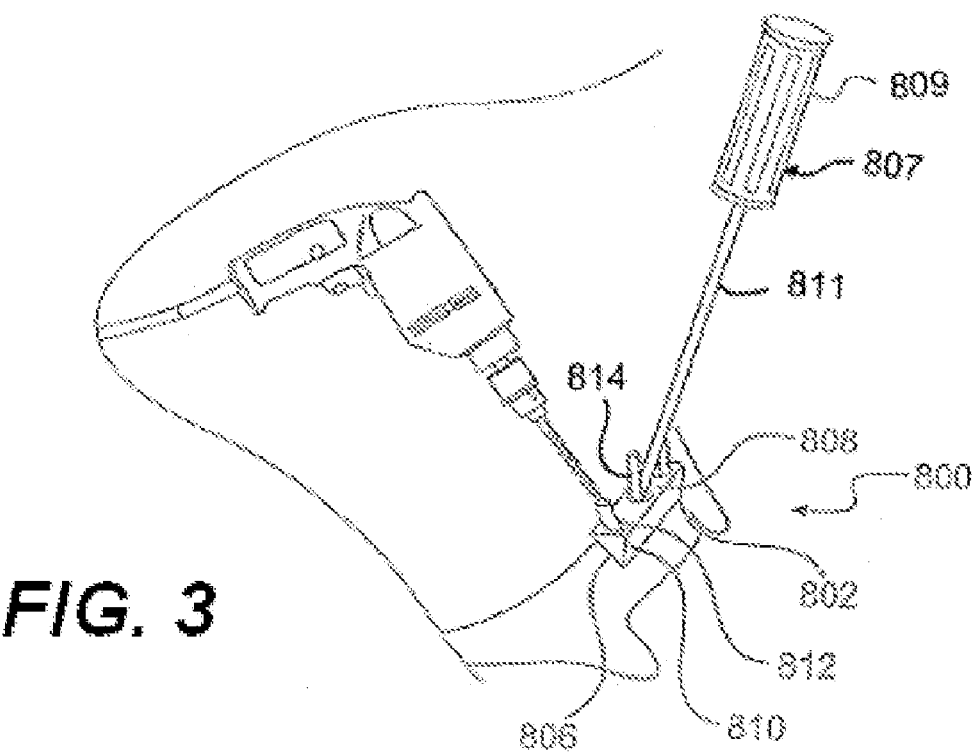
FIG. 3 is a fragmentary perspective of an exemplary embodiment of a drill guide positioned on the occiput of the cranium for creating oblique screw holes.

In an alternative embodiment, when inserted in centrally positioned aperture 340, fastener 42 may be a screw/rivet that enables rapid application. The screw or screw/rivet would preferably have torque strength of greater than 35 inch lb and generate sufficient pullout strength to prevent dislodgement from the cortex. The screw or screw/rivet would be placed near the middle of plate 300, and be fashioned to pass through the centrally positioned aperture 340 on plate 300. As shown in FIG. 3, a unique drill guide 800 may be used to guide a power drill to prepare holes in and/or insert fasteners 42 into the cranium or other bone structure for anchoring a surgical instrument, such as plate 300 and/or flange 325, thereto.

Figure 4:
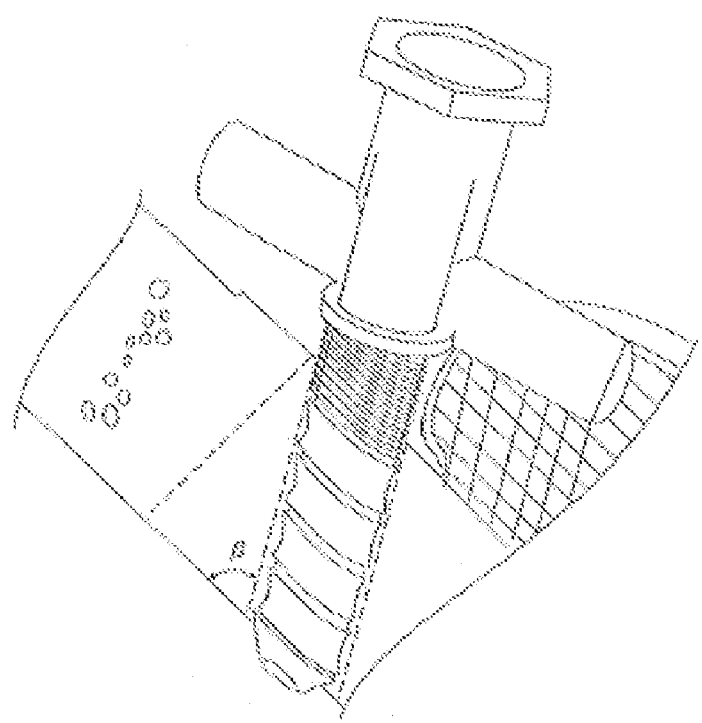
FIG. 4 is a fragmentary perspective of a triple threaded screw obliquely inserted in the occiput.
Figure 5:
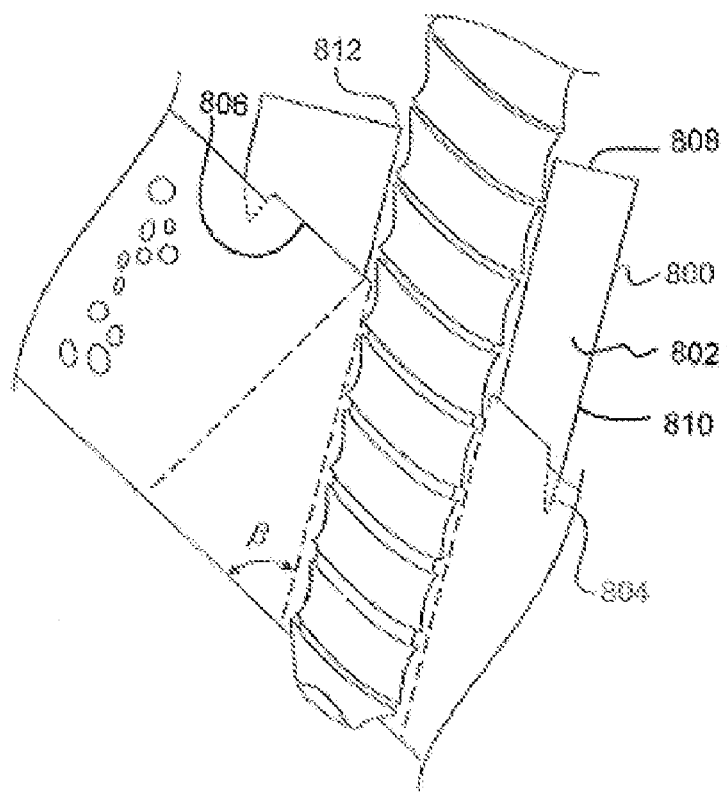
FIG. 5(a) is a fragmentary cross-section showing a drill bit received in the drill guide and creating an oblique screw hole in the occiput bone.

Drill guide 800 may enable angled insertion of a fastener 42 relative to the site of insertion, as shown in FIG. 4, to ensure secure attachment of any component of spinal stabilization system 100, including any component of plate 300, connection system 400, vertebral attachment system 500, transvertebral stabilization system 600, osteointegration apparatus 700 and cranial clamp 900, to an anatomical surface as well as to minimize the surgical exposure and risks associated with spinal stabilization procedures. In particular, FIG. 4 shows the insertion of a fastener 42, namely triple threaded screw 70, through a screw flange of the occipito-cervical spinal stabilization system and received in an oblique screw hole such that triple screw 70 is positioned oblique to the occiput. In an exemplary embodiment, drill guide 800 may be coupled to and conform to a curved anatomical surface so as to enable the insertion of a fastener 42 in an oblique direction thereto. Because drill guide 800 enables angled insertion of fastener 42 without creating a large incision, surgical risk and recovery time is minimized. The drill guide 800 may be used to insert any fastener 42 into any bone or soft tissue structure, including a vertebra and the cranium. As shown in FIG. 5, by inserting the fastener 42 at an oblique angle to the site of insertion, a greater length of the fastener 42 may is available for anchoring to and engaging an anatomical structure than would have been available if inserted perpendicular to the insertion site. Consequently, drill guide 800 creates a stronger and more secure attachment between fastener 42 and the anatomical structure to which it is anchored.

In the exemplary embodiment shown in FIG. 3, drill guide 800 has a guide body 802 defined by a lower surface 806, upper surface 808 and sidewalls 810. Guide body 802 may have any size, dimension or configuration suitable to guide and facilitate angled insertion of fastener 42 to an anatomical structure. Exemplary configurations may include a rectangular, square, pyramidal, spherical or domed structure. Similarly, lower surface 806, upper surface 808 and side walls 810 may have any suitable size, dimension or configuration, including a rectangular, square, triangular, circular or elliptical shape.

Figure 6:
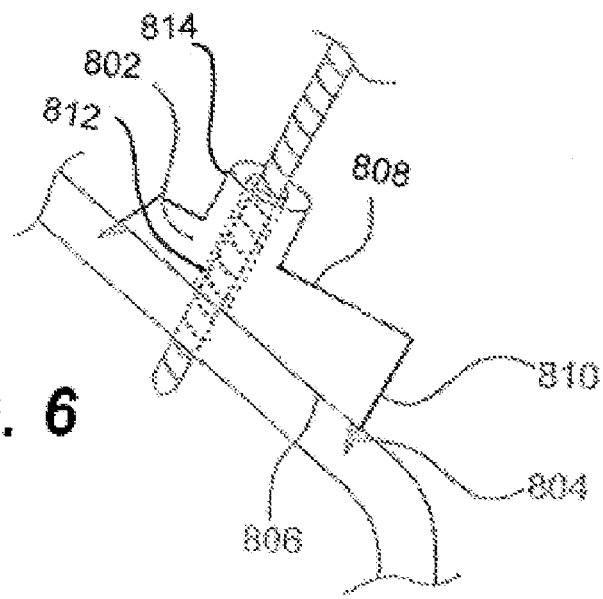
FIG. 6 is a fragmentary perspective of a drill angularly received in drill guide.

Lower surface 806 of guide body 802 may have a curved or multiplanar surface designed to conform to one or more contours of an anatomical surface, such as a bone surface. Exemplary anatomical surfaces may include any spinal or cranial surface, particularly any surface of the cranium or vertebra. Preferably, drill guide 800 may have a graduated depth with a slanted lower surface 806. For example, FIGS. 3 and 6 show a lower surface 806 of drill body 802 that is positioned on and conforms to the curvature of the occiput to enhance gripping and prevent slippage of drill guide 800 during use. In an exemplary embodiment, the lower surface 806 may be sufficiently malleable so as to enable a surgeon to mold and conform lower surface 806 to any anatomical surface; guide body 802, however, should remain substantially rigid in order to guide a drill bit and maintain its structural integrity and configuration during drilling so as to enable the steady insertion of a fastener 42 at a predetermined angle.

As shown in FIG. 5-6, drill guide 800 may further include one or more guide fasteners 804 positioned on a portion of the lower surface 806 to facilitate placement of drill guide 800 on an anatomical surface. Guide fasteners 804 function to removably secure drill guide 800 to an anatomical surface, preferably a bone surface, so as to cause little to no trauma during attachment or upon removal. Exemplary guide fasteners 804 may include teeth, hooks, barbs, ridges, latches or an adhesive means. Guide fasteners 804 may be positioned anywhere along lower surface 806, preferably along a perimeter, edge, corner, central region or combination thereof. In one embodiment, guide fasteners 804 may be configured as protuberances, such as teeth, hooks or barbs, that are extend from and are positioned at the corners and/or intermittently along an edge of lower surface 806. In an alternative embodiment, guide fasteners 804 may be configured as a ridge like protuberances that extends from and along one or more edges, preferably two or more edges of lower surface 806.

As shown in FIGS. 5-6, an upper surface 808 of the guide body 802 may include one or more apertures 812 that extend through drill guide 800 for receiving a drill bit and/or fastener 42. Additionally, drill guide 800 may also include one or more support structures 814 that extend upwards from upper surface 800 and may be configured as a tube like structure aligned with apertures 812 to further guide drill bit and/or fastener 42. In one embodiment, support structure 814 may be substantially rigid and linearly aligned with aperture 812, wherein aperture 812 and/or support surface 814 is substantially perpendicular to upper surface 808 of guide body 802. In one embodiment, drill guide 800 may include two or more, three or more or a plurality of apertures 812 and/or support structures 814 that have an assortment of different angles relative to upper surface 808, ranging from about 45° to about 90°, so as to enable oblique insertion of a drill or fastener 42 relative to the site of insertion. Multiple apertures 812 and/or support structures 814 may further allow for the simultaneous drilling and/or insertion of two or more fasteners 42.

Guide body 802 further includes a plurality of sidewalls 810, each of which may have the same or different heights. In one embodiment, one or more sidewalls 810 may vary in height along the length of the sidewall. In the embodiment shown in FIG. 5, drill guide 800 may have at least two sidewalls 810 of different heights to conform to a curved surface such that guide body 802 has a graduated depth along its length and/or width and a substantially level and horizontal planer upper surface 808. The difference in height between two or more sidewalls 810 creates a sloped lower surface 806 of about 4° to about 40°, preferably about 15° to about 20°. Therefore, when drill guide 800 is placed on a curved anatomical surface, wherein aperture 812 and/or support body 814 is substantially perpendicular to upper surface 808, a drill that passes therethrough will be inserted either at an acute, obtuse or oblique angle relative to the site of insertion, preferably at an angle of about 10° to about 45°, more preferably about 15° to about 30°.

As shown in FIG. 3, drill guide 800 may further includes a rigid handle 807 integrally or removably attached to a surface of the guide body 802 to facilitate orientation of drill guide 800 as well as to maintain placement of drill guide 800 during drilling or insertion of fastener 42. Handle 807 has a hand grip region 809 connected to an elongated shaft 811 that may be integrally formed with or removably attached to an upper surface 808 or sidewalls 810 of guide body 802. Alternatively, shaft 811 may be removably inserted in or integrally formed within a surface of guide body 802 defining aperture 812 and/or support structure 814. When configured to enable removable attachment, a distal end of elongated shaft 811 may include a handle fastener that may be coupled to one or more corresponds guide body fasteners. Exemplary handle fasteners and corresponding guide body fasteners may be hooks, latches, notches, male fasteners, or female fasteners. Preferably, a plurality of guide body fasteners may be positioned on an upper surface 808, a side surface 810, an interior surface of guide body 802 defining aperture 812, an interior or exterior surface of support structure 814, or combinations thereof.

Connection System

Spinal stabilization system 100 may further include a connection system 400 that functions to connect the various components of spinal stabilization system 100 to enable a wide variety of spinal applications, such as rigid fixation. Connection system 400 may be modular so as to accommodate and enable fixation of a plurality of different spinal stabilization components that may be oriented in a wide variety of different orientations. In the exemplary embodiment of FIG. 1, connection system 400 may include one or more support rods 450, 452 and one or more fastener assemblies 462, 464, 402, 404, 406, 408.

As shown in the exemplary embodiment of FIG. 1, connection system 400 may be operatively associated with the apertures 336, 338, 340, 344, 346 of plate 300 and/or flange 325, which may be configured as pre-drilled threaded mounting holes 336, 338, 340, 344, 346, 372 to facilitate attachment of plate 300 and/or flange 325 to one or more components of spinal stabilization system 100, such as vertebra attachment system 500 and cranial attachment system 900. In an exemplary embodiment, one or more support rods 450, 452 may pass through one or more perforation 334 in plate 300 and/or flange 325 to connect to the triple screw, either by inserting a support rod 450, 452 through a hole 69 defined in the triple screw 70 or by inserting the triple screw 70 through a hole 468 defined in a support rod 450, 452. Alternately, plate 300 and/or flange 325 may have a groove, a pop-out section or may have a region that possesses the faculty of perforability to allow passage of the stabilization element connecting cranium to spine. This configuration may be advantageous in lowering the overall profile of the rod, thereby minimizing the potential deformity of overlying tissue.

In an exemplary embodiment, first portions 454, 458 of first and second support rods 450, 452 may be connected to plate 300 and/or flange 325 by means of first and second fastening assemblies 462, 464, respectively. The plate 300 therefore preferably includes manifold screw holes in order to permit the support rods 450, 452 to be secured to the plate 300 and locations that are most suitable for an individual patient. Second portions 456, 460 of the first and second support rods 450, 452 are secured to the cervical spine of the patient, as will be described in greater detail below. As shown in FIG. 1, fasteners 42 and fastener assemblies 462 engaged in plate 300 and/or flange 325 may serve to anchor stabilization elements, such as rods, plates or other structures, of spinal stabilization system 100.

Figure 12:
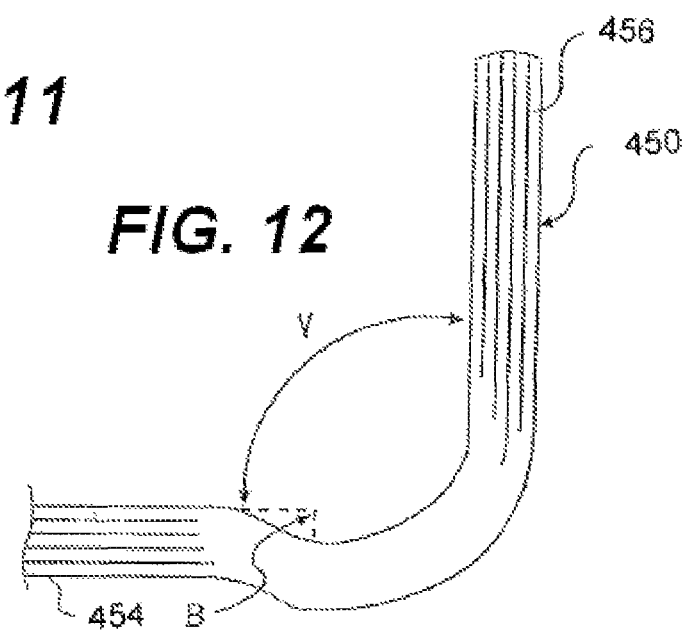
FIG. 12 is a fragmentary side elevational view of one component of the system that is depicted in FIG. 1.

The first and second support rods 450, 452 provide the main structural connection between the cranium and the upper cervical spine during the immediate postoperative period. Support rods 450, 452 are preferably standard titanium rods, approximately of about 3-4 mm gauge, bent to conform to the correct craniospinal angle. The salient distinguishing features of support rods 450, 452 relative to other rods currently available are two-fold. The first is bending rods 450, 452 at an γ angle reflecting the corrected reduction of the angle between the cranium and that of the spine, as shown in FIG. 12; in the preferred embodiment, this will be pre-set, thus introducing a bend in the rod having an angle, γ, within a range of about 70° to about 90°, preferably about 75° to about 90° to achieve an obtuse angle of preferably about 110° to about 90°, more preferably about 105° to about 90°, between the occiput of the cranium and the posterior lamina of the cervical vertebra, as shown in FIG. 2. Accordingly, the first and second support rods 450, 452 are contoured to ensure a postoperative craniospinal relationship that confers a clivo-axial angle (the angle between the dorsum of the second cervical vertebra and the dorsum of the clivus) approaching about 145° to about 165°, and more preferably about 155° to about 165°. Simultaneously, the degree of ventral brainstem compression should be rendered close to zero, by virtue of the reduction of angulation between the cranium and spine, and in some cases by the posterior translation of cranium upon the spine.

Second, the craniospinal support rods 450, 452 will have a pre-established rise option (the β rise, FIG. 12), to accommodate the non-linearity of the level of the posterior ring of the first cervical vertebra C1 to the surface of the lamina of C2 and lateral mass of C3. Accordingly, the presence of the pre-established β rise will allow the support rods 450, 452 to contact the C1 and C2 laminae.

Figure 7A:
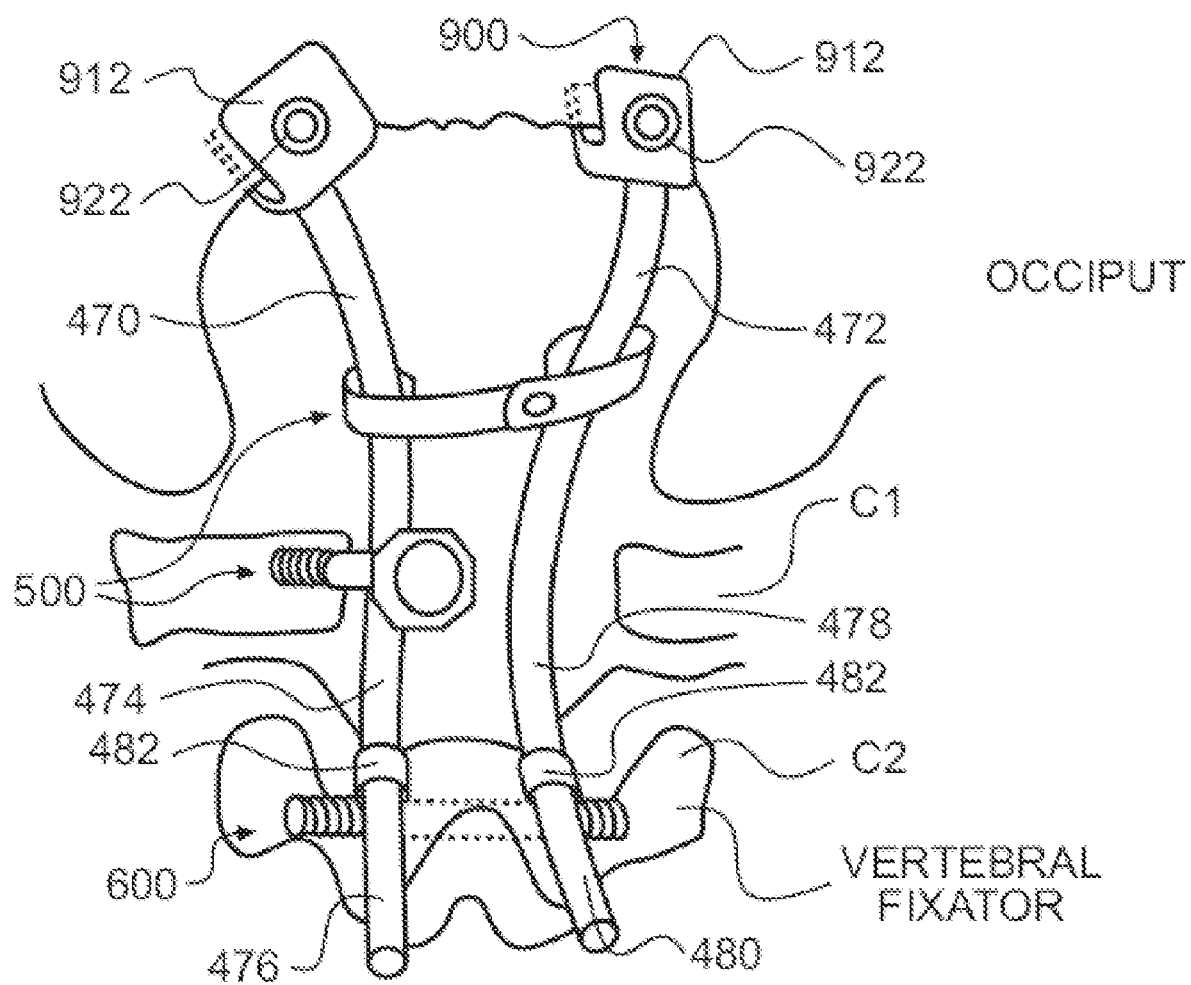
FIG. 7(a) is a fragmentary perspective view of a system for effecting fusion of the human occipitocervical junction using an articulating rod system.
Figure 7B:
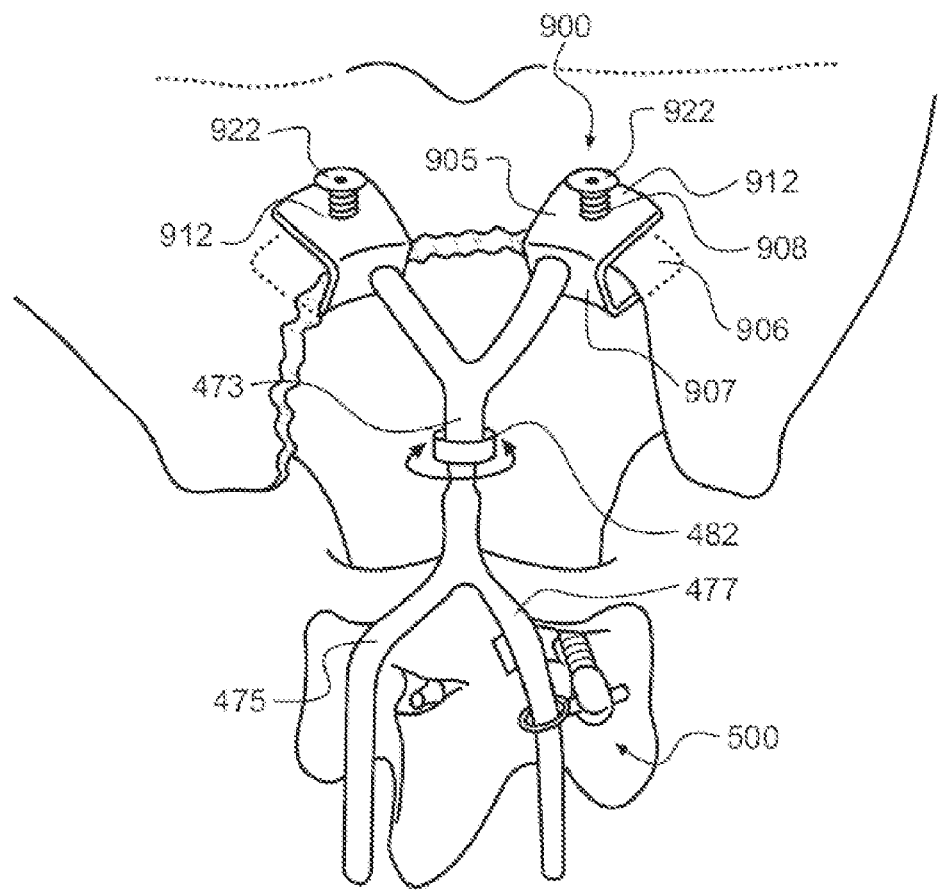
FIG. 7(b) is a fragmentary perspective view of a system for effecting fusion of the human occipitocervical junction using an alternative articulating rod system.

In an alternative embodiment shown in FIGS. 7(a)-(b), connection system 400 may include an articulating rod system having one or more articulating support rods 470, 472 that may be attached to a cranial and vertebral surface as well as to one or more components of spinal stabilization system 100, including one or more components of plate 300, cranial attachment system 900, vertebral attachment system 500 or combinations thereof. Each of first and second articulating support rods 470, 472 may have one or more rod members 474, 476, 478, 480 configured as conventional rigid spinal rods suitable for load bearing applications. Additionally, articulating support rods 470, 472 may be constructed from the same material as that of the previous discussed embodiment, preferably a plastic material having an elastic characteristic or a carbon fiber material. These rod members may be connected by one or more, two or more, three or more, preferably no more than about three, articulating joints 482 to permit a limited amount of rotational motion, lateral bending or combinations thereof. Exemplary joints, may include a swivel mechanism or ball and socket couplings, enable articulating support rod 470, 472 to enable limited rotation, lateral bending or combinations thereof. In the embodiments shown in FIG. 7(a), articulating joint 482 enables rotation of a first pairs of rod members 474, 476 and second pair of rod members 478, 480 relative to one another. In an exemplary embodiment, the articulating rod system enables up to and including about 20° of lateral bending in flexion extension mode in the sagital plane, about 10° in each direction. Preferably, the system may enable about 10° to about 15° of lateral bending in one or both directions. The system may also enable up to and including about 10° of rotation and up to and including about 10° of side to side movement, preferably up to and including about 5° of side to side movement. Articulating support rods 470, 472 therefore may be used to facilitate spinal stabilization but does not fuse the skull and spine.

In an alternative embodiment, the articulating rod system may have a bifurcated configuration such that an articulating support rod 471 that includes a base rod member 473 that attaches to a cranial surface, a plate 300, cranial attachment system 900 or combinations thereof and bifurcates into a first rod member 475 and second rod member 477 that are connected to the cervical vertebrae and/or a vertebral attachment system, forming a forked Y shaped configuration. In one embodiment base rod member 473 may have a larger gauge of about 4 mm to about 9 mm than first and second rod member 475, 477. An articulating joint 482 connects the base rod member 471 to first and second rod members 475, 477 to allow for rotational motion and/or lateral bending about one or more axis at articulating joint 482. In one embodiment shown in FIG. 7(b), articulating joint 482 is a swivel mechanism that enables rotational motion about a horizontal y axis at the articulating joint 482. In this embodiment, articulating support rod 471 may be bifurcated both at a proximal for attaching to two cranial clamps 912 and at a distal end for attaching to two different portions of a vertebra. In another embodiment, a ball or socket is positioned on a distal end of base rod member 471 designed to be operatively coupled to a corresponding socket or ball that is integrally connected first and second rod members 475, 477 to enable rotational and lateral bending. To enable further motion, rod members 471, 473, 475 may include additional articulating joints positioned along the length thereof.

The articulating rod system may be used with any component of spinal stabilization system 100 of the present invention, including the various embodiments of bone scaffold system 200, plate 300, vertebral attachment system 500, cranial attachment system 900, a trans-vertebral stabilization system 600 and an osteo-generation apparatus 700. Alternatively, the articulating rod system may be used with any other spinal stabilization system.

Figure 8A:
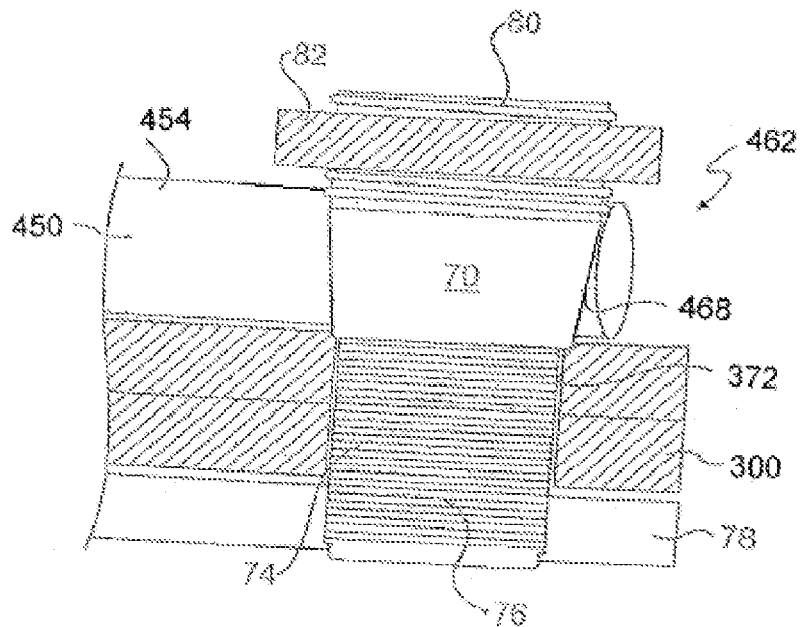
FIG. 8(a) is a fragmentary cross-sectional view depicting a fastening assembly that is constructed according to a preferred embodiment of the invention.

First and second fastening assemblies 462, 464 connect support rod 450, 452 to a craniospinal surface and optionally, to one or more other surgical instruments, such as a component of plate 300 and/or cranial attachment system 900. An exemplary first and second fastening assembly 462, 464 configured as a triple screw 70 is shown in greater detail in FIGS. 8(a)-8(b). In the preferred embodiment, an unthreaded hole 468 is defined in the first portion 454 of the first support rod 450 and a threaded hole 372 is provided in the plate 300. Triple screw 70 advantageously has a first threaded portion 76 at a lower section or distal end thereof that is constructed and arranged to be screwed into the cranial bone 78 and a second portion 74 at an intermediate section thereof that is sized and pitched to mate with the threaded hole 372 in the plate 300.

Triple screws 70 have the unique characteristic of deriving stability from fixation within the skull, the plate 300 and around the rod or plate that connects the cranium to the spine. In addition, the triple screw 70 is tri-purposive: first, it connects the plate to the cranium; second, it screws into or fits tightly and secures the plate, third it attaches to and secures the plate to the craniospinal connecting devices; by attaching to the skull, it eliminates plate torque around the central screw 42. In so doing, it eliminates one of the steps common to all other craniospinal devices: that of an additional and independent means of attaching the plate 300 to the craniospinal rod or plate connector.

Triple screws 70 are so-called because they possess three functional portions of the screw length: a threaded first portion 76 for attachment to the cranial bone 78, a threaded, or non-threaded, second portion 74 that may be configured to engage a first surgical instrument, such as plate 300, and a third threaded portion 80 for attaching a second surgical instrument, such as support rod 450. The central or intermediate first portion may be threaded to enhance binding to the plate 300, or non-threaded to allow a lag effect upon the plate 300, in order to allow the insertion of the screw to tighten the plate down to the cranial bone 78, depending upon the requirements of the particular stabilization. Additionally, each portion may have a different diameter, a different sized threading, or different contour, different length, or combinations thereof that is customized to for the aforementioned function.

The triple screws 70 may be placed in one of many potential screw holes on each side of the plate 300, in order to accommodate to the variability of the system that attaches the cranium to the cervical spine. Whilst the triple screws 70 are shown in the upper portion of the plate in the illustrated embodiment, they may in another embodiment be placed in the lower aspect of the plate. They are not limited to being positioned at lateral opposite sides of the plate 300, but may be placed near the middle of the plate 300. The triple screw 70 can be turned to any direction to accommodate the craniospinal rod 450, 452 or connection system 400.

The triple screw 70 will preferably be inserted through the plate and screwed into the skull. The triple screw 70 will provide increased stability to the plate and rod system by virtue of the combined fixation of the screw within the plate and the skull. The triple screw 70 may be threaded at the level of the skull with a cortical or cancellous thread, or could in another embodiment utilize a rivet-type fixation. In any event, the internal portion of the screw is firmly fixated to the skull.

Figure 8B:
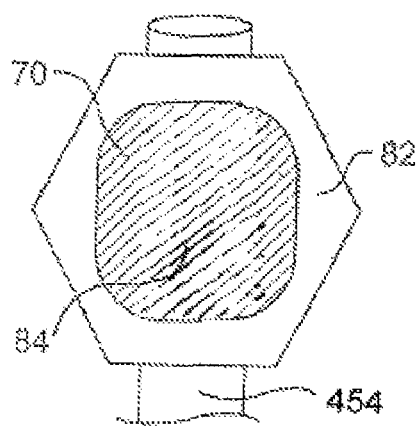
FIG. 8(b) is a fragmentary top plan view of the fastening assembly that is depicted in FIG. 8(a)

Triple screw 70 further includes a third threaded portion 80 at an upper portion thereof that is sized in pitch to mate with an internally threaded hexagonal nut 82. As is shown in FIG. 8(b), which provides a top plan view of the first fastening assembly 462 configured as a triple screw 70, wherein an upper surface of the triple screw 70 and/or nut 82 is provided with a slot 84 for receiving a screwdriver blade.

Figure 9A:
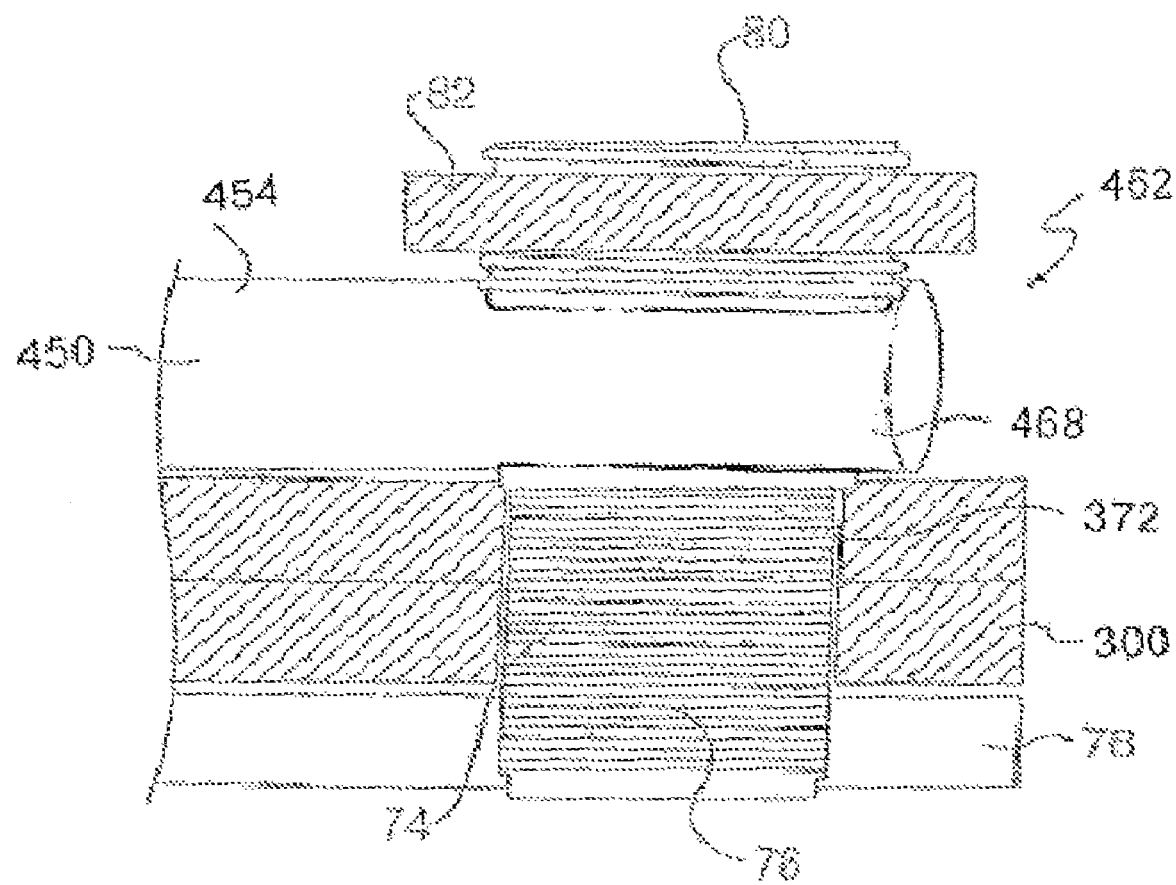
FIG. 9(a) is a fragmentary cross-sectional view depicting another fastening assembly that is constructed according to a preferred embodiment of the invention.
Figure 9B:
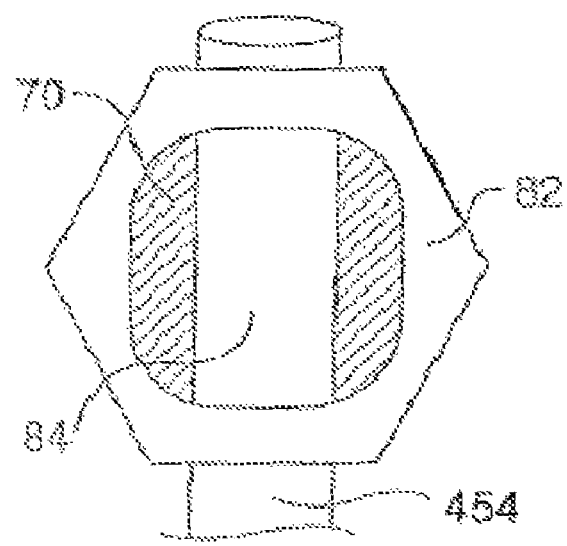
FIG. 9(b) is a fragmentary top plan view of the fastening assembly that is depicted in FIG. 9(a)

In the exemplary embodiment shown in FIGS. 9(a)-9(b), first and second fastening assemblies 462, 464 are configured as alternative triple screws embodiment that further includes a hole 69 defined through the width of triple screw 70 and below nut 82 for receiving, engaging and retaining the first support rod 450. Hole 468 may be positioned in any body portion of triple screw 70, including the first, second and third portions 76, 74 and 80. As shown in FIG. 9(a), hole 69 is preferably located between the first and third portions 76, 80.

Additional fastening assemblies 402, 404, 406, 408 having the same structure and configuration as first and second fastening assemblies 462, 464 may connect support rods 450, 452 to spinal vertebrae and/or one or more surgical instruments, such as one or more components of vertebral attachment system 500.

Figure 10:
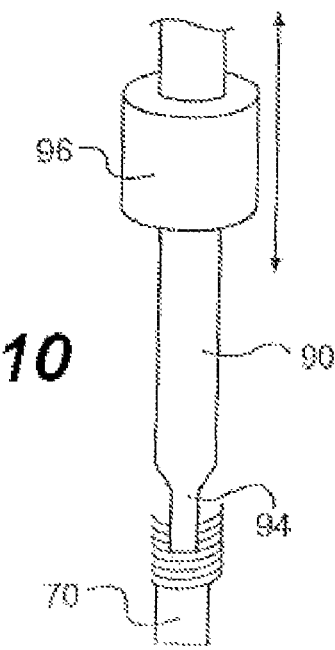
FIG. 10 is a diagrammatical depiction of a fastening tool that is designed to be used in conjunction with the fastening assembly that is depicted in FIGS. 8(a)-9(b), shown in a first operative position.
Figure 11:
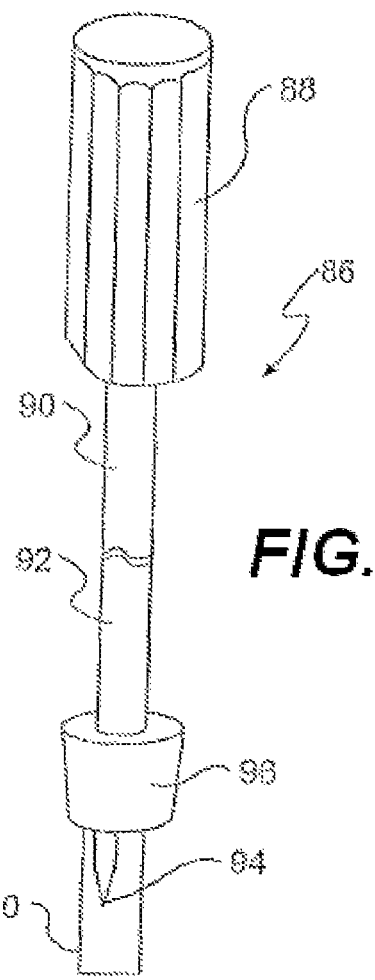
FIG. 11 is a diagrammatical depiction of the fastening tool that is shown in FIG. 10, shown in a second operative position.

FIGS. 10-11 depict a unique tool 86 that is constructed and arranged to be used in conjunction with the fastening assembly 462, particularly when configured as triple screw 70. Tool 86 includes a handle 88 and a shaft 90 that may be provided with a universal joint 92 for accessibility purposes, e.g. to accommodate non-orthogonal placement of the screw. For instance, if access to the triple screw 70 is encumbered by a patient's corpulence, the screw may be inserted at an angle. A screwdriver blade 94 is provided at a distal end of the shaft 90 and is preferably sized and shaped to be effectively received by the slot 84 that is defined in the upper surface of the triple screw 70. Additionally, tool 86 preferably includes a sleeve 96 that is slidable upwardly and downwardly on the lower portion of the shaft 90 between a first retracted position that is shown in FIG. 10 and a second, extended operative position that is shown in FIG. 11. Sleeve 96 is shaped to define an internally threaded socket that mates with the external thread of third portion 80 of the triple screw 70. Sleeve 96 is further mounted to the shaft 90 so that it is prevented from rotating with respect to the shaft 90. Accordingly, a surgeon may use the tool 86 in the operative position that is shown in FIG. 10 in order to tighten the triple screw 70 with respect to the plate 300 and the cranial bone 78 with the sleeve 96 stabilizing the tool 86 with respect to the triple screw 70 and preventing the blade 94 from slipping out of the slot 84.

Integrated Plate and Connection System

Figure 13:
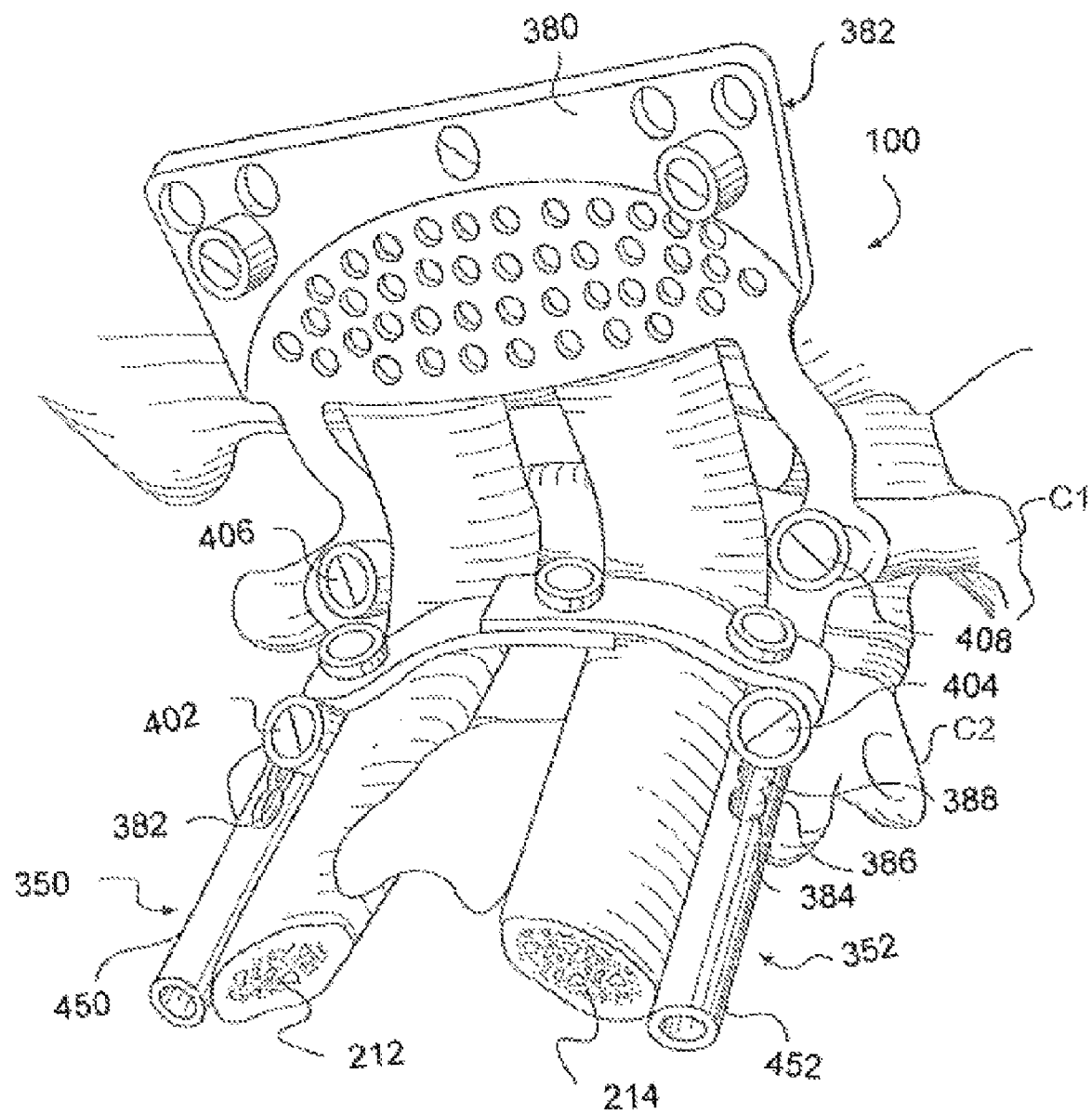
FIG. 13 is a fragmentary perspective view showing another embodiment of the invention.

Referring now to FIG. 13, spinal stabilization system 100 of the present invention may be constructed according to an alternative exemplary embodiment including an integrated fixation member 382 wherein plate 380 is integral and preferably unitary with first and second appendages 350, 352. The appendages 350, 352 would intimately relate to the posterior ring of C1 (the first vertebra and the lateral mass of C2, C3 and to any of the lower vertebrae, even as low as the thoracic vertebrae). The goal of the monolithic design would be to simplify and increase the efficiency of application and stabilization of the device to the craniospinal junction.

Plate portion 380 is preferably constructed identically to plate 300 described above with reference to the previously described embodiment except as is described otherwise herein. The first and second appendages 350, 352 are preferably rigid and in the preferred embodiment are integral with and/or extend from a pair of generally parallel extending rod members 450, 452. Appendages 350, 352 are preferably preformed as described above with reference to the first embodiment of the invention so as to be bent at an angle reflecting the corrected reduction of the γ angle, shown in FIG. 12, between the cranium and that of the spine, which in the preferred embodiment this will be pre-set within a range of about 75° to about 90°, preferably about 75° to about 90° to achieve an obtuse angle of preferably about 110° to about 90°, more preferably about 105° to about 90°, between the occiput of the cranium and the posterior lamina of the cervical vertebra. Accordingly, the first and second integrated appendages 350, 352 are contoured to ensure a postoperative craniospinal relationship that confers a clivo-axial angle (the angle between the dorsum of the second cervical vertebra and the dorsum of the clivus) approaching about 145° to about 165°, more preferably about 155° to about 165° and more preferably about 165°. Simultaneously, the degree of ventral brainstem compression should be rendered zero, by virtue of the reduction of angulation between the cranium and spine, and in some cases by the purposeful posterior translation of cranium upon spine.

In addition, the integrated appendages 350, 352 preferably incorporate a pre-established rise option (the β rise, described above with reference to FIG. 12), to accommodate the non-linearity of the level of the posterior ring of the first cervical vertebra C1 to the surface of the lamina of C2 and lateral mass of C3. The presence of the pre-established β rise will allow the integrated appendages 350, 352 to contact the C1 and C2 laminae, as shown in FIG. 12.

Another advantageous feature of the embodiment of the invention that is depicted in FIG. 13 is the provision of adjustment slots 382, 384 in the first and second appendages 350, 352, respectively, to permit positional adjustment of the integrated fixation member 382 with respect to the fastener assemblies 402, 404 that are used to secure the first and second appendages 350, 352, respectively, to the pedicle of the C2 vertebrae. As FIG. 13 shows, adjustment slot 384 as well as adjustment slot 382 may include a plurality of prepositioned apertures or adjustment holes 386, 388 to permit indexing of fastener assembly 404 within the appendage 352 or variability of screw purchase.

Likewise, adjustment slots 384, 382 may be provided in the respective portions of the first and second appendages 350, 352 that are constructed and arranged to be secured to the C1 vertebrae by fastener assemblies 406, 408. This portion of the appendages 350, 352 is preferably constructed so as to be slightly flared at the C1 vertebrae to allow lateral variability.

As may be visualized from viewing FIG. 13, several possibilities of latitude are offered for the screw heads at C1, and several options for the screw heads of C2 are also available. The appendages 350, 352 may be solid, tubular, porous or even a metallurgically bonded porous metal coating that is constructed and arranged to encompass and contain bone graft material, such as the material that is marketed under the trade name TRABECULAR METAL™ by Zimmer Inc. of Warsaw, Ind.

Vertebral Attachment System

Referring now to FIGS. 14-16, spinal stabilization system 100 may further include a unique vertebral attachment system 500 for positioning and biasing the second portions 220, 222 of the first and second scaffold members 212, 214 against at least one cervical vertebral body of a human cervical spine so as to promote bone fusion between the cervical vertebral body and the respective scaffold member 212, 214.

In a first exemplary embodiment shown in FIGS. 14-16, vertebral attachment system 500 includes a transversely oriented vertebral plate 550 that is positioned to compress the first scaffold member 212 and second scaffold member 214 against a vertebral body such as the vertebral body C2 that is depicted in FIG. 14. The vertebral plate 550 serves several purposes. First, the vertebral plate 550 holds the graft material (the bone, bone substitute or other non-osseous material) in close contact, and usually under pressure, with the underlying spinal vertebrae, to facilitate in-growth of blood vessels or other tissue, as is dramatically depicted in FIGS. 14-15. Second, the vertebral plate 550 stabilizes the two sides of the spinal stabilization system 100, connecting the respective support rods 450, 452 from one side to that of the other, thereby decreasing the potential for toggling.

Accordingly, the vertebral plate 550 is connected to the first support rod 450 at one portion thereof that includes a first clamping structure 552 for releasably clamping one end of the vertebral plate 550 to the first support rod 450. In the preferred embodiment, the first clamping structure 552 includes a curved plate portion 556 that curves about most of the circumference of a first support rod 450. A fastener 42, preferably configured as a screw, extends through first and second holes that are defined in the curved plate portion 556 for tightening and loosening the first clamping structure 552 with respect to the first support rod 450.

Likewise, the vertebral plate 550 is connected to the second support rod 452 at a second portion thereof that includes a second clamping structure 554 for releasably clamping a second, opposite end of the vertebral plate 550 to the second support rod 452. The second clamping structure 554 includes a curved plate portion 558 that curves about most of the circumference of the second support rod 452. A screw 120 extends through first and second holes that are defined in the curved plate portion 558.

The curved plate portions 556, 558 of the respective clamping mechanisms 552, 554 preferably extend around the circumference of the respective support rod 450, 452 as viewed in transverse cross-section for an angular distance of at least three radians. In addition, the fasteners 42, preferably configured as clamping screws, are preferably positioned on the medial side of the respective support rod 450, 452.

The vertebral plate 550 is preferably curved so as to be concave on a side thereof that is positioned to contact the first scaffold member 212 and said second scaffold member 212.

The vertebral plate 550 further preferably includes structure for permitting adjustment of a length of the vertebral plate 550, whereby a lateral spacing distance between said first and second laterally spaced support rods may be adjusted. In the preferred embodiment, this is accomplished by constructing the vertebral plate 550 out of two separate components that are attachable to each other, specifically a first curved connector portion 564 and a second curved connector portion 566, as is best shown in FIG. 16.

The first connector portion 564 has a plurality of adjustment holes 570 defined therein while the second connector portion 566 similarly has a plurality of adjustment holes 572 defined therein. A top-loading fastener 42, preferably configured as a screw, which is best shown in FIG. 14, is provided for securing the first connector portion 564 to the second connector portion 566 and is preferably applied centrally in a precise manner in order to stabilize the first and second connector portions 564, 566. Fastener 42 is preferably although not necessarily a lock screw having a snap off head. A Vernier scale option may be used to generate the best precise fit, but other adaptations may be used, with the most important requirement being that a secure fit is created.

The graft loading vertebral plate component arms 564, 566 are preferably curved, and may possess a plurality of curve sizes to accommodate the specific graft or implanted material size. In one possible alternative embodiment, the vertebral plate arms are straight with a rise to accommodate the underlying material.

The surgically implantable instrumentation of the spinal stabilization system 100 that has been described above, including the plate 300 the support rods 450, 452 and the vertebral plate 550 may alternatively be fabricated from a bioabsorbable material that progressively loses its strength and mass over time as it is absorbed into the human body. The ideal bioabsorbable material would have a composition that would retain sufficient strength for a sufficient period of time for adequate bone fusion and bone mass to develop so that the first and second bone forming material based structural members 212, 214 would provide adequate structural strength to maintain the fusion of the human occipitocervical junction at all times and under all foreseeable circumstances.

Figure 17:
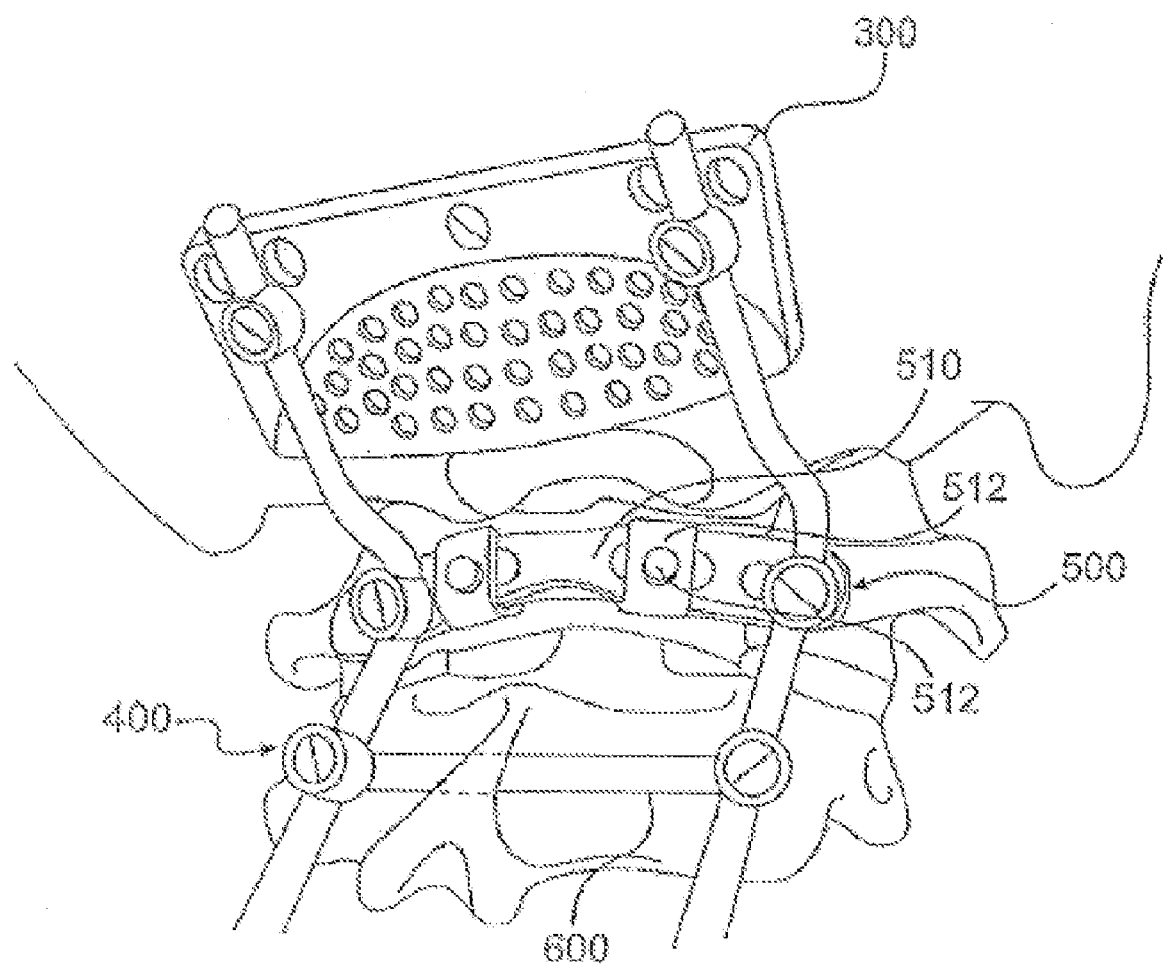
FIG. 17 is a perspective view of an exemplary embodiment of a C1 attachment system being utilized to connect the C1 vertebra to another system that stabilizes the skull and spine.

In a second exemplary embodiment shown in FIGS. 17-22(c), vertebral attachment system 500 may include at least one vertebral clamp 512, at least one vertebral fastener 522, and at least one vertebral plate 510 configured to be securely fastened to any vertebra of the spinal column. Vertebral attachment system 500 may be designed such that vertebral clamp 512 and vertebral fastener 522 securely anchor vertebral plate 510 to a portion of a vertebra, as shown in FIG. 17. Vertebral plate 510 in turn may be connected to other orthopedic structures and assemblies. In an exemplary embodiment, vertebral attachment system 500 may be structurally configured to enable attachment to a posterior region of vertebra and may be able to withstand at least normal spinal loads. It is envisioned that the system of the present invention may be compatible with any orthopedic structure or assembly to enable spinal stabilization between vertebrae and/or enable stabilization of the occipitocervical junction.

Figure 18A:
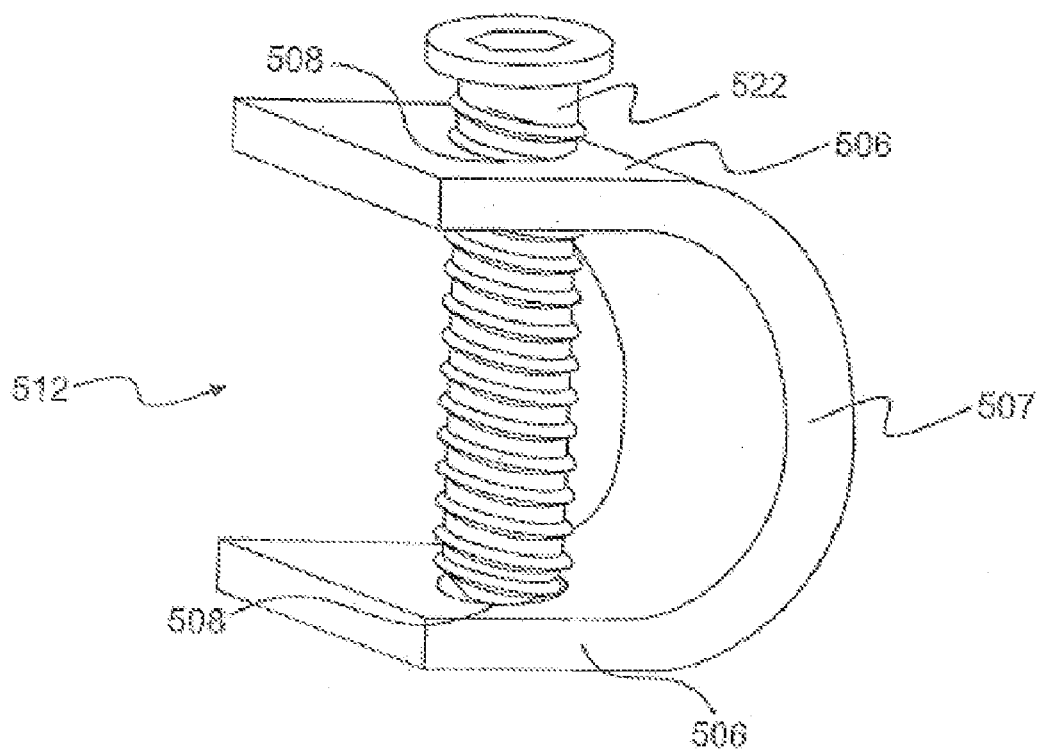
FIG. 18(a) is a perspective view of an exemplary embodiment of the clamp.
Figure 18B:
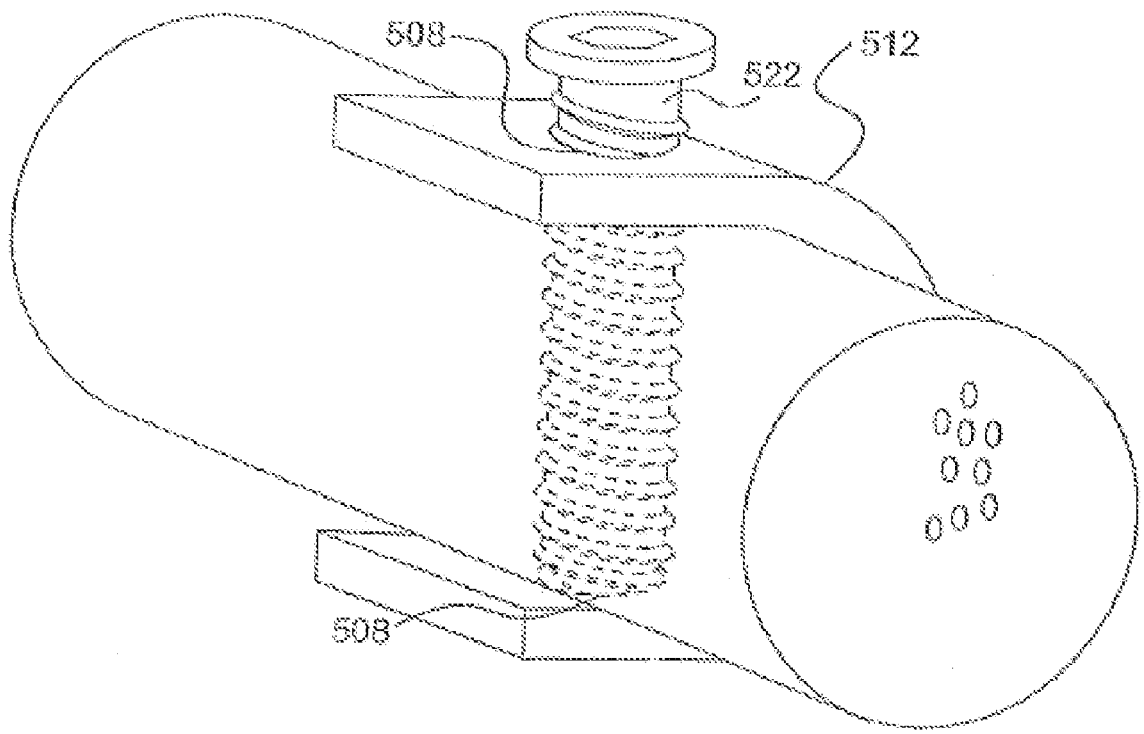
FIG. 18(b) is a perspective view of an exemplary embodiment of the clamp on the posterior region arch of the C1 vertebra.
Figure 18C:
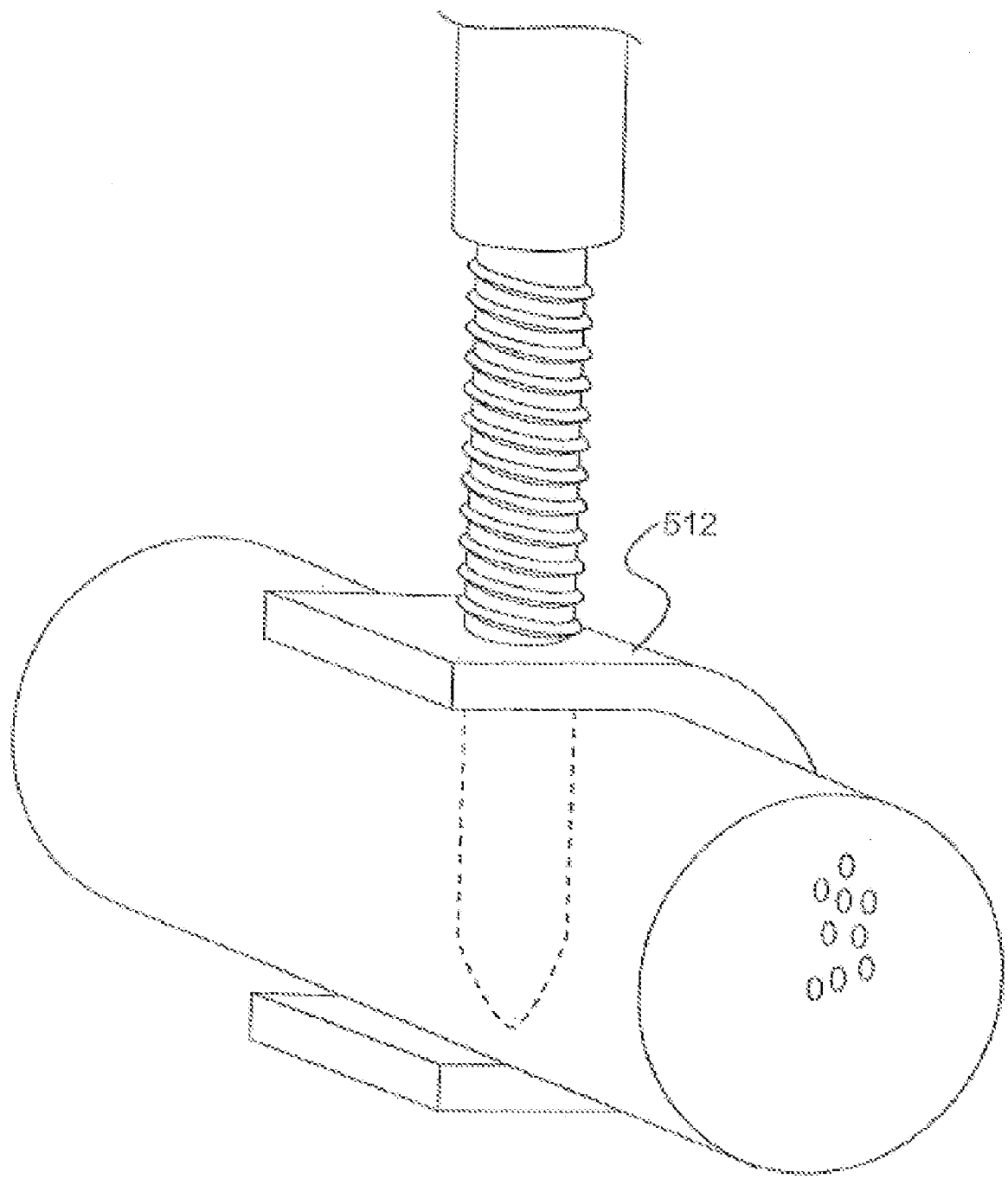
FIG. 18(c) shows a drill creating a hole that penetrates the posterior arch of the C1 vertebra from the dorsal to ventral side.

Vertebral clamp 512 may have any structure, dimension, configuration or geometric shape suitable for gripping, clasping, clipping or otherwise retaining a portion of a vertebra so as to enclose, surround and retain an upper, lower and side surface of a vertebra. In one embodiment, at least one portion of vertebral clamp 512 conforms to a surface of a vertebra. Preferably, vertebral clamp 512 may be sized and shaped to surround a posterior region of a vertebra. As shown in FIGS. 18(a)-18(b), vertebral clamp 512 may include a curved surface having a circumference of approximately 4 radians that encircles an upper, lower and side portion of the posterior arch of the C1 vertebra. In an exemplary embodiment, vertebral clamp 512 may have at least two members, a first member 505 for engaging an upper surface of a vertebra and a second member 506 for engaging a lower surface of a vertebra that is separated by a space sized to accommodate a portion of vertebra. First and second members 505, 506 may be opposed and spaced apart from one another in a parallel or V shaped configuration. Vertebral clamp 512 may also include a third member 507 that connects first and second members 505, 506 so as to abut and engage a side surface of the posterior arch to further facilitate the retention of vertebra. As shown in FIG. 18(a), vertebral clamp 512 may have a U, semi-circular or collar like shape. Preferably, vertebral clamp 512 is configured to be sufficiently thin and have a low profile such that it does not substantially obstruct, compress or impinge any adjacent vertebral components. In an alternative embodiment, first and second members 505, 506 may have the same structure and configuration as first and second members 905, 906 of cranial clamp 912 shown in FIG. 23(c).

In an exemplary embodiment, at least one aperture 508 may be defined in vertebral clamp 512 for receiving vertebral fastener 522. The inner surface of aperture 508 may be smooth, partially threaded or completely threaded; aperture 508 may also include bevels, collars, insets or any other structure that would facilitate the retention of vertebral fastener 522. In an exemplary embodiment, vertebral clamp 512 may include a plurality of apertures 508, preferably two or more pairs of apertures 508 defined in first and second members 505, 506. Preferably, at least one aperture 508 defined in a first member 505 may be geometrically aligned with an aperture 508 defined in a second member 506. Apertures 508 of vertebral clamp 512 may have a variety of different sizes and shapes to accommodate different vertebral fasteners 522.

Vertebral clamp 512 may be fabricated from any high strength and biocompatible material. In an exemplary embodiment, vertebral clamp 512 may be fabricated from any material having sufficient material and mechanical properties that would enable load bearing applications including spinal stabilization. The material used to fabricate vertebral clamp 512 may include a biocompatiable metal, metal alloy, ceramic, polymer, such as a polymer from the polyaryletherketone family (PAEK) family, such as polyether ether ketone (PEEK) or polyether ketone ketone (PEKK), or composite material. Preferably, the material may include a metal alloy, such as a titanium alloy. Optionally, the surface of vertebral clamp 512 may be treated to adjust the frictional, wear or biocompatibility properties of vertebral clamp 512. In an exemplary embodiment, at least one portion of vertebral clamp 512 may be coated with a material, contoured, and/or textured to limit a range of motion of vertebral clamp 512 relative to the vertebra and/or vertebral plate 510. In another embodiment, vertebral clamp 512 may be coated with a material to minimize wear of vertebral clamp 512 and/or facilitate osteointegration.

Vertebral attachment system 500 may include any number of vertebral clamps 512 to attach vertebral plate 510 to a vertebra. In an exemplary embodiment, a sufficient number of vertebral clamps 512 may be attached to a vertebra to enable spinal stabilization applications. Preferably, the system may include at least about one to three vertebral clamps 512, more preferably, about two to three vertebral clamps 512.

As shown in FIGS. 18(a)-18(d), vertebral fastener 522 may removably secure vertebral clamp 512 to a vertebra. Vertebral fastener 522 may be any element that is compatible with vertebral clamp 512 and vertebral plate 510 so as to enable load bearing applications, such as spinal stabilization. In an exemplary embodiment, vertebral fastener 522 may have the same configuration as fastener 42 and/or fastening assembly 462. Vertebral fastener 522 may have any suitable dimension, configuration or geometric shape. In an exemplary embodiment, vertebral fastener 522 may include a threaded component, hook, latch, pin, nail, wire, tether, or combinations thereof. Preferably, vertebral fastener 522 may be sized and shaped to secure vertebral clamp 512 to a posterior region of a vertebra. Vertebral attachment system 500 may include a plurality of vertebral fasteners 522 having different configurations and/or dimensions compatible with vertebral clamp 512 and vertebral plate 510.

Vertebral fastener 522 may be fabricated from any material suitable for securing vertebral clamp 512 to a vertebra. In an exemplary embodiment, vertebral fastener 522 may be fabricated from any high strength and biocompatible material. The material used to fabricate vertebral fastener 522 may include a biocompatiable metal, metal alloy, ceramic, polymer, such as a polymer from the polyaryl ether ketone family (PAEK) family, such as polyether ether ketone (PEEK) or polyether ketone ketone (PEKK), or composite material. Preferably, the material may include a metal alloy, such as titanium.

Optionally, vertebral fastener 522 may also include a lock 509 to further secure the retention of a portion of a vertebra. Lock 509 may be any mechanism that ensures that vertebral fastener 522 is securely attached to vertebral clamp 512, vertebral plate 510 and/or a vertebra. Lock 509 may also have any suitable dimension, configuration or geometric shape and may be fabricated from any suitable material. In an exemplary embodiment, lock 509 may be a threaded component, hook, latch, pin, nail, wire, tether, or combinations thereof.

Figure 19:
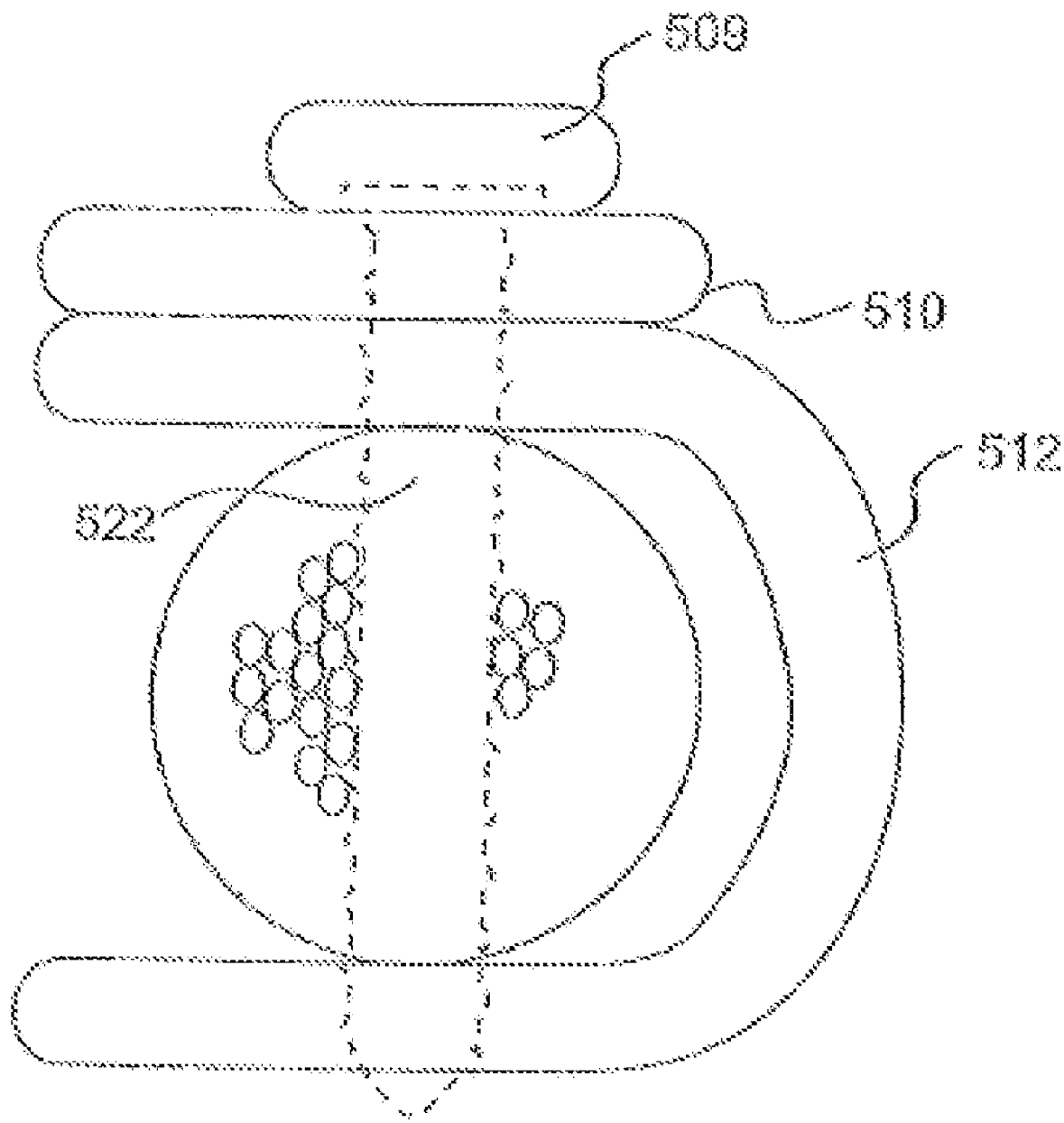
FIG. 19 is a cross section of a screw placed through the plate, the clamp, and posterior arch of the C1 vertebra that is secured with a spiral locking mechanism in the screw head.

In an exemplary embodiment, lock 509 may be threaded component, such as a screw, bolt, rivet, or nut. As shown in FIG. 19, lock 509 may be a nut coupled to the head of vertebral fastener 522. Vertebral fastener 522 may be secured by preventing it from being unscrewed or otherwise detached from vertebral clamp 512, vertebral plate 510 and/or a vertebra without first removing the nut. In one example, to remove the nut, it must be turned in the opposite direction in which a threaded vertebral fastener 522 must be turned to detach vertebral fastener 522.

As shown in FIGS. 18(a)-20, in one exemplary embodiment, vertebral fastener 522 may be a threaded component, such as a screw, rivet, or bolt. Preferably, vertebral fastener 522 may be a triple screw that possesses three functional portions along the length of the screw: a threaded portion for attachment to bone; a threaded or non-threaded portion to engage vertebral plate 510, and a threaded or non-threaded portion to engage vertebral clamp 512. Each portion may have a different diameter, a different sized threading, or different contour, different length, or combinations thereof that is customized to for the aforementioned functions. The triple screw may provide increased stability by virtue of the combined fixation of the screw within vertebral plate 510, vertebral clamp 512 and the vertebra. Triple screw 70 further includes a threaded portion at an upper portion thereof that is sized in pitch to mate with an internally threaded hexagonal nut 82 that may be used to retain another surgical instrument, such as a support rod 450, 452. For example, triple screw 70 may engage a support rod 450, 452 either by inserting the triple screw 70 through a hole defined in the body of support rod 450, 452 or by inserting the support rod 450, 452 through a hole 468 defined in the body of triple screw 70. In one embodiment, the hole 468 positioned in the triple screw 70 may be positioned below nut 82 and arranged in any body portion of the triple screw 70, preferably between the threaded portion for attachment to bone and the threaded portion for engaging with nut 82. The threaded component may have a small diameter, for example, about 1.5 mm to about 4 mm and a length of about 6 to about 20 mm. Vertebral fastener 522 may couple vertebral clamp 512 to a vertebra by penetrating a portion of a vertebra and vertebral clamp 512 at the dorsal and/or ventral apertures 508. Vertebral fastener 522 may also include a lock 509, such as a nut, that prevents loosening under applied physiological loads. In the exemplary embodiment shown in FIG. 18(a), the tip of vertebral fastener 522 does not extend substantially past ventral aperture 508 of vertebral clamp 512 so as to injure the vertebral artery, vertebral vein, spinal nerve roots and/or spinal cord.

Figure 18D:
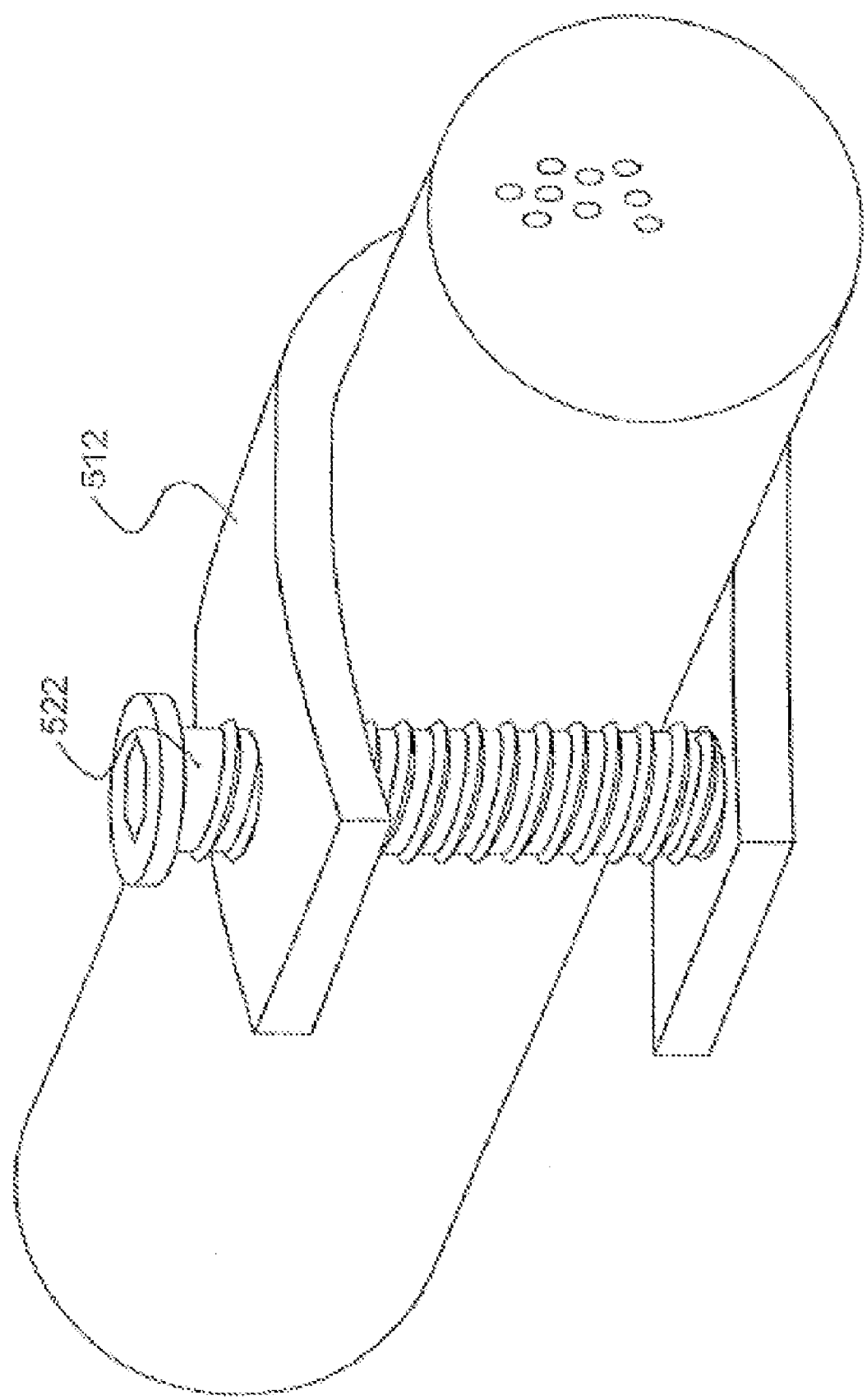
FIG. 18(d) is a perspective view of a screw placed through the clamp and adjacent to the posterior arch of the C1 vertebra.

In the alternative exemplary embodiment of FIG. 18(d), vertebral fastener 522 may be located adjacent to but does not penetrate the vertebra. In this embodiment, vertebral fastener 522 extends through vertebral clamp 512 at the dorsal and/or ventral apertures 508, and secures a vertebra by functioning as a clasp or latch, passing adjacent to the vertebra. Because vertebral fastener 522 does not penetrate the vertebral body, this embodiment minimizes trauma and vertebra erosion. When vertebral fastener 522 is a triple screw, the length of the screw that extends adjacent to the vertebral body may optionally be non-threaded in this embodiment. As discussed above, vertebral fastener 522 may also include a lock 509 to prevent loosening under applied physiological loads.

Figure 20:
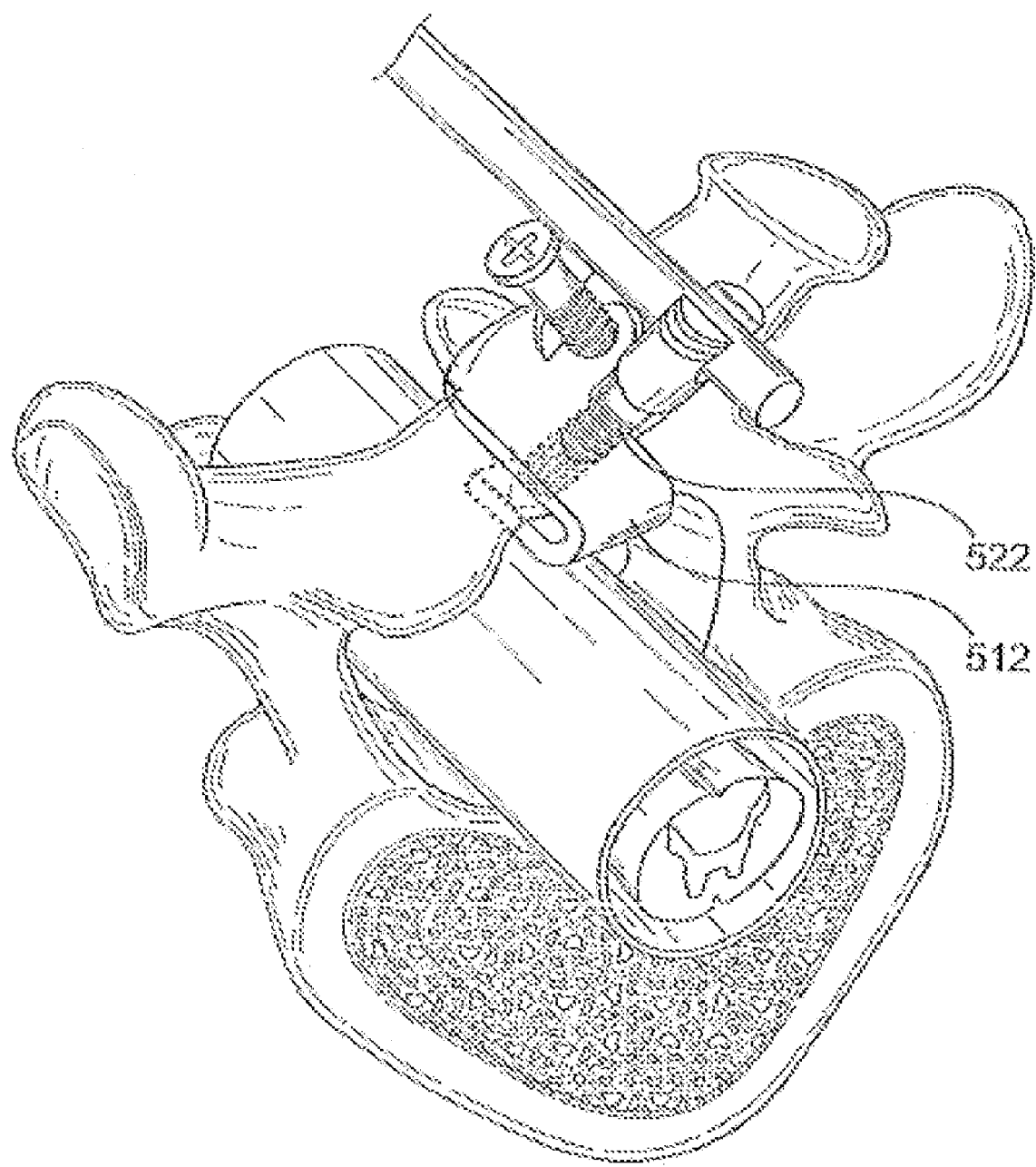
FIG. 20 is a perspective view of an exemplary attachment system wrapping around the spinous process of the thoracic vertebra using sublaminal screws.

Vertebral fastener 522 may be used to attach vertebral clamp 512 to any portion of a vertebra that would enable load bearing applications, such as spinal stabilization. In exemplary embodiment, vertebral clamp 512 and vertebral fastener 522 may be attached to a posterior region of a vertebra, preferably at a location sufficiently distanced from the vertebral artery, vertebral vein, spinal nerve roots, spinal cord or a combination thereof to minimize the risk of possibly severing, compressing, impinging, or otherwise injuring the aforementioned spinal components. In an exemplary embodiment, vertebral clamp 512 and vertebral fastener 522 may be attached to the posterior arch of the C1 vertebra. Vertebral clamp 512 and vertebral fastener 522 may also be attached to a posterior region, such as the spinous process, pedicle or lamina, of the lumbar vertebrae, thoracic vertebrae, sacrum vertebrae, or coccygeal vertebrae. FIG. 20 shows vertebral attachment system 500 attached to a posterior region of an upper level thoracic vertebra, wherein a translamina screw engages the spinal canal by penetrating the cancellous and/or cortical bone of a vertebra to secure vertebral attachment system 500. The same vertebral attachment system 500, with minor modifications, may be similarly located on any cervical, thoracic or lumbar vertebrae.

Figure 21A:
FIG. 21(a) is a top view of an exemplary embodiment of a plate.
Figure 21B:
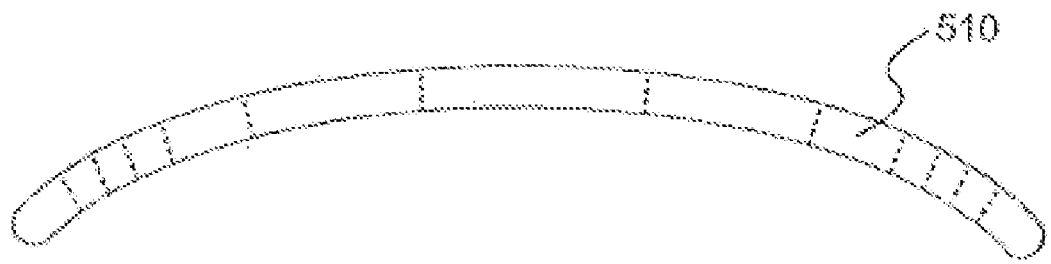
FIG. 21(b) is a side view of an exemplary embodiment of the plate shown in FIG. 21(a)

As shown in FIG. 21(a), vertebral attachment system 500 of the present invention may further include at least one modular vertebral plate 510 that may be attached to vertebral clamp 512 and a vertebra using vertebral fastener 522. Vertebral plate 510 functions as a scaffold that may be fastened to and stabilize one more other orthopedic structure, including spinal stabilization assemblies. Vertebral plate 510 may optionally be used to also position and bias a bone graft material, such as bone, a bone substitute or other non-osseous material, into close contact with and/or under pressure against, at least one vertebra so as to promote bone fusion.

Vertebral plate 510 may have any configuration, shape or dimension that may be compatible with vertebral clamp 512 and vertebral fastener 522 and that may enable load bearing applications, such as spinal stabilization. In an exemplary embodiment, the system may include a plurality of vertebral plates having different dimensions, configurations and sizes that may be customized to different vertebral regions or application. As shown in the exemplary embodiment of FIG. 21(b), vertebral plate 510 may be curved along a portion of its body that may correspond to the curved surface of the C1 vertebra's posterior arch. Preferably, vertebral plate 510 may be sized and/or shaped to complement a posterior region of a vertebra. As shown in FIG. 17, vertebral plate 510 may be a thin curved plate having at least one dimension that is approximately the same as that of a vertebra.

Vertebral plate 510 may also be elevated or extended to accommodate an enlarged vertebra caused by expansion duroplasty or an increased spinal canal size. In an exemplary embodiment, vertebral plate 510 may further include structure for adjusting a length of vertebral plate 510, whereby a lateral spacing distance between said first and second laterally spaced vertebral fastener 522 may be adjusted. In a preferred embodiment, this may be accomplished by constructing vertebral plate 510 out of two separate components that are attachable to each other, specifically a first connector portion 564 and a second connector portion 566, as is best shown in FIG. 16. The plurality of apertures 570, 572 in vertebral plate 510 may be used to adjust the first connector portion 564 relative to the second connector portion 566. A fastener 42 may be provided for securing the first connector portion 564 to the second connector portion 566 and is preferably applied centrally in a precise manner in order to stabilize the first and second connector portions 564, 566. Fastener 42 may be a threaded component, hook, latch, pin, nail, wire, tether, or combinations thereof. In an exemplary embodiment, fastener 42 is a threaded component, such as a rivet, bolt or screw, preferably a lock screw having a snap off head. A Vernier scale option may be used to generate the best precise fit, but other adaptations may be used, with the most important requirement being that a secure fit is created. Vertebral plate 510, including connector portions 564, 566 may be loaded with graft material and may be contoured or sized to accommodate the specific graft or implanted material size. In one possible alternative embodiment, the connector portions may be curved or may be straight with a rise to accommodate the anatomy of the vertebra and/or the application of any bone graft material.

Vertebral plate 510 may be coupled to a vertebra and vertebral clamp 512 any manner. In an exemplary embodiment, vertebral plate 510 may include one or more apertures 520 that may be compatible with vertebral fastener 522 and/or other orthopedic structures. Apertures 520 may be arranged in any manner along the body of vertebral plate 510. By incorporating a plurality of apertures 520 spread out along vertebral plate 510, vertebral attachment system 500 may support or connect to other vertebral attachment systems 500 and/or other orthopedic structures situated in various different locations. Additionally, apertures 520 may have a variety of different sizes and/or shapes so that vertebral plate 510 may be compatible with different vertebral fasteners 522 and/or orthopedic structures.

As shown in the exemplary embodiment of FIG. 17, vertebral plate 510 may be anchored to the vertebral lamina or the posterior arch of a C1 vertebra by inserting vertebral fastener 522 through aperture 520 of vertebral plate 510, a portion of a vertebra and the dorsal and/or ventral apertures 508 of vertebral clamp 512. Vertebral plate 510 may be located between vertebral clamp 512 and a vertebra. Alternatively, as shown in FIG. 19, vertebral clamp 512 may be located between vertebral plate 510 and a vertebra.

Vertebral plate 510 may be fabricated from any high strength and biocompatible material. In an exemplary embodiment, vertebral plate 510 may be fabricated from any material having sufficient material and mechanical properties for load bearing applications, such as spinal stabilization. The material used to fabricate vertebral plate 510 may include a biocompatiable metal, metal alloy, ceramic, polymer, such as a polymer from the polyaryl ether ketone family (PAEK) family, such as polyether ether ketone (PEEK) or polyether ketone ketone (PEKK), or composite material. Preferably, the material may include a metal alloy, such as stainless steel and/or titanium. Optionally, the surface of vertebral plate 510 may be treated to adjust the frictional, wear or biocompatibility properties of vertebral plate 510. In an exemplary embodiment, at least one portion of vertebral plate 510 may be coated with a material, shaped and/or textured to limit a range of motion of vertebral plate 510 relative to the vertebra and/or vertebral clamp 512. In another embodiment, vertebral plate 510 may be coated with a material to minimize wear of vertebral plate 510 and/or facilitate osteointegration.

Figure 22A:
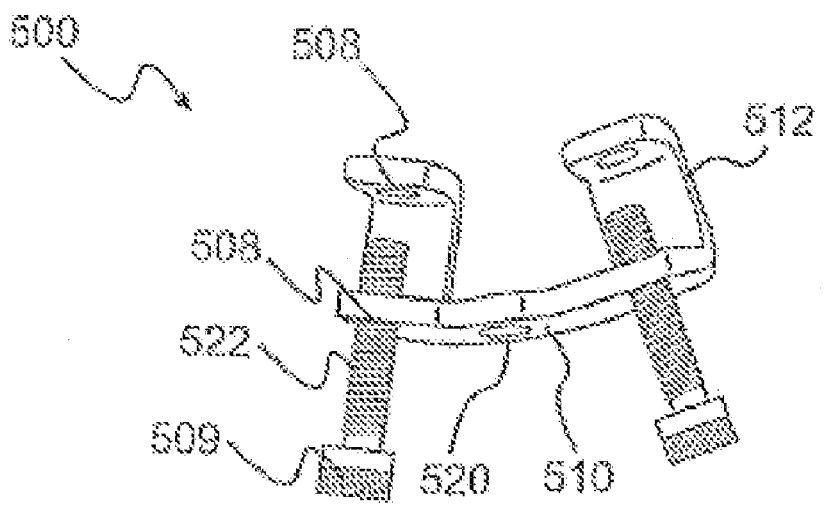
FIG. 22(a) is a perspective view of an attachment system wherein the clamps and plate are constructed as an integral device.
Figure 22A:
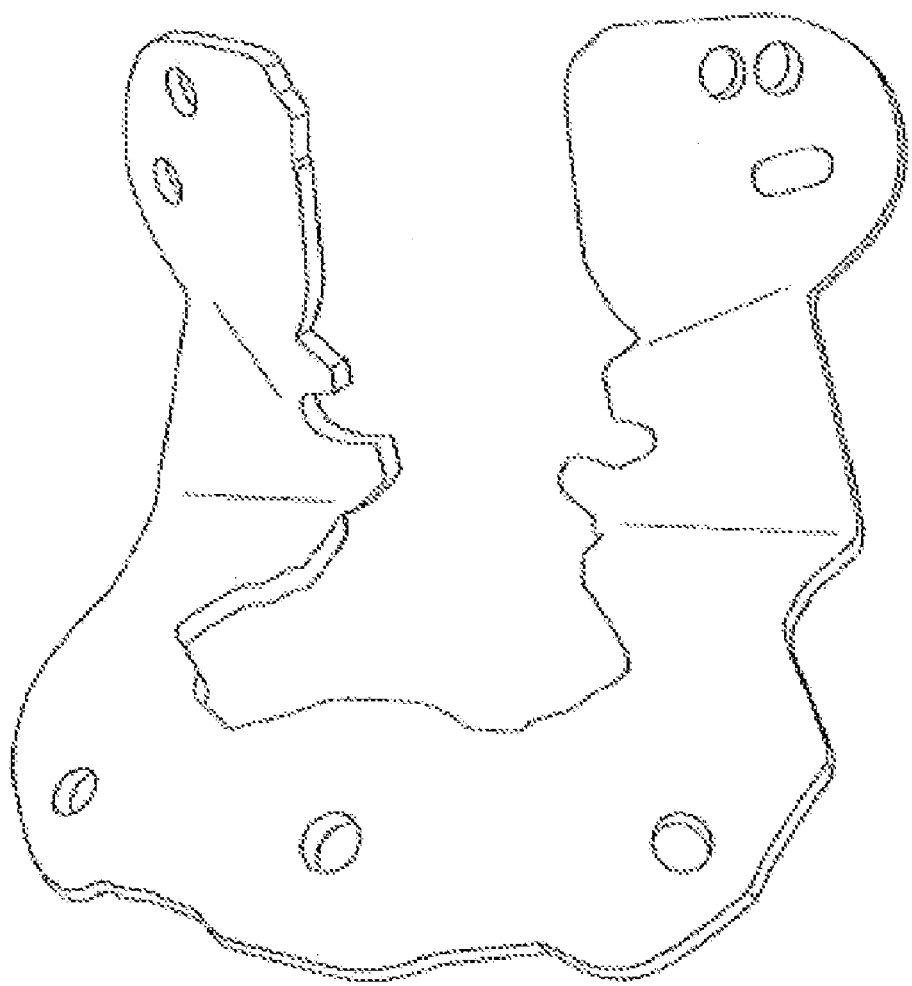
Figure 22B:
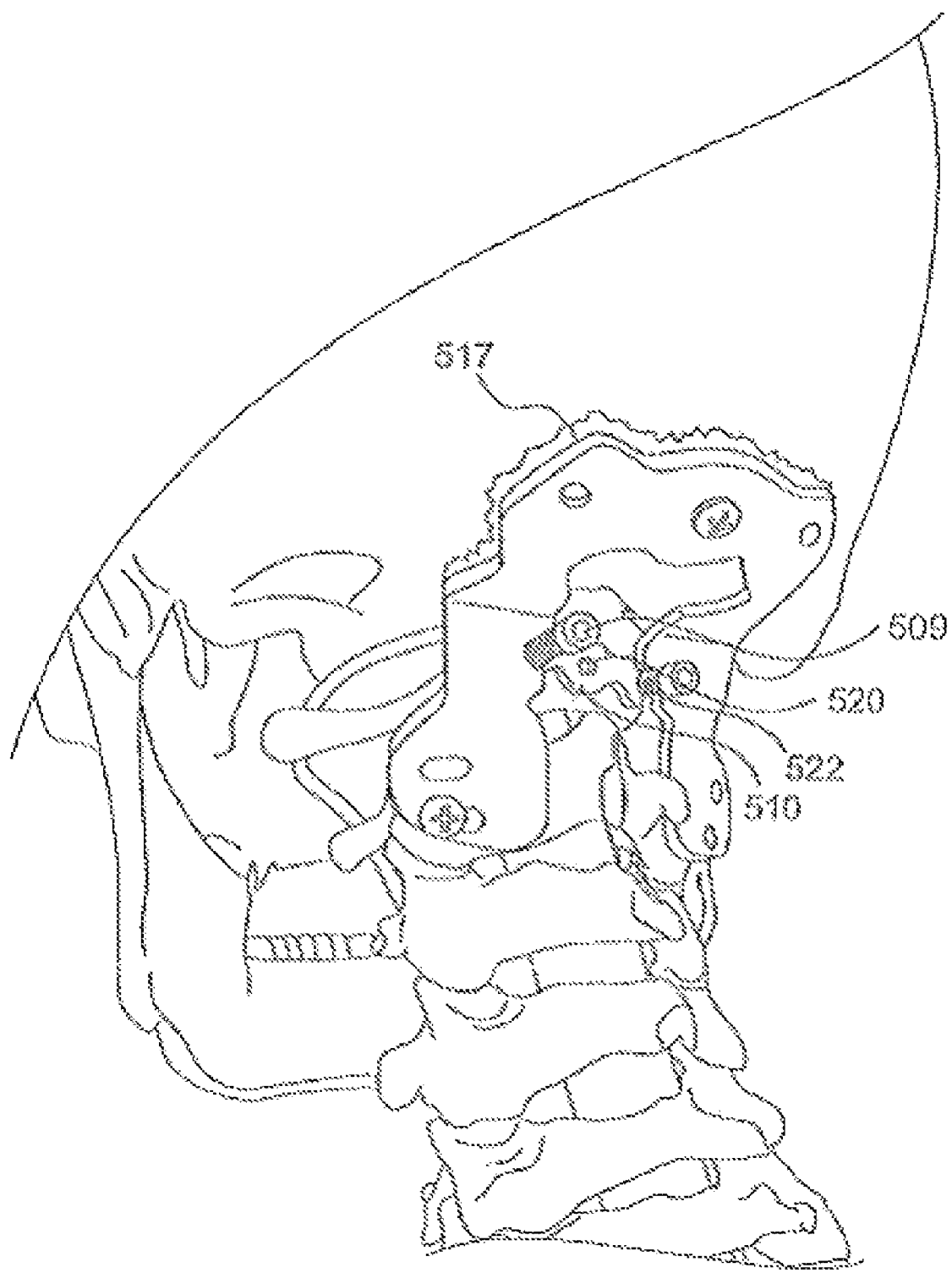
FIG. 22(b) is a perspective view of the attachment system of FIG. 21(a) fastened to an occiput plate.

The modular attachment system of the present invention may be operatively assembled and customized to enable a wide variety of applications and to create a custom fit for each patient. For example, the attachment system may include a combination of any number of vertebral clamps 512, vertebral fastener 522, vertebral plates 510, and connection system 400 having any of the above discussed configurations, shapes or dimensions. Vertebral clamp 512, vertebral plate 510 and vertebral fastener 522 of exemplary vertebral attachment system 500 may be assembled during surgery. Alternatively, as shown in another exemplary embodiment of vertebral attachment system 500 of FIGS. 22(a)-22(c), one or more vertebral clamp 512 and vertebral plate 510 may be prefabricated as an integral device and subsequently fastened to a vertebra using vertebral fastener 522 during surgery. Any orthopedic structure, such as a cranial and/or vertebral plate, may be fastened to the attachment system. FIGS. 22(b)-22(c) show an occipital plate anchored to a vertebral attachment system 500, enabling stabilization of the occipitocervical junction.

The attachment systems of the present invention provides numerous advantageous over spinal fixation systems of the prior art. Because the attachment system may be located on the posterior portion of any vertebra, such as the posterior arch of the C1 vertebra, it encumbers only the dorsal aspect of a vertebra where the major tension forces exerted during flexion of the neck occur, and where therefore, fusion is most retarded. Typically the posterior surface of the C1 vertebra is the least acceptable locus of fusion because of the high shear over the posterior surface in flexion, extension and rotation; the major loading/compression forces in extension occur on the cranial and caudal surfaces of the C1 vertebral arch, and these surfaces are more condoning of the fusion than the posterior surface of the posterior C1 ring. The attachment system is also advantageous because it may have a unique structural configuration that is: compatible with a posterior region of a vertebra, sufficiently thin to minimize the risk of neural or spinal cord compression, and/or does not significantly weaken the vertebra to which it is fastened. Additionally, because the attachment system may also be formulated as a modular kit including a plurality of vertebral clamps 512, vertebral fastener 522, vertebral plates 510 and connection system 400 of varying sizes and configurations, it may be customized for each application and/or patient. Furthermore, the attachment system provides an effective, fast and safe means for vertebra attachment. In addition to attaching to a vertebral surface, vertebral attachment system 500 may also be adapted for use in anchoring one or more surgical instruments to any anatomical surface, particularly any bone structure. Specifically, it is envisioned that vertebral attachment system 500 may be adapted to be attach to any cranial or craniospinal surface so as to be used in conjunction with spinal stabilization system 100 or other spinal stabilization system. Vertebral attachment system 500 may be used independent of spinal stabilization system 100. For example, vertebral attachment system 500 may be adapted to anchor one or more surgical instruments to a long bone.

Cranial Attachment System

Figure 23A:
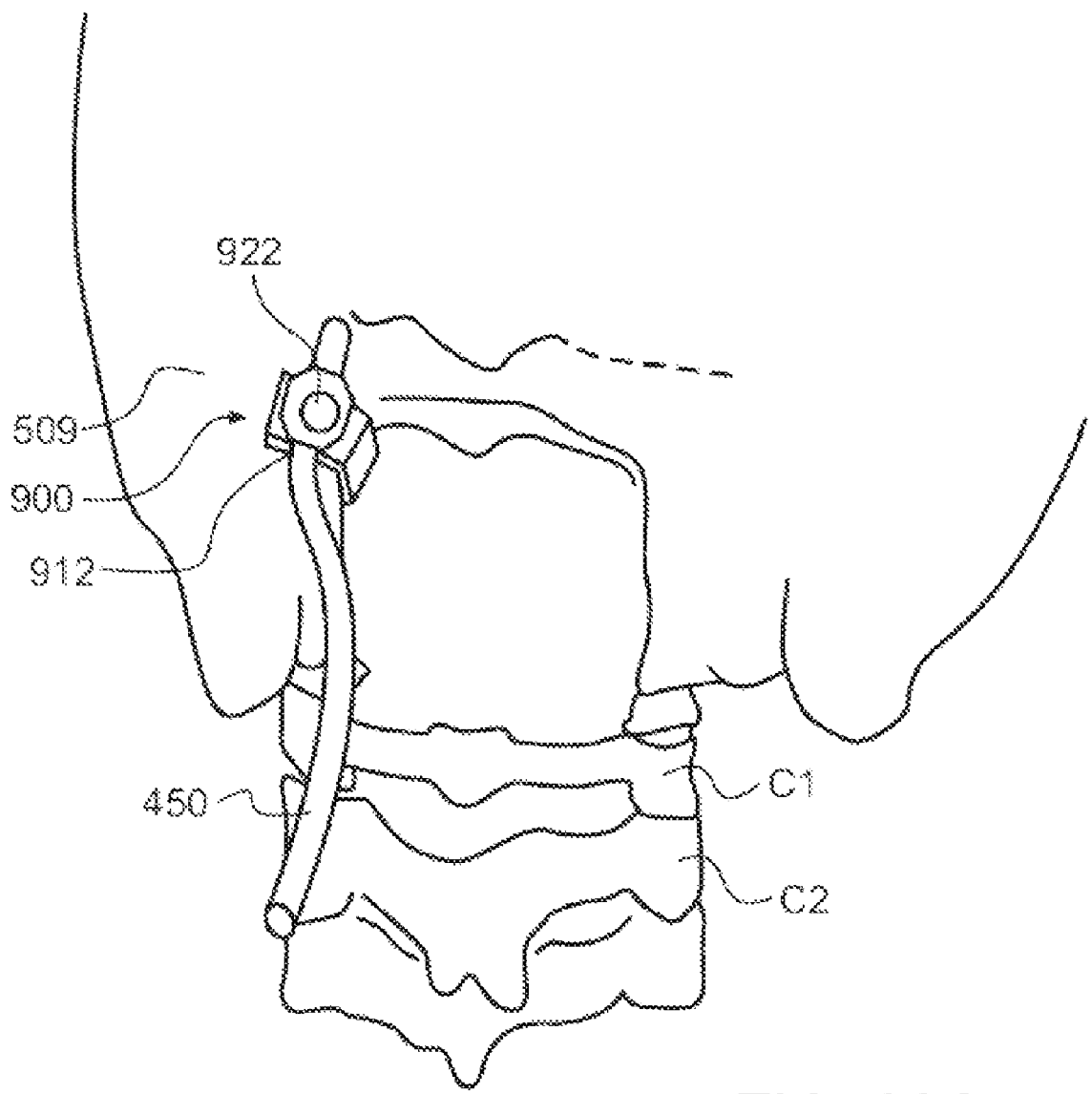
FIG. 23(a) shows a perspective view of an exemplary cranial attachment system positioned along a perimeter of a calvarial defect.
Figure 23B:
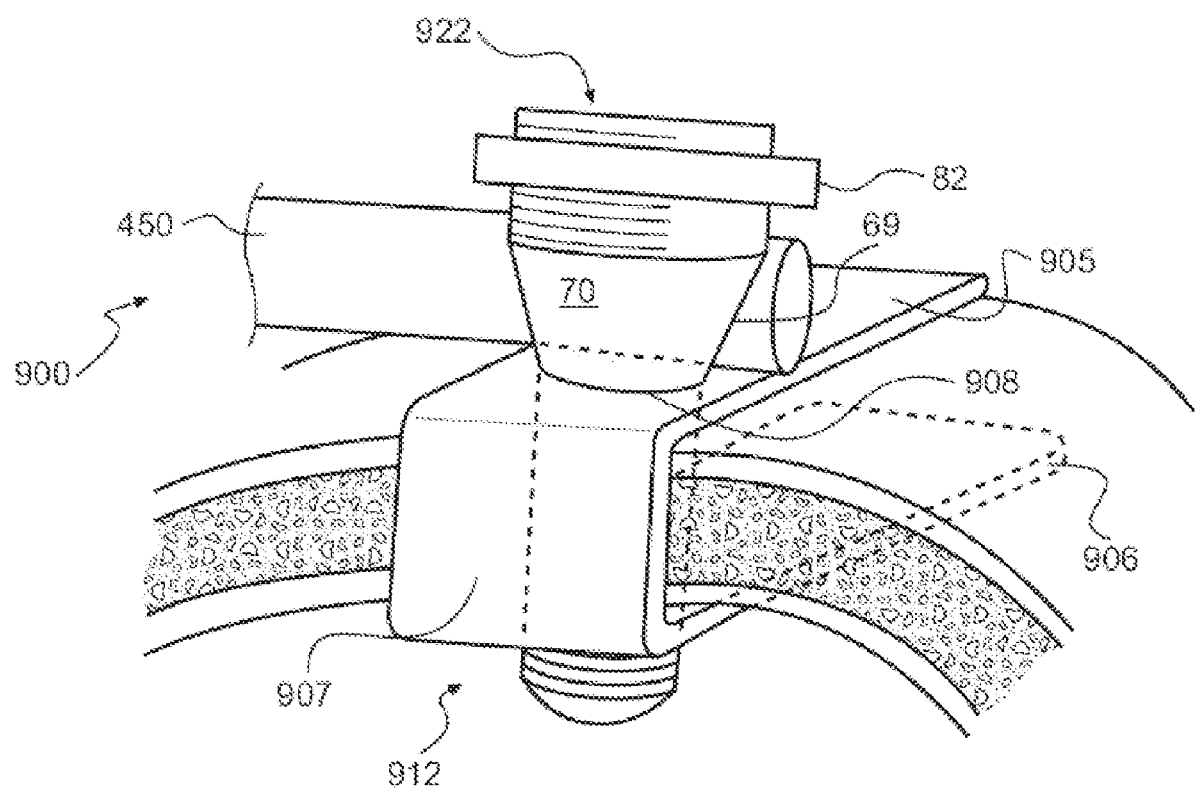
FIG. 23(b) shows a perspective view of the cranial attachment system of FIG. 22(a) enclosing an edge of the calvarial defect.
Figure 23C:
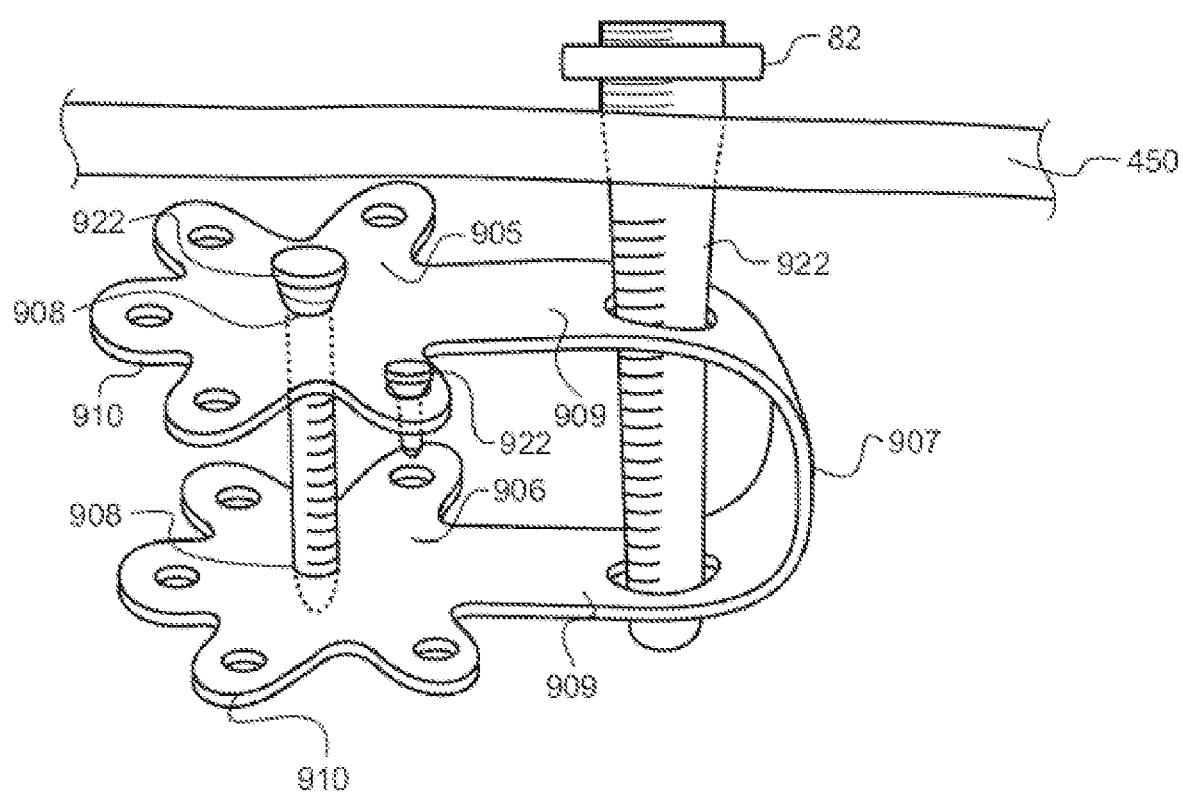
FIG. 23(c) shows an exemplary cranial clamp including a base member and a plurality of extension members.

Referring now to FIGS. 23(a)-23(c), spinal stabilization system 100 may further include a cranial attachment system 900 that connects one or more surgical instruments, such as one or more components of plates 300, osteointegration apparatuses 700, connection system 400 or combinations thereof, to a cranial bone, such as the occipital plate, occiput or calvarium. Using cranial attachment system 900, only a minimal amount of cranial bone is necessary to anchor the surgical instruments. Cranial stabilization system 900 therefore enables a surgeon to connect one or more surgical instruments to the cranium even when a substantial portion of the occipital plate has been removed due to a craniotomy or trauma. Cranial stabilization system 900 may be particularly suited to anchoring an upper end of one or more support rods 450 and/or plates 300 to the cranium after a suboccipital craniotomy has been performed.

As shown in FIGS. 23(a)-23(c), cranial stabilization system 900 may include at least one cranial clamp 912 configured to engage a cranial surface and at least one cranial fastener 922 that may be coupled with cranial clamp 912 and one or more surgical instruments, such as support rod 450, plate 300, flange 325, porous member 750 or frame member 760, which in turn may be connected to or otherwise operatively associated with other orthopedic structures. Intended to anchor one or more components of plate 300, osteointegration apparatus 700, connection system 400 or combinations thereof, cranial attachment system 900 is designed to withstand at least normal spinal loads. It is envisioned that the cranial attachment system of the present invention may also be compatible with other orthopedic structures or assemblies for enabling stabilization of the occipitocervical junction.

In one embodiment, cranial clamp 912 may have the same or similar structural configuration and material construction as clamping structures 552, 554 or vertebral clamp 512, preferably adapted to engage a cranial surface, and cranial fastener 922 may have the same or similar structural configuration and material construction screws 122 or fastener 522, preferably adapted for engaging a cranial surface. In another embodiment, cranial stabilization system 900 may have the same or similar structural components as the vertebral attachment system 500 that have been adapted for engaging and/or attaching to a cranial surface.

Cranial clamp 912 may have any structure capable of enclosing, surrounding and retaining an upper, lower and side surface of the cranium. In one embodiment, cranial clamp 912 surrounds an edge of a cranial surface, such as the lower edge of the occipital plate or a cranial edge defining a cranial defect. For example, cranial clamp 912 may surround and enclose an edge of a hole defined in the cranium caused by trauma, disease or surgical incision. Cranial clamp 912 may have any dimension, configuration or geometric shape suitable for gripping, clasping or otherwise retaining a portion of a cranial surface adjacent to a cranial edge. In one embodiment, cranial clamp 912 has at least two member portions, a first member 905 for engaging an upper surface of the cranial bone and a second member 906 for engaging a lower surface of a cranial bone that is spaced apart from first member 905. In one embodiment, first and second members 905, 906 are opposed and spaced parallel relative to one another. Alternatively, first and second members 905, 906 may form a V like configuration. First and second members 905, 906 may have any shape, dimension or configuration suitable for positioning and engaging a cranial bone therebetween. Exemplary configurations may include a discoid, rectangular, ovid, circular, square, star or triangular shape. To decrease the profile of cranial clamp 912, an exterior surface of first and second members 905, 906 is smooth, and a distal end thereof may be tapered so as to be thicker at a proximal end adjacent to a cranial edge and thinner at a distal end. As shown in FIG. 23(b), cranial clamp 912 has three member portions, a first and second member 905, 906 for engaging an upper and lower surface of a cranial bone, respectively and a third member 907 that abuts and engages the cranial edge and connects first and second members 905, 906. In one embodiment, at least one member of cranial clamp 912 conforms to a surface of a cranium, such as a curved upper surface, lower surface or side surface of a cranial edge. A proximal end of first and/or second members 905, 906 adjacent to the cranial edge or third member 907 may be about 10° to about 40°, preferably about 10° to about 30°. First and second members 905, 906 may have a length of about 5 mm to about 5 cm, preferably about 10 mm to about 15 mm and a width of about 3 mm to about 20 mm, preferably about 5 mm to about 20 mm, more preferably, about 3 mm to about 12 mm, and most preferably, about 10 mm to about 13 mm. First and second members 905, 906 may have a thickness of about 1 mm to about 9 mm, preferably, about 2.5 mm to about 5 mm. In one embodiment, third member 907 may have the same length, width and thickness dimensions. As shown in FIG. 23(b), cranial clamp 912 may have a U, semi-circular or collar like shape. In one embodiment, first, second and third members 905, 906 and 907 may have a low profile to avoid or minimize the occurrence of cranial deformities that may cause pain and discomfort to the patient.

In an alternative embodiment shown in FIG. 23(c), first and second members 905, 906 each have a base member 909 connected to a plurality of extension members 910 to enhance attachment to a cranial bone. One or more, preferably two or more, more preferably three or more, and most preferably five or more extension members 910 may be extend from base member 909 in a finger like configuration. In an exemplary embodiment, base member 909 and/or extension members 910 may have a discoid, rectangular, ovid, circular, square, star or triangular shape. In one embodiment, extension members 910 may have different sizes, shapes and dimensions. For example, two or more extension members 910 may have different lengths or direction and degrees of curvature to facilitate attachment to a cranial bone. In another embodiment, extension members 910 may be sufficiently malleable to enable a surgeon to movably arrange extension members 910 relative to one another to facilitate and customize attachment about a cranial edge.

One or more holes 908 may be defined in first member 905 and/or second member 906 for receiving cranial fastener 922. Preferably, one hole 908 centrally defined in a first member 905 may be aligned with another hole 908 centrally defined in second member 906. In one embodiment, cranial clamp 912 may include a plurality of holes 908 positioned at a distal end of extension members 910 as well as a central region of base member 909. Cranial clamp 912 may also include a plurality of holes 908 having a variety of different sizes and shapes to accommodate different cranial fasteners 922. The structure, contour and configuration of hole 908 may be the same as that of aperture 508.

Cranial attachment system 900 may include any number of cranial clamps 912 for attaching one or more surgical instruments to a cranial surface. In one embodiment, cranial attachment system 900 includes at least one or more cranial clamps 912 for connecting an upper end of each of support rods 450, 452 to a cranial surface. Preferably, the system may include at least about 1 to 6 cranial clamps 912, more preferably, about 2 to 4 cranial clamps 912. The cranial clamps 912 may be positioned equidistantly, symmetrically or asymmetrically along and about a perimeter of a cranial edge that defines a cranial defect, preferably at least two cranial clamps 912 may be arranged on opposing sides of a cranial defect. In one embodiment, one or more cranial clamps 912 may be arranged along a cranial edge that defines an upper end of the cranial defect.

As shown in FIGS. 23(a)-23(c), a cranial fastener 922 may removably secure cranial clamp 912 to a cranial surface and enable load bearing applications, such as spinal stabilization.

Cranial fastener 922 may be any fastener that is sized and configured to secure cranial clamp 912 as well as one or more surgical instruments to a cranial surface. In one embodiment, cranial fastener 922 may have the same structural components, configuration and material construction as vertebral fastener 522. Cranial attachment system 900 may also include a plurality of cranial fasteners 922 having the different configurations or dimensions that are compatible with holes 908 that may vary in size and shape. In an exemplary embodiment, cranial fastener 922 is configured as a screw, such as a set screw.

In an exemplary embodiment, cranial fastener 922 may be a triple screw 70 that possesses at least three functional portions along the length of the screw. The triple screw 70 may be inserted into a cranial bone, such as the occipital plate, occiput, or calvarium, such that a first threaded portion is positioned within and engages the intervening cranial bone. Alternatively, the triple screw 70 can pass through the cranial bone into second member 906 of cranial clamp 912, such that a first threaded portion engages both the intervening cranial bone and/or second member 906 of cranial clamp 912. A second threaded or non-threaded portion may engage first member 905 of cranial clamp 912. A third threaded or non-threaded portion may engage one or more surgical instruments. The triple screw may further include a top loading externally threaded portion for engaging with an internally threaded nut 82. Each portion may have a different diameter, a different sized threading, or different contour, different length, or combinations thereof that are customized for the aforementioned functions. In one embodiment, a hole 468 for receiving a support rod 450, 452 is defined in the body of triple screw 70 below the nut 82. The hole 468 may be arranged in any portion of the triple screw 70, preferably between the first threaded portion for attachment to bone and the threaded portion for engaging with a nut 82. In an alternative embodiment, a hole may be defined in support rods 450, 452 through which triple screw 70 may be inserted and coupled. The triple screw 70 may provide increased stability by virtue of the combined fixation of the screw to a surgical instrument, cranial clamp 912 and the cranium. In one embodiment, the threaded component may have a small diameter, for example, about 1.5 mm to about 4 mm and a length of about 6 to about 20 mm.

Cranial fastener 922 may couple cranial clamp 912 to a cranial surface by passing through a portion of the cranial bone as well as a ventral hole 908 defined in first member 905 and/or a dorsal hole 908 defined in second member 906. In one embodiment, the tip of cranial fastener 922 penetrates the cranial plate, dorsal hole 908 of second member 906 and ventral hole 908 of first member 905. In an alternative embodiment, the tip of cranial fastener 922 does not extend past or does not extend substantially past ventral hole 908 of second member 906 so as to minimize the risk of injuring the brain or spinal cord. Additionally, to prevent cranial fastener 922 from perforating the dura, the distal tip of cranial fastener 922 may be rounded so that it gently pushes away the underlying dura when implanted in the cranium. Additionally, the length of cranial fastener 922 may be about 1 cm or less to further prevent perforating the dura.

In a preferred embodiment, cranial clamp 912 of cranial attachment system 900 may be used in lieu of plate 300 to anchor support rods 450, 452 to a cranial bone. As cranial clamp 912 only requires a small cranial surface area to anchor a surgical instrument, such as support rods 450, 452, it may be particularly useful in circumstances wherein a large portion of the cranium has been removed. Additionally, cranial clamps 912 also enables a surgeon to more freely arrange and anchor support rods 450, 452 to a cranial surface than would be possible using a conventional cranial fixation plate. To lower the profile of the cranial attachment system 900, cranial fastener 922 may be recessed within cranial clamp 912, and a support rod 450 may be connected to an exterior surface of cranial clamp 912, including an exterior surface of members 905, 906, 907 or combinations thereof, forming a monolithic plate. As shown in FIG. 7(a)-7(b), articulating rods are integrally formed with an exterior surface of third member 907.

In an alternative embodiment, cranial attachment system 900 may be operatively associated with a plate 300 and/or osteointegration apparatus 700 as well as support rods 450, 452. For example, plate 300 may be anchored to a cranial surface by inserting cranial fastener 922 through one or more apertures 336, 338, 340, 344, 346 of plate 300, through the dorsal and/or ventral holes 908 of first and second members 905, 906 of cranial clamp 912 and into a portion of the cranial bone. Plate 300 may be seated between an upper surface of first cranial clamp member 905 and the upper distal end of cranial fastener 922 so that cranial clamp 912 is positioned between the cranium and plate 300. Alternatively, plate 300 may be positioned between first member 905 of cranial clamp 912 and the cranium. In another embodiment, cranial clamp 912 and cranial fastener 922 may be indirectly attached to a plate 300 and/or osteointegration apparatus 700. For example, plate 300 and/or osteointegration apparatus 700 may be attached to the support rods 450, 452 at one location, and support rods 450, 452 may be attached to cranial fastener 922 at another location. Similarly, plate 300 and/or osteointegration apparatus 700 may be directly attached to cranial fastener 922 and indirectly attached to the support rods 450, 452.

The modular cranial attachment system of the present invention may be operatively assembled and customized to enable a wide variety of applications and to create a custom fit for each patient. For example, cranial clamp 912, cranial fastener 922 and one or more surgical instrument, such as plate 300 and/or support rod 450, 452, may be assembled during surgery. Alternatively, one or more cranial clamps 912 and surgical instruments may be prefabricated as an integral device and subsequently fastened to a cranial surface using cranial fastener 922 during surgery.

Cranial attachment system 900 offers numerous advantages over conventional cranial fixation systems of the prior art. Whereas conventional cranial attachment devices are dependent upon the amount of bone for anchoring, width of the craniotomy defect and thickness of the overlying scape toward the midline, cranial attachment system 900 can engage and be positioned in multiple sites around a craniotomy defect, is not limited by bone (calvarial) thickness, and may be rapidly and safely implanted. Furthermore, cranial attachment system 900 has a low profile designed to minimize pain and discomfort.

In addition to attaching to a cranial surface, cranial attachment system 900 may also be adapted for use in anchoring one or more surgical instruments to any anatomical surface, particularly any bone structure. Specifically, it is envisioned that the cranial attachment system 900 may be adapted to be attach to any vertebral or craniospinal surface so as to be used in conjunction with spinal stabilization system 100 or other spinal stabilization system. Cranial attachment system 900 may be used independent of spinal stabilization system 100. For example, cranial attachment system 900 may be adapted to anchor one or more surgical instruments to a long bone.

Trans-Vertebral Stabilization System

In an exemplary embodiment, spinal stabilization system 100 may further include a trans-vertebral stabilization system

600 that may function to facilitate and enhance fixation of the connection system 400 and/or vertebral attachment system 500. The trans-vertebral stabilization system 600 may be designed to enhance fixation of a vertebral implant by anchoring the implant in a direction substantially orthogonal to the implant pull-out force. In an exemplary embodiment, trans-vertebral stabilization system 600 may comprise one or more connectors 601 and one or more connector assemblies 602. The trans-vertebral stabilization system 600 of the present invention may be used in association with any spinal stabilization system, including spinal stabilization system 100 of the present invention.

The connector 601 of the trans-vertebral stabilization system 600 may be any structure having a shape, configuration, size and texture adapted for vertebral coupling and capable of resisting an implant pull-out force. The connector 601 may have an elongate cylindrical or rectangular body 603, such as a rod or plate, that spans a length of the vertebra and cooperates with one or more components of spinal stabilization system 100. In an exemplary embodiment, the connector body 603 may have a length of about 15 mm to about 50 mm, preferably about 25 mm to about 40 mm, and most preferably, about 30 mm to about 35 mm. Body 603 may have a low profile and a smooth surface area to minimize wear and inflammation. Portions of connector 601 may also be threaded, ribbed or include other mating features to facilitate coupling with the connector assembly 602, enable penetration of or anchoring to a vertebra and/or facilitate osteointegration with a vertebra. In an exemplary embodiment, connector 601 may be splined, so as to include grooves or other contours in the surface of the connector 601 to facilitate vertebral fixation. Connector 601 may be fabricated from any biocompatible material having a compressive strength and elastic modulus capable of resisting or withstanding the pull-out force of a vertebral implant. Exemplary materials may include titanium, composite metals, carbon fibers, PEEK or a combination thereof.

Figure 24A:
FIG. 24(a) shows an exemplary embodiment of a connector.
Figure 24B:
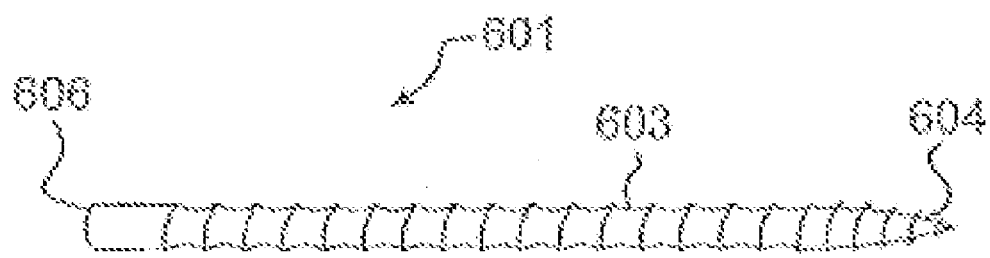
FIG. 24(b) shows another exemplary embodiment of a connector.
Figure 24C:
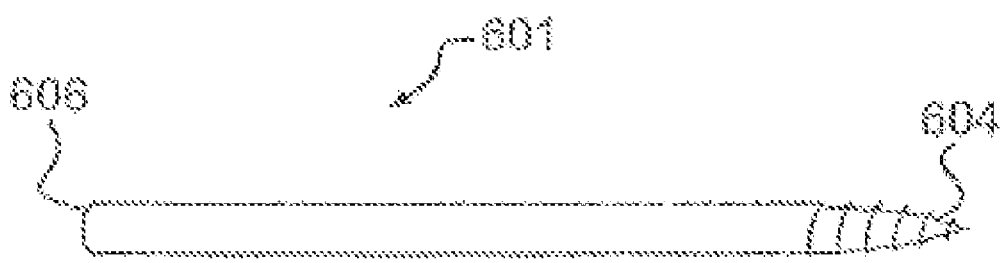
FIG. 24(c) shows a third exemplary embodiment of a connector.

In the exemplary embodiment of FIGS. 24(*a*)-24(*c*), connector 601 may be a rod that penetrates a portion of the vertebral body, such as the spinous process or lamina. The rod may include a distal end 604 that tapers to a point. The distal end 604 and/or at least a substantial length of the rod may be threaded to facilitate penetration and/or passage into the vertebra. A notch 605 may be located adjacent to the distal end 604. After the rod is inserted into the vertebra, a concentrated force may be applied to notch 605 to break distal end 604 from the rod. A proximal end 606, distal end 604, and portion of the rod adjacent to distal end 604 may be blunted, smooth, splined, threaded or may include mating features to facilitate engagement with one or more connector assemblies 602.

Figure 25A:
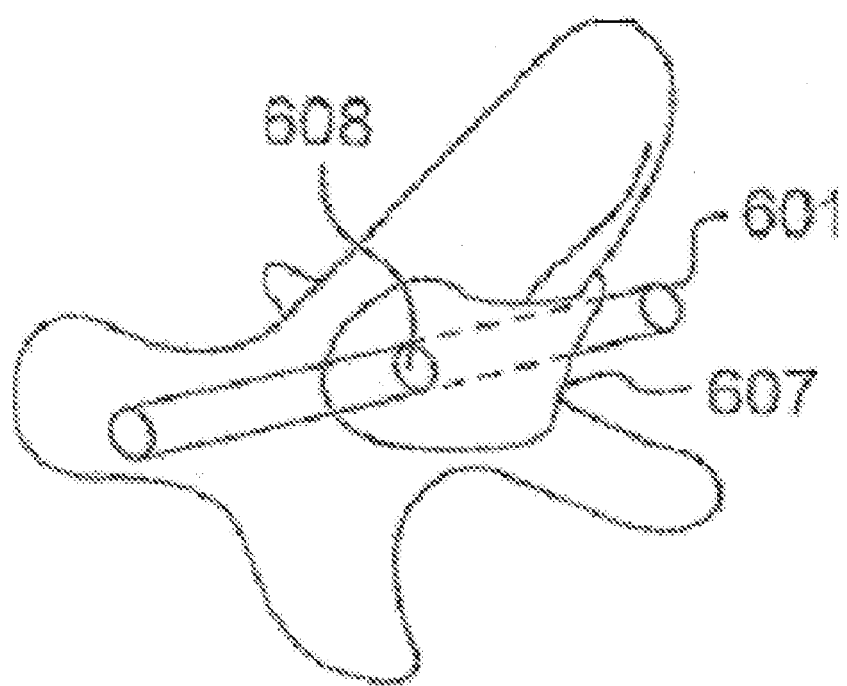
FIG. 25(a) shows a guide plate in conjunction with a connector.
Figure 25B:
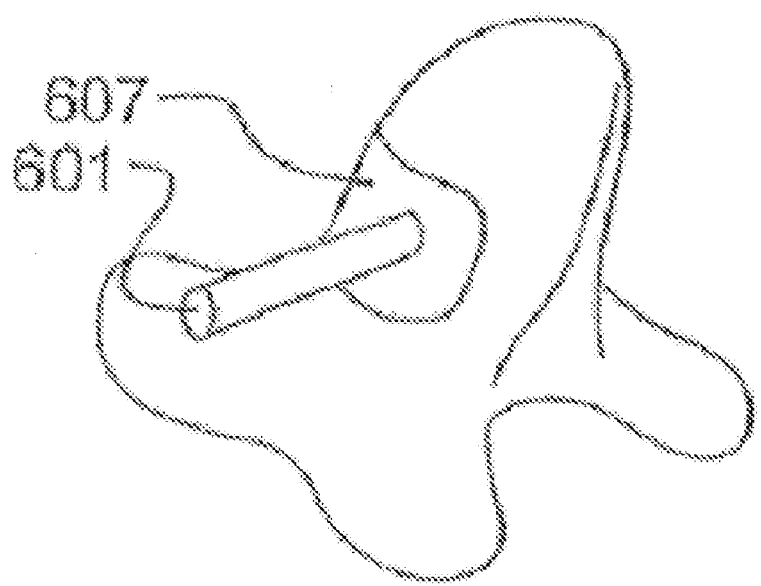
FIG. 25(b) shows another view of the guide plate in conjunction with a connector.
Figure 26:
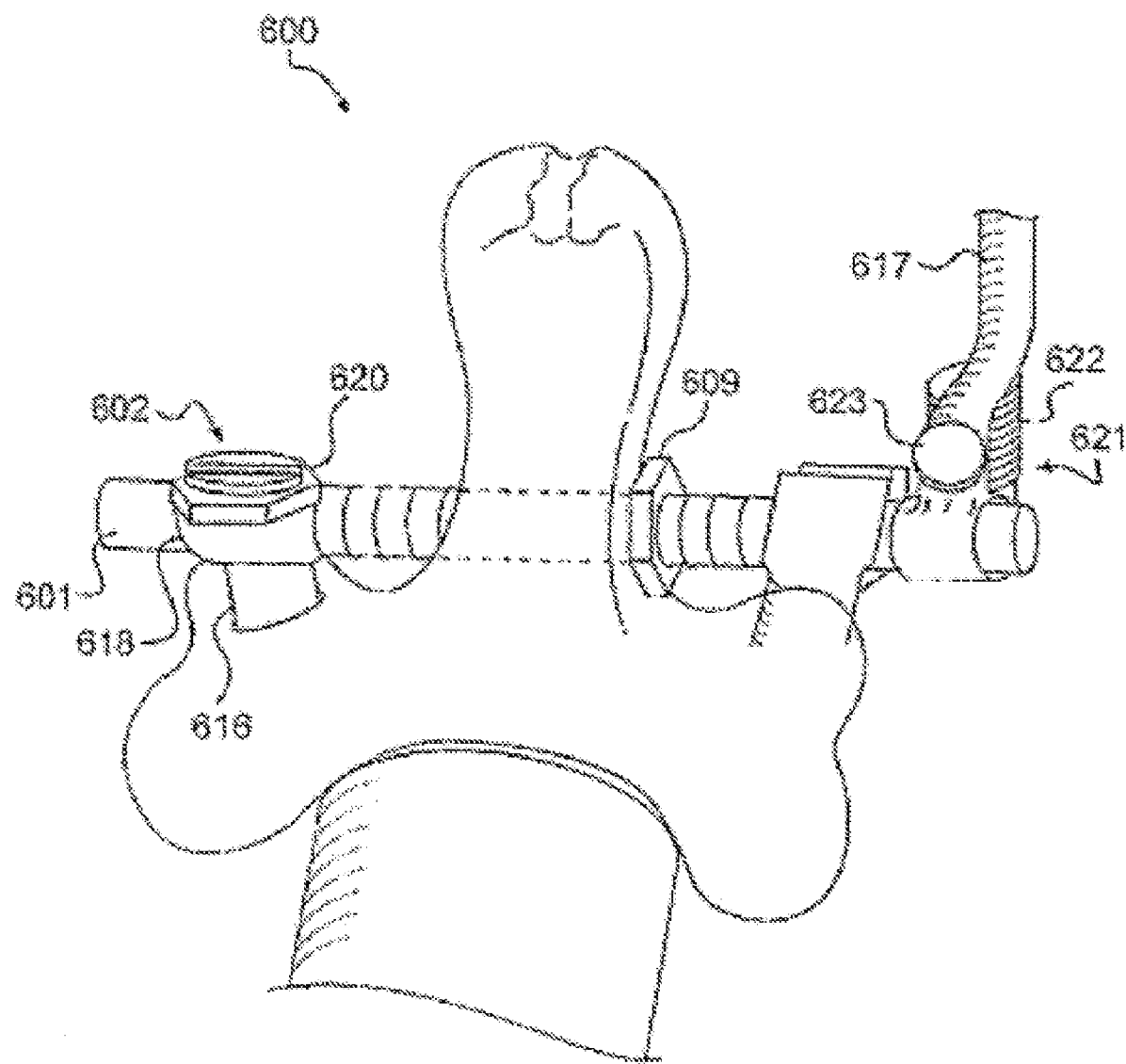
FIG. 26 shows a dorsal inferior view of the transvertebral stabilization system including a connector, two connector assemblies and a system fastener.

Optionally, as shown in FIGS. 25(*a*)-25(*b*), a guide plate 607 may surround the portion of the vertebra penetrated by the connector 601. Guide plate 607 may include apertures 608 arranged to position, receive and support connector 601. Guide plate 607 may function to provide structural reinforcement to and further anchor spinal stabilization system 100 to the vertebra. As shown in FIG. 26, alternatively or in addition to guide plate 607, one or more washers 609 may be positioned adjacent to the point where connector 601 penetrates and exits the vertebra. In an exemplary embodiment, washers 609 may have a shape that conforms to a portion of the vertebral surface. A locking mechanism 610, such as a nut, may be fastened to the washer to prevent loosening or movement of the connector 601 relative to the vertebra.

Figure 27:
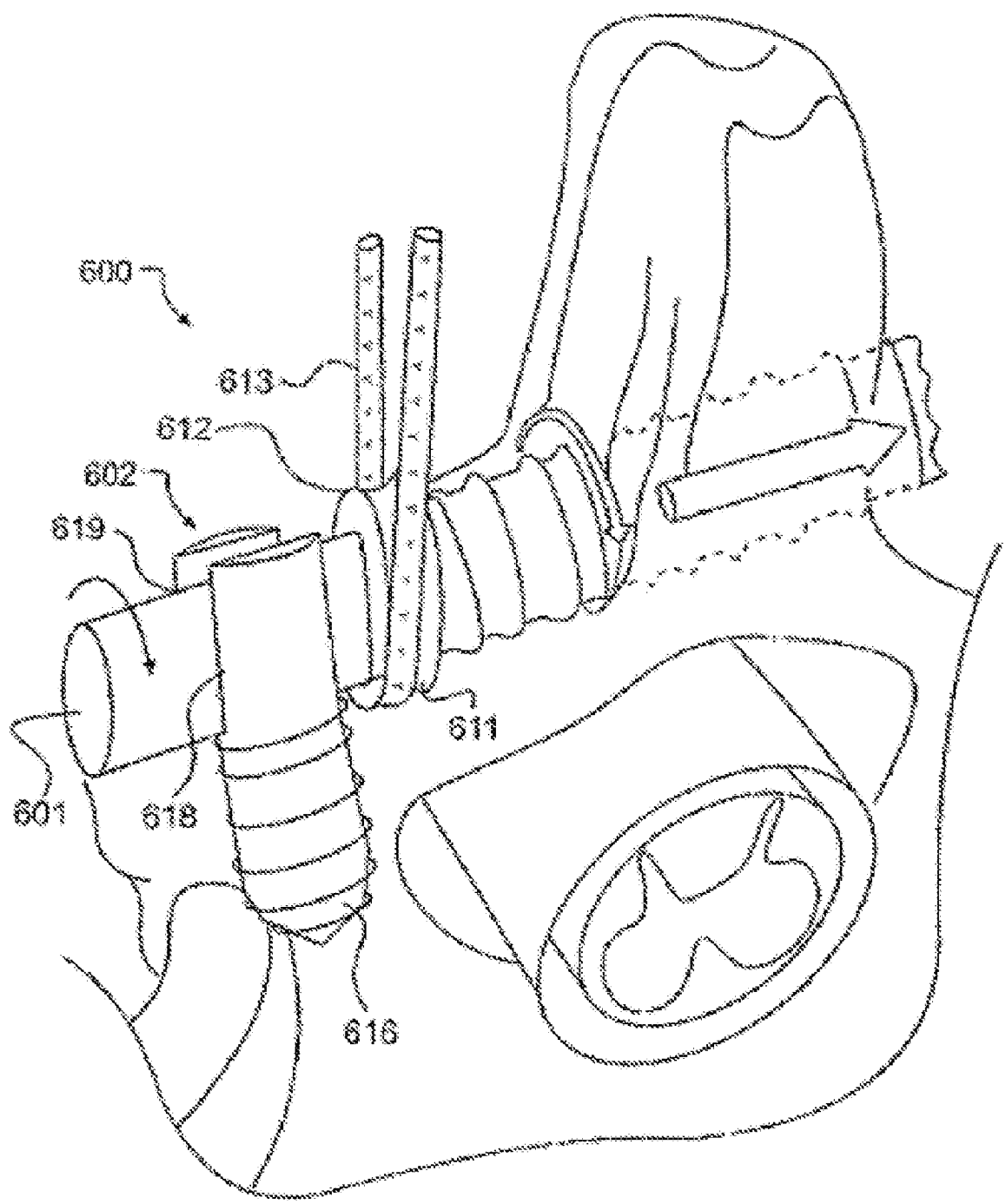
FIG. 27 shows an exemplary embodiment of a connector with a sprocket drive.

As shown in FIG. 27, connector 601 may further include an integral or removably attached sprocket 611. Sprocket 611 may include a plurality of protrusions, grooves, indentations, notches or combinations thereof. These structures may correspond to a plurality of mating elements 612 located on a cable, cord, chain or other gearing mechanism 613. A motor 614 or other mechanical means may be used to drive gearing mechanism 613 and rotate connector 601. The rotational driving force applied to connector 601 may be used to penetrate and create a hole through a portion of the vertebra.

Figure 28:
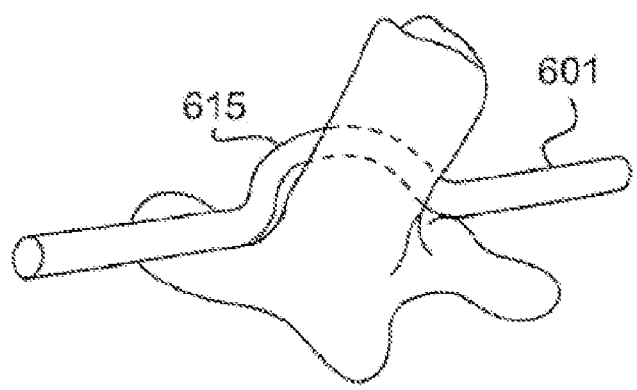
FIG. 28 shows an exemplary embodiment of a connector that does not penetrate the spinous process.

In the alternative embodiment shown in FIG. 28, the connector 601 may be a rod or plate that substantially conforms to and abuts a portion of the vertebra but does not penetrate the vertebra. Connector 601 may be configured so as to curve around a portion of the vertebra, such as the spinous process or lamina, which functions to anchor and further stabilize a vertebral implant or spinal stabilization system relative to the vertebra. The curved portion 615 of connector 601 may abut a portion of the vertebra that provides a resistive force substantially orthogonal to the anteriorly positioned connector assemblies 602. In this embodiment, the body of connector 601 may have a low profile thickness with a substantially smooth and continuous surface. Portions of the rod or plate may be threaded or may include mating features that facilitate coupling with the connector assemblies 602.

In general, connector 601 may be positioned relatively or substantially orthogonal to the pull-out force direction of a vertebral implant or pull-out force direction of connector assembly 602. In one exemplary embodiment, connector 601 may be positioned between about 45° to about 135° relative to the direction of the pull-out force or a connecter assembly 602. For vertebral implants or spinal stabilization systems 100 fixed in an anterior direction, as shown in FIGS. 26-27, connector 601 of the present invention may be substantially orthogonally oriented relative to the fixation means of the vertebral implant so as to anchor and enhance stabilization. Because connector 601 is positioned substantially orthogonal to the direction of fixation and/or pull-out force of the vertebral implant, spinal stabilization system 100 and/or connector assembly 602, the invention increases the stability of plates and screws in the posterior region of the spine. Furthermore, trans-vertebral stabilization system 600 opposes rotational, medio-lateral bending or distractive tendency, thereby greatly enhancing the overall stability of the vertebral implant and spinal stabilization system 100. Stability is further enhanced because rigid fixation of connector 601 within the spinous process and contralateral screw coupling opposes superoinferior bending and movement. Because the present invention is able to successfully mitigate and/or counter non-orthogonal stresses and reduce the overall pull-out forces exerted on any given screw or fixation means, it is possible to use a wide variety of fixations means of different caliber and still maintain stabilization. For example, it may be possible to utilize screws having lower compressive strength, smaller diameters, shorter lengths, fewer threads, less prominent threads or a combination thereof while still ensuring spinal stabilization.

As shown in FIGS. 26-27, connector 601 may be unilaterally or bilaterally coupled to one or more connector assemblies 602 of a spinal stabilization system 100. In the exemplary embodiments of FIG. 28, the connector assembly 602 may include at least one fastener 616, such as a threaded component, hook, latch, pin, nail, wire, tether, or combinations thereof that may function as part of spinal stabilization system 100; preferably, fastener 616 may be a threaded component, such as a screw, rivet or bolt. Fastener 616 may be a triple screw which possesses three functional portions along the length of the screw: a threaded portion for attachment to bone; a threaded or non-threaded portion to engage connector 601, and a threaded or non-threaded portion to engage a system connector 617.

Figure 29A:
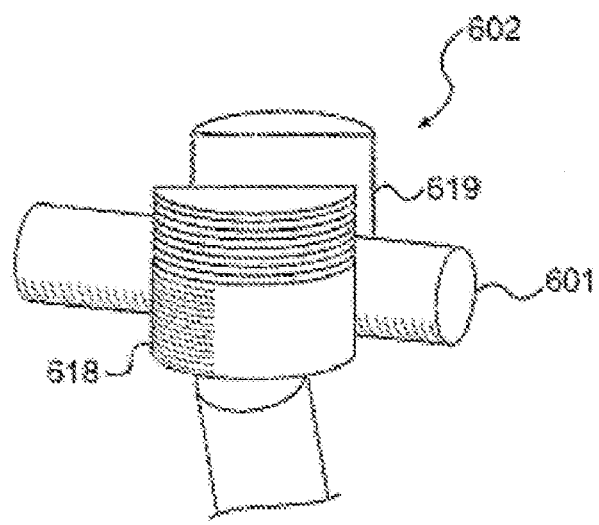
FIG. 29(a) shows an exemplary embodiment of the post of the connector assembly.
Figure 29B:
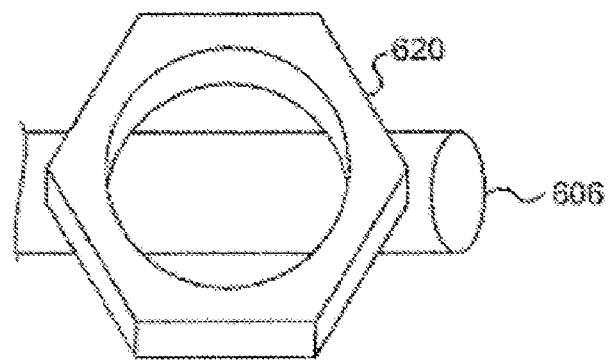
FIG. 29(b) shows an exemplary embodiment of the cap of the connector assembly.

Fastener 616 may include a post 618 having one or more slots 619 for receiving connector 601 and/or system connectors 617. The device may be modular, wherein post 618 may include one or more slots 617 for retaining connector 601. The slots 619 may have different sizes and/or shapes and may also be oriented in different directions relative to one another to accommodate different fasteners 616 and to enable a wide variety of applications. As shown in FIGS. 29(*a*)-29(*b*), the walls of post 618 which form slot 619 may have a threaded outer surface which can be coupled to a cap 620, such as a nut or top loading screw, for securing connector 601 within the slot 619. Alternative embodiments may include a non-polyaxial head or a splined portion that fits within post 618 for a tighter fit.

In an exemplary embodiment, connector assembly 602 may further be coupled to a system connector 617, which may be used to couple one or more components of stabilization systems 100 to each other and/or to other orthopedic structures anchored to different regions of the spinal column or cranium. In an exemplary embodiment, system connector 617 may be a component of connection system 400, such as a support rod 450, 452. As shown in FIG. 26, connector assembly 602 may attach connector 601 to a system connector 617, such as a lateral mass rod. The lateral mass rod may be attached to a vertebra above and/or below the vertebra coupled to connector 601. In an exemplary embodiment, system connector 617 may be angled and/or contoured to enable connection with orthopedic structures located at different positions. Additionally, system connector 617 may be oriented, angled, or contoured to minimize or eliminate injuries, such as ventral brainstem compression. System connector 617 may also include an optional pre-established rise option to accommodate the non-linearity of the level of the posterior arch of the cervical vertebrae relative to other orthopedic structures and/or other anatomical surfaces. System connector 617 may be secured within one or a plurality of slot 619 in post 618 using cap 620.

In the alternative embodiment shown in FIG. 26, system connector 617 may also be separate from connector assembly 602. In this embodiment, system connector 617 may still be attached to connector 601 using a system fastener 621. In an exemplary embodiment, system fastener 621 may be a flexible fitting or sleeve that fits around connector 601. System fastener 621 may be removably or integrally fitted and tightened about a portion of connector 601 and may be tightened with a turn screw or nut. In another embodiment, system fastener 621 may also be integral with connector 601 and/or connector assembly 602. System fastener 621 may include a fixed screw head or a flexible polyaxial screw head that would enable fixation of a screw, rod or other spinal stabilization device in a wide variety of orientations. In another embodiment, system fastener 621 may be coupled to a lateral mass screw or pedicle screw. System fastener 621 may further include a system post 622 having a system slot 623 for receiving system connector 617. A system lock 624 may secure system fastener 621 within system slot 623.

Connector assembly 602 may be constructed from any high strength and biocompatible material. In an exemplary embodiment, connector assembly 602 may be fabricated from any material having sufficient material and mechanical properties that would enable load bearing applications, such as spinal stabilization. The material used to fabricate connector assembly 602 may include a bio-compatible metal, metal alloy, ceramic, polymer, such as a polymer from the polyaryl ether ketone family (PAEK) family, such as polyether ether ketone (PEEK) or polyether ketone ketone (PEKK), or composite material. Preferably, the material may include a metal alloy, such as stainless steel and/or titanium. Optionally, the surface of connector assembly 602 may be treated to adjust the frictional, wear or biocompatibility properties of connector assembly 602. In an exemplary embodiment, at least one portion of connector assembly 602 may be coated with a material, shaped and/or textured to limit a range of motion of connector assembly 602 relative to connector 601. In another embodiment, connector assembly 602 may be coated with a material to minimize wear and/or facilitate osteointegration.

An osteogenic bone graft material may be applied to the junctions between stabilization system 100, the vertebral body and/or system connector 617 to facilitate bone fusion. In an exemplary embodiment, osteogenic material may include, without limitation, autograft, allograft, xenograft, demineralized bone, synthetic and natural bone graft substitutes, such as bio-ceramics and polymers, and osteo-inductive factors. In an exemplary embodiment, osteogenic material may include a bone morphogenetic protein (BMP), transforming growth factor β1, insulin-like growth factor, platelet-derived growth factor, fibroblast growth factor, LIM mineralization protein (LMP), and combinations thereof or other therapeutic or infection resistant agents, separately or held within a suitable carrier material. Additionally, osteogenic material may also be applied partially along or completely cover any surface of connector 601, connector assembly 602 and/or any other orthopedic structure to which stabilization system 100 is directly or indirectly connected to promote osteoblast generation and facilitate bone fusion. The bone graft material may be placed above, below or on any surface of stabilization system 100 as well as on any corresponding orthopedic structure. In an exemplary embodiment, connector 602 may be a scaffold coated and/or impregnated with osteogenic bone graft material, the structure of which may be naturally replaced with bone over time.

The trans-vertebral stabilization system 600 of the present application may be useful for a wide variety of applications to facilitate and enhance spinal stabilization by anchoring a vertebral implant in a direction substantially orthogonal to the pull-out force. In particular, it is envisioned that the invention may be particularly useful where a C2 pedicle is too narrow to receive a screw or where an encroaching vertebral artery prohibits placement of a transarticular screw through the facet joint or a lateral mass. Furthermore, trans-vertebral stabilization system 600 may be used in association with any stabilization system or vertebral implant to enhance stabilization and prevent loosening of vertebral implants and/or spinal stabilization systems 100 in the cervical, thoracic, lumbar and sacral levels.

Osteointegration Apparatus

Spinal stabilization system 100 may further include an osteointegration apparatus 700 that promotes bone fusion. Osteointegration apparatus 700 may have any shape, size or configuration suitable for a wide variety of applications involving tissue adhesion and/or fusion. The osteointegration apparatus 700 may also provide attachment to soft tissue, such as muscles, tendons and ligaments. In an exemplary embodiment, the apparatus may be particularly suitable for facilitating bone fusion, particularly with vertebrae, cranial bones, facial bones, teeth, or other parts of the appendicular skeleton.

When used as a component of spinal stabilization system 100, osteointegration apparatus 700 may function to facilitate fixation between one or more vertebrae and/or the cranium in order to enhance stabilization or normalization of the craniospinal junction. In the exemplary embodiment of FIGS. 30(a)-30(b), osteointegration apparatus 700 may be positioned over a portion of spinal stabilization system 100, such as plate 300, flange 325, and/or vertebra attachment 100, and/or one or more biological tissues, such as a bone surface, to assist fixation and bone fusion. By enhancing spinal fusion, the osteointegration apparatus 700 may obviate the need for using deeply penetrating screws during spinal stabilization, thereby decreasing the risk of injuring sensitive regions of the anatomy, including the vertebral artery, brainstem or nerve roots. The device is also advantageous in that it can be quickly applied, minimizing the time required to perform a surgical procedure and may be inserted through a small incision, thereby minimizing surgical exposure and risk.

Figure 30A:
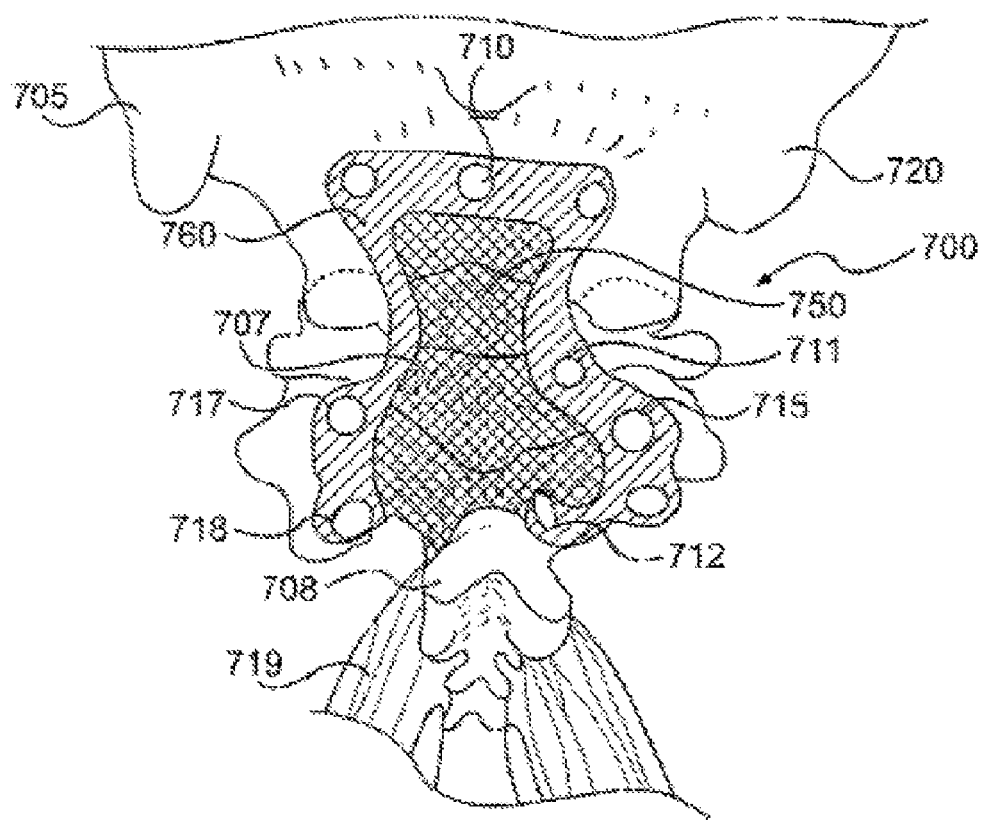
FIG. 30(a) shows an exemplary embodiment of the osteointegration apparatus oriented on the subocciput, C1 vertebra and C2 vertebra.

As shown in the exemplary embodiment of FIG. 30(a), osteointegration apparatus 700 may include a porous member 750 and a frame member 760. The porous member 750, shown in FIGS. 30(a) and 31(a), may have any shape or configuration suitable for facilitating fixation and/or osteointegration. In an exemplary embodiment, the porous member may have a shape that at least partially or substantially conforms to a surface of a vertebra and/or cranium so as to facilitate attachment thereto. In the exemplary embodiment shown in FIG. 30(a)-31(b), which shows the position of osteointegration apparatus 700 relative to a patient's brainstem 701, spinal cord 702, cinus 703, opisthion 704, suboccipital cranium 705, anterior tubercle of the C1 vertebra 706, posterior arch of the C1 vertebra 707, spinous process of the C2 vertebra 708, odontoid process of the C2 vertebra 713, C3 vertebra 714, bifid spinous process with muscular attachments of the C2 vertebra 719, superior nuchal line 720, vertebral artery 723 and C2 vertebral body 724, porous member 750 may at least partially contact and abut a bone surface to facilitate osteointegration. Preferably, the porous member 750 may substantially contact and conform to one or more bone surfaces along a substantial length of the porous member 750. Porous member 750 may further include a plurality of perforations sized to allow for and encourages in-growth and through-growth of blood vessels and other mesenchymal tissues. The perforations may be either uniform or may have different sizes and shapes. In an exemplary embodiment, the perforations having a small diameter of about 200 to about 1000 microns, more preferably about 400 to about 600 microns, and most preferably about 500 microns, to enhance osteointegration. In an exemplary embodiment, the porous member 750 may have a tensile strength, hardness and thickness of about to facilitate bone fusion In the region of the surface over the host fusion surface, the porous mesh may preferably have a tensile strength of about 100 to about 5000 psi, or more preferably about 200 to about 3000 psi, closer to the range of cancellous bone; in the external surface of the porous mesh where more structural strength is needed, a tensile strength of about 10,000 to about 25,000 psi, and a yield strength of about 14,500 psi similar that of cortical bone may be preferable.

The porous member 750 may be synthesized from any suitable biocompatible material. In an exemplary embodiment, the material may include an adhesive component to facilitate bonding of the porous body with the surrounding tissues, including bone and/or soft tissue. The material may also include an osteogenesis and/or osteointegration compound to encourage fusion. The material may be substantially bioresorbable so as to be biologically incorporated into the host bone structures. The material may be composed of a polymethacrylate polymer that can be premolded or molded at the time of the stabilization procedure. The poly compound, such as polymethylmethacrylate may have other compounds mixed in to facilitate attachment, antibiosis or porosity. In an exemplary embodiment, the porous member may be any porous osseomeric mesh, a mesh of trabecular pattern that resembles the trabecular, or cancellous bone or other biocompatible material having a structure similar to cancellous (or trabecular) bone. The porous material could be fabricated from metal, such as metallic alloys of titanium or tantalum, carbon-composite, stainless steel, cobalt-chromium, ceramic, or biological materials such as coralline hydroxyapatite, cancellous bone or processed cortical bone. Alternatively, or in addition, the porous member 750 may be coated with an adhesive and/or osteogenesis material or chemical to facilitate attachment and osteointegration. Exemplary coatings may include osteoconductive coating includes, bone morphogenic proteins, hydroxyapatite, tissue in-growth and on-growth facilitating proteins, or glycoprotein's, or compounds or alloys of titanium, tantalum, carbon, calcium phosphate, zirconium, niobium or hafnium.

As shown in the exemplary embodiment of FIG. 30(a), osteointegration apparatus 700 may further include one or more frame members 760 that reinforces and strengthen porous member 750. The frame member 760 may be either internal or external to the porous member 750 to enhance structural rigidity or strength and may have any shape or configuration suitable for use in securely anchoring the osteointegration apparatus 700. In an exemplary embodiment, one or more portions of the frame member 760 may conform to the shape of one or more tissue surfaces. For example, a frame member 760 may conform to the shape and contours of one or more vertebrae.

Figure 31A:
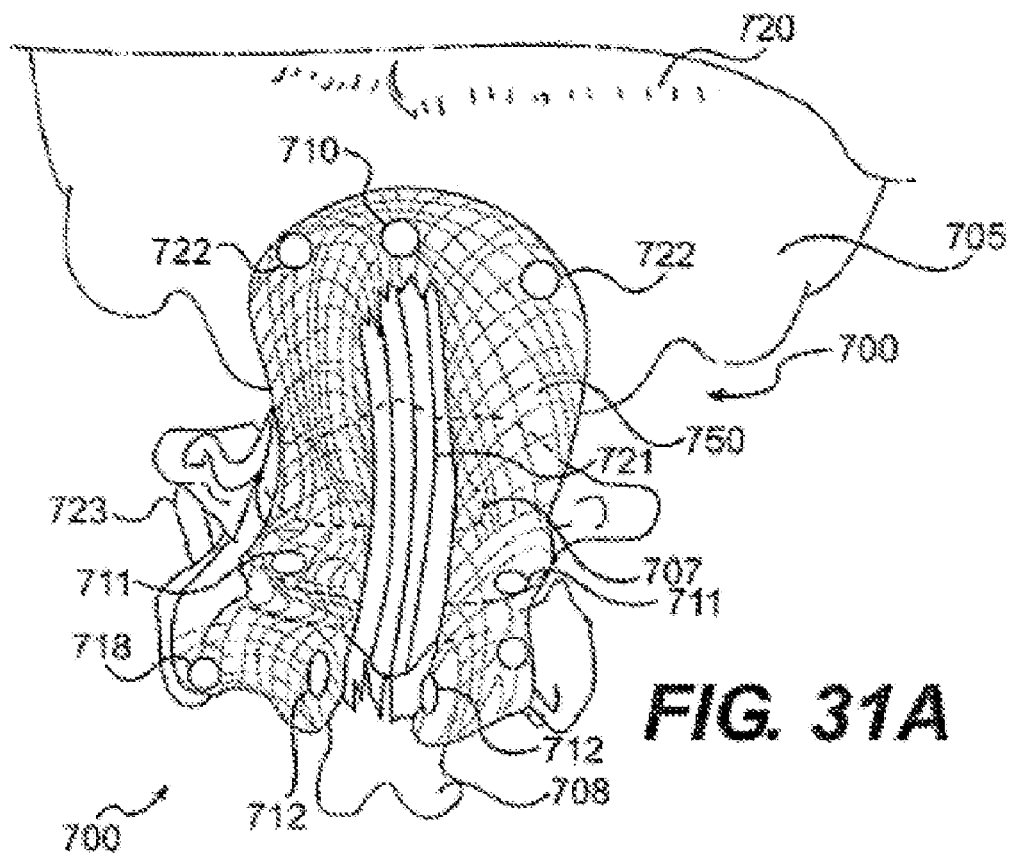
FIG. 31(*a*) shows another exemplary embodiment of the osteointegration apparatus oriented on the subocciput, C1 vertebra and C2 vertebra with a bone graft material oriented on the midline fold of device.

One or more frame member 760 may be uniformly or randomly positioned throughout the body of the porous member 750, including along a perimeter of, over the entire surface of (as shown in FIG. 31(a)), part of the surface of or throughout the central region of the porous member 750. In the exemplary embodiment of FIG. 30(a), the frame member 760 may be positioned along a portion of the perimeter of porous member 750. Specifically, frame member 760 may be a continuous unitary structure is substantially positioned along the entire perimeter of the porous body 750. Alternatively, a plurality of separate frame members 760 may be arranged substantially along the perimeter of the porous member 750 body. Multiple frame members 760 may be arranged in any formation that would be conducive to facilitating structural reinforcement and attachment of the porous member 750. In another embodiment, one or more frame members 760 may be interspersed within porous member 750 so as to create a reinforcing web. In this embodiment, the frame member 760 may be constructed from structurally enhanced filaments that are woven into the porous member 750 body. The reinforcing web may be interwoven, superficial or added upon as a modular component.

The frame member 760 may be fabricated from any suitable high strength biocompatible material that provides added support and reinforcement to porous member 750 and osteointegration apparatus 700. In an exemplary embodiment, the frame member 760 may be fabricated from titanium, carbon fiber, or a combination thereof. The material may be substantially bioresorbable so as to be biologically incorporated into the host bone structures.

Figure 32:
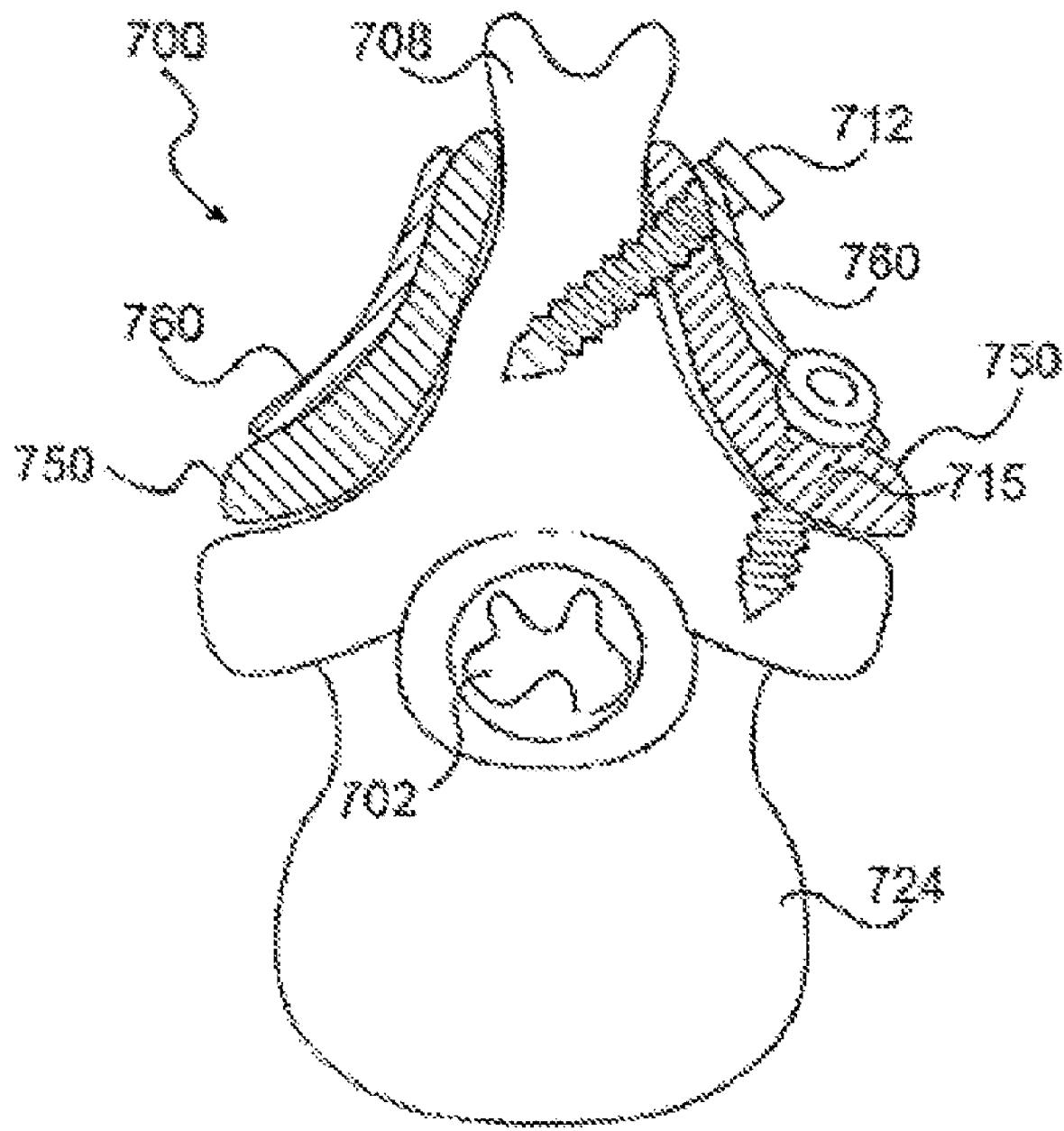
FIG. 32 is a cross-section an exemplary embodiment of the osteointegration apparatus attached through C2 spinous process and C2 lateral mass.
Figure 33A:
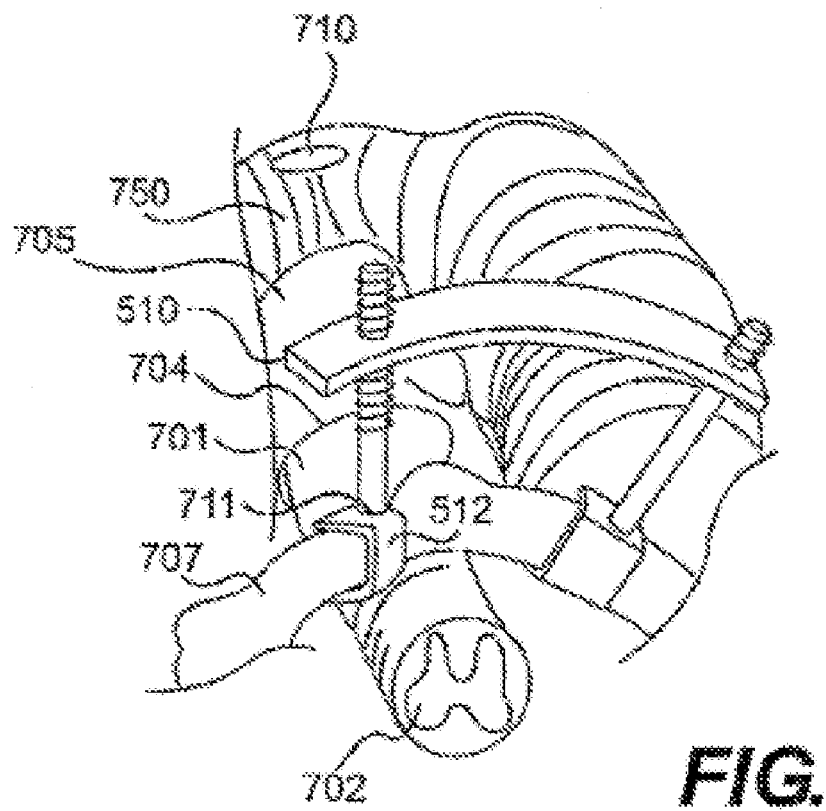
FIG. 33(*a*) is a fragmentary perspective of the C1 vertebral attachment system showing a fastener penetrating a trabecular mesh porous body and the C1 posterior arch.
Figure 33B:
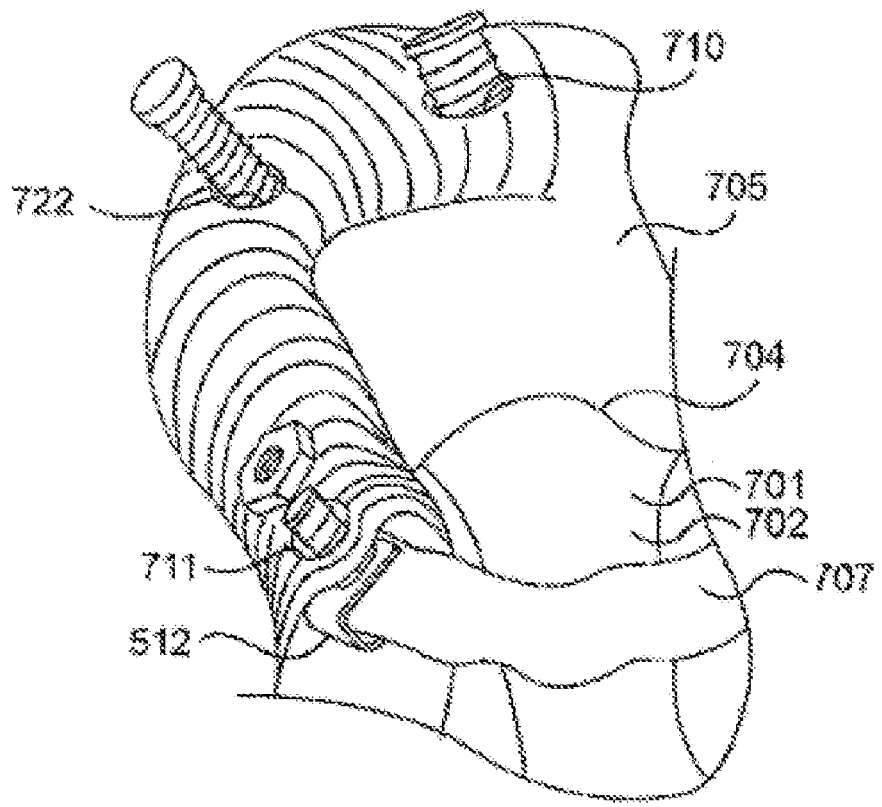

One or more portions of the porous member 750 and/or frame member 760 may support or may be coated with an osteogenic bone graft material 721 to facilitate bone fusion. Exemplary osteogenic material 721 may include, without limitation, autograft, allograft, xenograft, demineralized bone, malleable, cohesive, shape-retaining putty including mineral particles, insoluble collagen fibers and soluble collagen, hone cement, polymethylmethacrylate, (PMMA), calcium phosphate (CaP), demineralized bone matrix (DBM), bi-calcium phosphate matrix, platelet gel, bone sialoprotein morphogenetic protein (BMP) in a carrier matrix, patented recombinant human protein, calcium phosphate-based materials, methomathactuloid, cranial plast, calcium-sulfate, or combination thereof, synthetic and natural bone graft substitutes, such as bio-ceramics and polymers, and osteo-inductive factors. In an exemplary embodiment, osteogenic material 721 may include a bone morphogenetic protein (BMP), transforming growth factor β1, insulin-like growth factor, platelet-derived growth factor, fibroblast growth factor, LIM mineralization protein (LMP), and combinations thereof or other therapeutic or infection resistant agents, separately or held within a suitable carrier material and also biological agents, fleeces containing osteoprogenitor cells derived from periosteum. This material may be applied to any surface of the osteointegration apparatus 700. As shown in FIGS. 32-33(b), it may be positioned between either a biologic tissue, such as a bone surface, or other component of spinal stabilization system 100 and the porous member 750 and/or frame member 750 of the osteointegration apparatus 700. Fasteners used to secure the osteointegration apparatus 700 to a biological tissue or spinal stabilization component 100 may apply a compressive force so that osteointegration apparatus 700 and/or osteogenic material 721 may be substantially pressed against a bone surface to facilitate osteointegration.

In addition to the porous osteointrative structure and adhesive properties of osteointegration apparatus 700, the apparatus may be further fixed to a biologic tissue, such as bone, and/or component of spinal stabilization system 100 with one or more apertures and fastener. As shown in FIG. 32, the fastener may be used to directly anchor an osteointegration to a portion of a vertebra. Alternatively, as shown in FIGS. 33(a)-33(b), the fasteners may anchor the osteointegration apparatus 700 to a spinal stabilization system 100 component, such as vertebral attachment system 500. The fastener may serve to simultaneously attach both osteointegration system 700 and one or more components of spinal stabilization system 100, such as a vertebral clamp or plate 200, to a vertebral body and/or portion of the cranium.

Figure 31B:
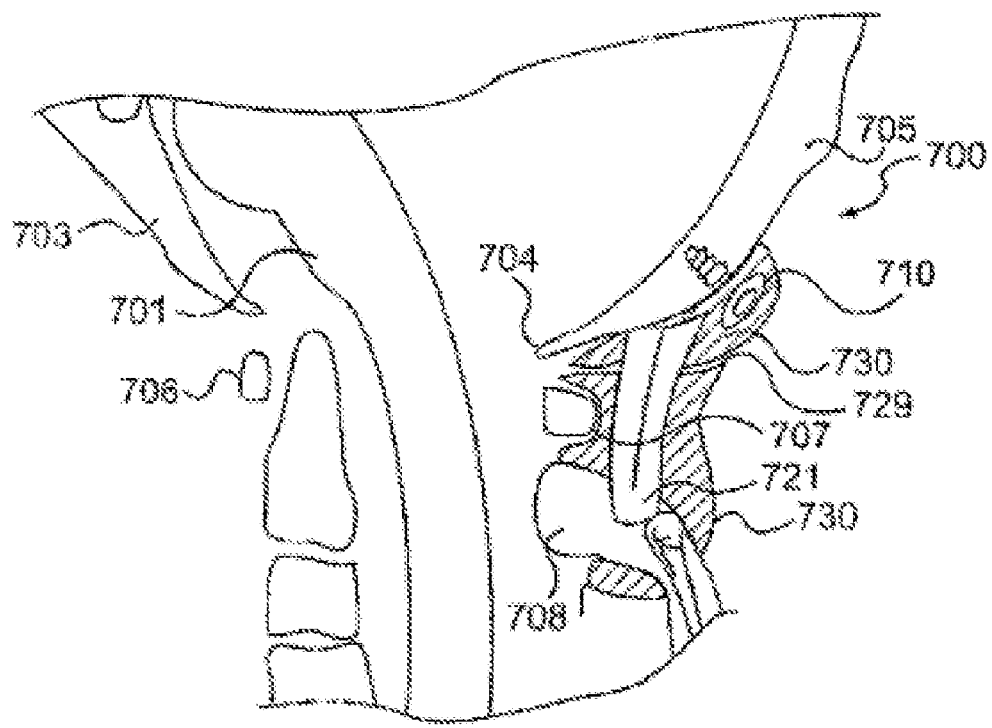

Porous member 750 and/or frame member 760 may include one or more apertures 780 for receiving a fastener. The apertures 780 may have different sizes and shapes and may be either placed along any surface of the frame member, porous member or a combination thereof. In an exemplary embodiment, the apertures may be reinforced with extra thickness to secure attachment and/or may be threaded, partially threaded or free from threads. The apertures 780 may be conventionally positioned to establish a secure attachment with bone. Exemplary locations may be in the subocciput, through the keel of the suboccipital bone, C1 ring, C1 or C2 pedicle, C2 lateral mass, a C2 spinous process or combinations thereof. As shown in the embodiment of FIGS. 31(a)-31(b), the osteointegration system 700 may include a central suboccipital aperture and fastener 710, a C1 vertebra aperture and fastener 711, a C2 spinous process aperture and fastener 712, a C2 lateral mass aperture and fastener 715, C2 pedicle aperture and fastener 717, a C2 transarticular aperture and fastener 718 and lateral suboccipital aperture and fastener 722. In one embodiment, the aperture may be a transarticular screw hole that passes through a vertebral pedicle. The location of the apertures and fastener may also be selected to avoid compressing sensitive regions of the anatomy, such as the vertebral artery 723, brainstem 701 or spinal cord 702, as well as avoid overlapping fastener placement, which may be accomplished by using a segmentation algorithm. A CT rendering may map and/or show the preordained placement of fasteners and/or other components of spinal stabilization system 100 on a patient's cranium and/or spine. For example, certain parts of the CT rendering of a pedicle would be registered and any overlying screw position may be identified.

The fastener may be any device capable of securing osteointegration apparatus 700 to a bone and/or portion of spinal stabilization system 100, such as a threaded component, hook, latch, pin, nail, wire, tether, or combinations thereof. Preferably, the fastener may be a threaded component such as a screw, bolt, rivet or nut. In an exemplary embodiment, the fastener may have a shallow penetration depth to prevent inadvertent injury to the vertebral artery, spinal cord or nerve roots which may induce a cerebrospinal fluid leak. Alternatively, osteointegration apparatus 700 may also include depth penetrating fastener to enhance fixation. In this embodiment, apertures may be specifically designated and positioned for receiving depth penetrating fasteners in order to minimize the risk of injury to the vertebral artery, spinal cord or nerve roots.

In a preferred embodiment, osteointegration apparatus 700 may substantially conform to the patient's anatomy and/or to implanted devices, such as spinal stabilization system 100. To accomplish this, in one exemplary embodiment, osteointegration apparatus 700 may be a preformed custom constructed from a 3D image of a CT rendering. For example, one or more portions of the osteointegration apparatus 700 may be designed to conform to the anatomy of the subocciput, C1 and the C2 laminae, as shown in FIGS. 30(a)-31(a), based on a pre-operative digitalized computer generated rendering of a patient's anatomy, to ensure fixation. The osteointegration apparatus 700 may be personalized to create a custom fit having no sharp edges.

Figure 30B:
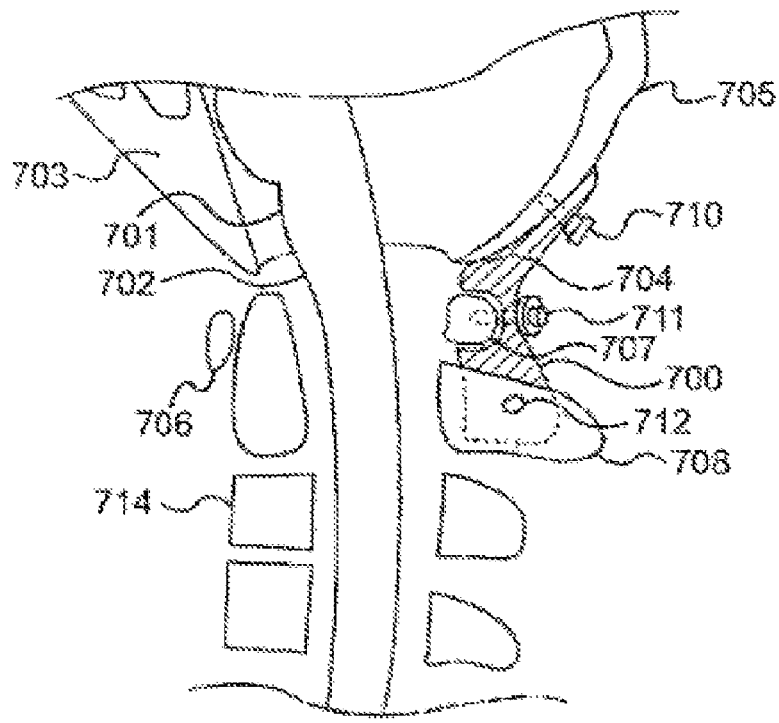
FIG. 30(b) is a cross-section of an exemplary embodiment of the osteointegration apparatus showing the device attached from the skull to C2.

In another exemplary embodiment, osteointegration apparatus 700 may be a modular preformed device capable of being manipulated to conform to a patient's anatomy. In one aspect, osteointegration apparatus 700 may be a flexible preformed structure that can be mechanically manipulated so as to change and/or retain a particular shape. The shape of osteointegration apparatus 700 may signal to the surgeon when appropriate normalization of bone relationship has occurred, and thereby when normalization of neurological architecture has occurred. That is, the osteointegration apparatus 700 will have various preformed geometries that require the normalization of the craniospinal angle. In an exemplary embodiment, an angle between the clivus and the posterior surface of the odontoid process (the clivo-axial angle) will have been manipulated to achieve approximately 165°, which is the normal angle for the population at large. Thus apparatus 700 may serve to identify in situ the correct clivo-axial angle, thus accomplishing a transformation of abnormal anatomy to normal anatomy. FIG. 30(b) shows the intrinsic angle between the cranial portion of the plate and the extensions onto the lower vertebral surfaces. A wide variety of angles, ranging from about 130° to about 170°, may encompass the full spectrum of abnormalities. The maximum correction of the clivo-axial angle is for most patients in the order of about 22°. Therefore a patient with a clivo-axial angle of about 110° could only be expected to undergo a correction to about 130°. In another aspect shown in the exemplary embodiment of FIG. 31(b), osteointegration apparatus 700 may be composed of one or more segments 730 that may be independently moveable relative to one another to facilitate modular reconstruction, adjustment, placement and/or anatomical conformation of osteointegration apparatus 700 to a patient's anatomy. These modular segments 730 may include porous members 750 and/or strong structural frame members 760. Each segment 730 may be separated from one another, for example as shown by gap 729 located between segments 730 in FIG. 31(*b*). Segments 730 may be entirely separate from, may cooperate with or may overlap with other segments 730 to facilitate fixation. In an exemplary embodiment, segments 730 may be hinge together to facilitate achievement of conformality. For example, osteointegration system 700 may have a plurality of porous members 750 that are independent moveable relative to one another but each individually hinged to a continuous frame member 760. In an exemplary embodiment, the porous/trabecular mesh structure may be soft enough ventrally or may contain slits in the porous body to better conform to contours of a bone. Additionally, each section may be either rigid or may be flexible so as to be mechanically manipulated during surgery to conform to a patient's anatomy. To facilitate fusion, the patient's anatomy may further be modified by sculpting to conform to the contours of the osteointegration apparatus 700. This ability to create an osteointegration structure that substantially conforms to a patient's anatomy may confer stability and strength to spinal stabilization system 100.

Method for Spinal Stabilization

A method for achieving occipitocervical fusion according to a preferred embodiment of the invention will now be described. The method of the present invention may be used to enable stabilization and/or fusion of the junction between one or more vertebrae and/or the occipitocervical junction of humans as well as animals. Specifically, the invention may be used to enable spinal or occipitocervical instability due to trauma or chronic spinal conditions, such as degenerative spinal diseases, metabolic spinal diseases, congenital spinal diseases, endocrinological spinal diseases, neoplastic or infectious spinal diseases, or cancer. Examples of chronic spinal conditions which may be treated in part using the vertebra attachment system of the present invention include degenerative diseases, such as systemic lupus erythematosis and rheumatoid arthritis, and metabolic conditions, such as osteomalacia, osteogenesis imperfecta, hyperparathyroidism, Ricket's Disease and Hurler's Disease; which cause basilar invagination. Other examples of conditions which may be assisted with the present invention may include congenital conditions, such as Down's syndrome and Morquio's Syndrome or miscellaneous conditions, such as Chiari Malformation, assimilation of the atlas, Klippel-Feil syndrome, condylus tertius, hypochordal bow, dystopic odontoideum, which may cause compression of the upper spinal cord or brainstem. The method for spinal stabilization may involve: pre-operatively scanning the region of the spine to be fused, manufacturing a customized osteointegration apparatus 700, surgically fusing the spine by connecting one or more vertebral attachment systems and/or cranial plates and implanting the osteointegration apparatus 700.

During the pre-operative scanning procedure, a patient may be positioned on a computed tomographic scanning table. In an exemplary embodiment, the patient's spinal alignment and/or deformity may be corrected or otherwise mitigated pre-operatively by manipulating the cranium and/or spine using non-surgical methods. When correcting a deformity of the occipitocervical junction, the patient's head is extended and the neuraxial and/or clivo-axial angle may then be normalized by applying gentle traction, extension of the cranium on the cervical spine, and/or posterior translation. The patient's head, neck and/or torso may be retained in this corrected position with a brace, such as a neck brace, that may be molded to conform to the patient's correctly positioned anatomy to accomplish closed reduction of deformity. Optionally, a radiographic image of the region to be stabilized may be obtained to confirm that the spinal alignment and/or deformity was corrected.

Subsequently, this anatomical region of the spine may be imaged using a computerized tomographic (CT) scan, which may produce thin image slices of about 1 mm. The images may be subsequently downloaded in any suitable electronic format, such as DICOM, and sent to a manufacturer to create a customized osteointegration apparatus 700 based on the anatomic specifications of the scanned images. In an exemplary embodiment, the osteointegration apparatus 700 may be a 3-dimensional form-fitting trabecular mesh designed to lay over the region of spinal fixation during surgery.

In an alternative embodiment a patient's the skull and spine may be sculpted to conform to a standard preformed osteointegration apparatus 700 intraoperatively. During surgery, the patient's anatomy may be sculpted to conform to the shape of the preformed osteointegration apparatus 700. Subtle changes in the host anatomy may be sculpted to conform to the device, and the device in turn may be capable of being manipulated or shaped to conform to the patient's anatomy.

The patient may then be intubated and prepared for surgery by immobilizing the cranium and/or torso. The patient may be first positioned prone with a Mayfield pin headrest in an appropriate sterile surgical environment. The posterior cranium (subocciput) will then be surgically exposed.

The suboccipital bone will then preferably be lightly drilled or sculpted in order to create a flat and even surface for the positioning of the plate 300. The plate 300 will then be aligned with the long axis of the patient's body and will be positioned symmetrically about the midline axis, so that the central screw hole 340 is preferably bisected by the midline axis of the patient's cranium as viewed in rear elevation. The center of the central screw hole 340 will then be marked on the cranium, and the plate 300 will be removed.

A central hole will then be surgically drilled in the cranium, preferably to a depth of 5-10 mm. using a high speed drill, then by a conventional surgical hand drill to complete the drilling, preferably to a total depth of between about 8 mm to about 12 mm. The screw hole will be tapped to a depth that is about 1 mm. longer than the screw to be used. (For example, for a 10 mm screw, tap to 11 mm depth). The plate 300 will then be repositioned on the midline.

The central hole may be obliquely angled and may be created by the previously discussed novel drill guide 800. For example, as shown in FIG. 3, the drill guide platform may be positioned on the occiput, approximately 3 cm above the opisthion. After positioning, drill guide 800 may be temporarily secured to the bone surface by taping its teeth into the bone with a tamp. Because drill guide 800 may include one or more angled drill bit receiving apertures and/or angled drill supports, a power drill may then be received by drill guide 800 to create an obliquely angled holes. Consequently, a greater screw length is inserted in the bone than would be had the aperture been oriented perpendicular to the bone surface, thereby enhancing fixation and screw purchase strength. This enhanced fixation therefore obviates the need for bone struts, structural bone, bone matrix or other bone substitutes for ensuring secure fastener attachment. The drill guide 800 may be used to create obliquely angled holes for receiving any fasteners of spinal stabilization system 100. Consequently, drill guide 800 may be used to position and orient various components of spinal stabilization system 100, including plate 300, flange 325 and/or vertebral attachment system.

The central cortical screw 42 will then be inserted into the tapped hole and tightened, lagging down the plate 300 to achieve solid fixation.

When there exists a cranial defect, such as wherein a substantial amount of bone that has been removed as a result of an occipital craniotomy, plate 300 and/or flange 24 may be positioned over and preferably cover the cranial defect. In an alternative embodiment, triple screw 70 or cranial attachment system 900 may be used to engage plate 300, flange 24, osteointegration apparatus 700, support rods 450, 452 or combinations thereof, wherein multiple cranial clamps 912 may be positioned around the perimeter of the craniotomy defect. In one embodiment, cranial clamps 912 may be positioned substantially equidistant relative to one another and/or symmetrically about the perimeter of the craniotomy defect, wherein at least one cranial fastener 922 directly engages a calvarial edge, clamp 912, plate 300 or flange 24, and a support rod. In an alternative embodiment, one or more clamps 912 and fasteners 922 are positioned along a perimeter of the cranial defect, wherein cranial fastener 922 directly attaches to support rod. Clamp 912 may be used to entirely replace plate 300, or plate 300 may be separately attached to the cranium over the cranial defect and cranial attachment system 900.

The method may involve exposing the posterior arch of the C1 and/or C2 vertebrae without injuring the vertebral vein or artery in the vertebral artery sulci. Before proceeding with the operation, the surgeon may check the CT or MRI to ensure that there is no stenosis at the level of the C1 vertebra.

The left C1 and C2 fastener assemblies 402, 406 will then be respectively inserted into the C1 and C2 vertebral bodies as is best shown in FIGS. 1 and 13.

The left pre-contoured support rod 450 is loosely positioned within the first clamping mechanism on 12 of the vertebral plate 550 and is secured to the left C1 and C2 fastener assemblies 402, 406.

The triple screw position for the first fastening assembly 462 that best aligns with the pre-contoured occipito-cervical rod 450 is then selected. The triple screw purchase selected is then drilled in the cranium. The lateral screw purchase may then be tapped if it is not been pre-threaded. The triple screw 70 is inserted.

The same operation is performed, again choosing the most appropriate position for the triple screw for the second fastening assembly 464.

The Mayfield headholder is then released, and an open reduction of the craniocervical junction is performed under fluoroscopy and under direct inspection. It is ensured that the abnormal angulation (kyphosis) of the craniospinal angle, and any abnormal translation of the skull is reduced, and that there is no rotation or lateral bending and no subluxation at lower spinal levels. The head-holder is then relocked.

The clivioaxial angle is then measured with the goal of achieving an optimal clivioaxial angle of about 150° to about 165°.

The support rods 450, 452 are then placed into the holes in triple screws 70 within the respective fastening assembly 462, 464 and the hex nuts 82 are placed over the screws 70 and tightened, as shown in FIGS. 8(a)-9(b).

The exposed suboccipital bone, the posterior ring of C1 and the lamina and facet joints of C2 are then surgically decorticated.

The first portions 216, 218 of the first and second bone forming material based structural member 212, 214 are then inserted into the graft accommodation space 332 that is defined between the plate 300 and the cranium, as is best shown in FIG. 2. The cephalad part of the bone forming material based structural member should be fashioned to fit precisely and under pressure beneath the flange 325 of the plate 300. In some embodiments, the caudal edge 326 of the plate 300 may now be bent down towards the cranium to further compress the graft. The caudal end of the graft should lie on the decorticated C1 and C2 (and lower levels where indicated) dorsal elements.

The graft loading vertebral plate is then positioned to hold down, under pressure, the portions of the first and second bone forming material based structural members 212, 214 that are positioned over and against the C1 and C2 dorsal elements using the vertebral attachment system 500 of FIGS. 14-15.

The fasteners 42 are then tightened and locked on the vertebral plate.

Demineralized bone matrix may then be applied to the fusion areas and more cancellous bone may be applied to complete the fusion. A layered wound closure is then performed conventionally over a drain.

Figure 34:
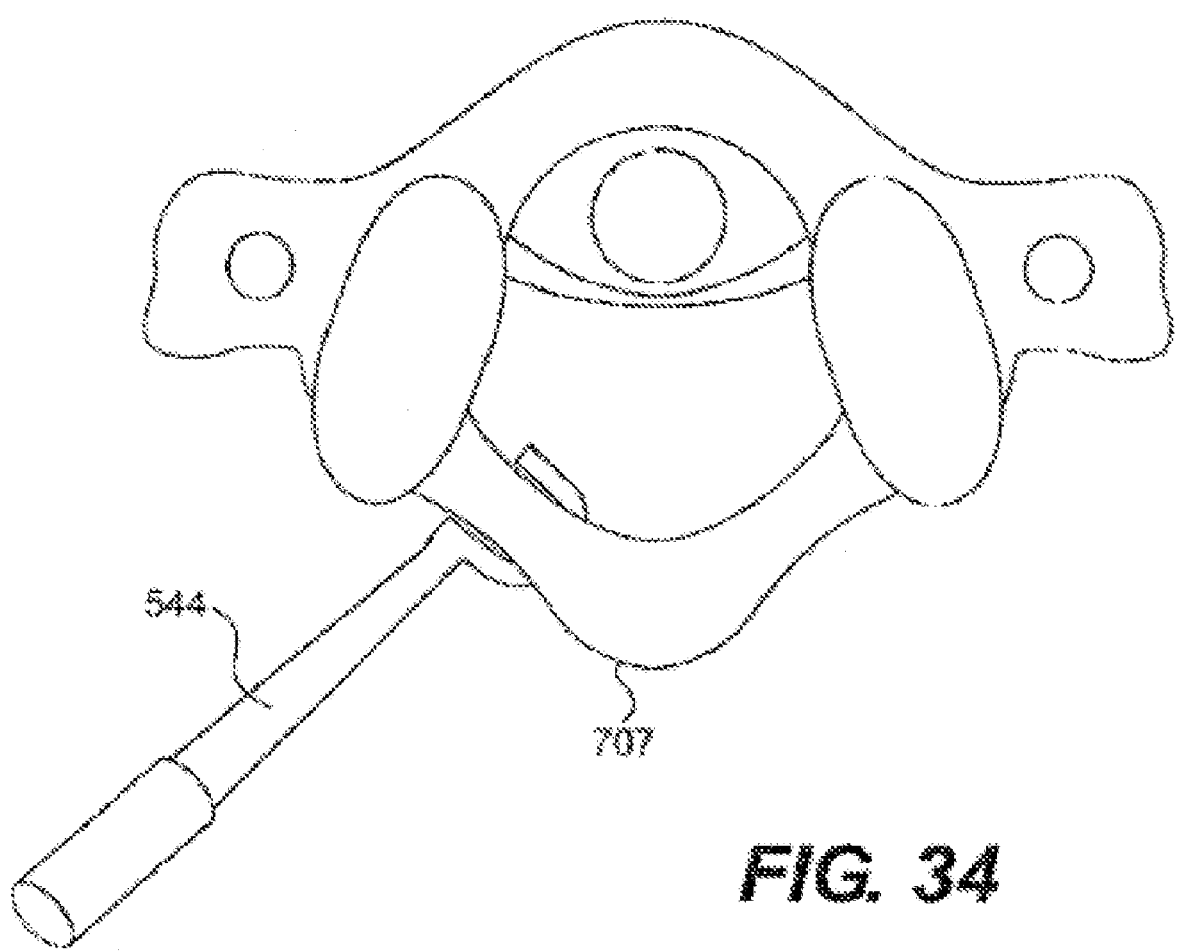
FIG. 34 shows an apparatus for testing trial clamps.

In another embodiment, a curved instrument 544, such as a curette, as shown in FIG. 34, may be used to open the plane ventral to the posterior arch. The same curved curette serves as a trial template for the vertebral clamp to be fitted around the posterior arch of a patient, in order to select the most appropriately sized vertebral clamp 512 for implantation. The selected vertebral clamp 512 may be inserted approximately 10-15 mm on one side of the midline of the posterior arch by friction fitting vertebral clamp 512 around a portion of the posterior arch. A second vertebral clamp 512 may be inserted approximately 10-15 mm on the opposite side of the midline. Optionally, a third vertebral clamp 512 may be placed at the midline of the posterior arch. In instances where only one vertebral clamp 512 is used to anchor vertebral plate 510 to a vertebra, vertebral clamp 512 may be inserted at the midline. Vertebral plate 510 may be inserted between the posterior vertebra and the vertebral clamps 512, as shown in FIG. 19, or placed above vertebral clamps 512, as shown in FIG. 17. One or more apertures 10 of vertebral plate 510 may then be aligned with one or more apertures 508 of vertebral clamp 512. Alternatively, one or more vertebral clamps 512 and vertebral plates 510 may be constructed as an integral device and fastened to a region that is safely distanced from the spinal cord, spinal nerve roots, vertebral artery and/or vertebral vein so as to avoid severing, compressing, impinging or otherwise injuring the these spinal components. In one embodiment the attachment system may be fastened to a posterior region, such as the posterior arch of the C1 vertebra, spinous process pedicle or lamina.

An osteogenic bone graft material 17, may be applied to the between vertebral attachment system 500 and a vertebra or portion of the cranium to facilitate bone fusion. In an exemplary embodiment, osteogenic material 17 may include, without limitation, autograft, allograft, xenograft, demineralized bone, synthetic and natural bone graft substitutes, such as bio-ceramics and polymers, and osteo-inductive factors. In an exemplary embodiment, osteogenic material 17 may include a bone morphogenetic protein (BMP), transforming growth factor β1, insulin-like growth factor, platelet-derived growth factor, fibroblast growth factor, LIM mineralization protein (LMP), and combinations thereof or other therapeutic or infection resistant agents, separately or held within a suitable carrier material. Additionally, osteogenic material 17 may also be applied partially along or completely cover any surface of vertebral clamp 512, fastener 522, vertebral plate 510, and/or any other orthopedic structure to which vertebral attachment system 500 is directly or indirectly connected to promote osteoblast generation and facilitate bone fusion. As shown in FIG. 22(c), bone graft material 517 may be placed above, below or on any surface of vertebral attachment system 500 as well as any corresponding orthopedic structure.

A transvertebral stabilization system 100 may be use to enhance spinal stabilization by anchoring a vertebral implant in a direction substantially orthogonal to the pull-out force. In particular, it is envisioned that the invention may be particularly useful where a C2 pedicle is too narrow to receive a screw or where an encroaching vertebral artery prohibits placement of a transarticular screw through the facet joint or a lateral mass. The transvertebral stabilization system 100 may be used in association with any stabilization system or vertebral implant to enhance stabilization and prevent loosening of vertebral implants and/or spinal stabilization systems 200.

In one embodiment, transvertebral stabilization system 100 may be implanted after fastener 616 is inserted into the vertebra, preferably through the lateral mass or on either side of the pedicle. Fasteners 616 of connector assemblies 602 may be located on various vertebra, establishing the frame work of spinal stabilization system 200. Connector 601 may then unilaterally or bilaterally inserted in fastener 616 of connector assembly 602. As shown in FIG. 26, connector 601 may fit into connector assemblies 602 bilaterally, to stabilize connector assemblies 602 transversely, and via the coupling devices, longitudinally and rotationally.

In an exemplary embodiment, connector 601 of transvertebral stabilization system 100 may penetrate a portion of the vertebral body, such as the spinous process, to secure the connector assembly 602 to the vertebra. For example connector 601 may be placed through the base of the spinous process, connecting and coupling the lateral mass fasteners 616 bilaterally, thus conferring enhanced stability. Penetration and passage through the vertebral body may be affected in a variety of ways. In one embodiment, cortex perforators may be used to align connector 601 relative to the connector assemblies 602 and create a through hole through the vertebral body. The blunt proximal end 606 of connector 601 may be inserted into slot 619 of connector assembly fastener 616, and the tapered distal end 605 of connector 601 may be inserted through the through hole of the vertebral body.

Figure 35:
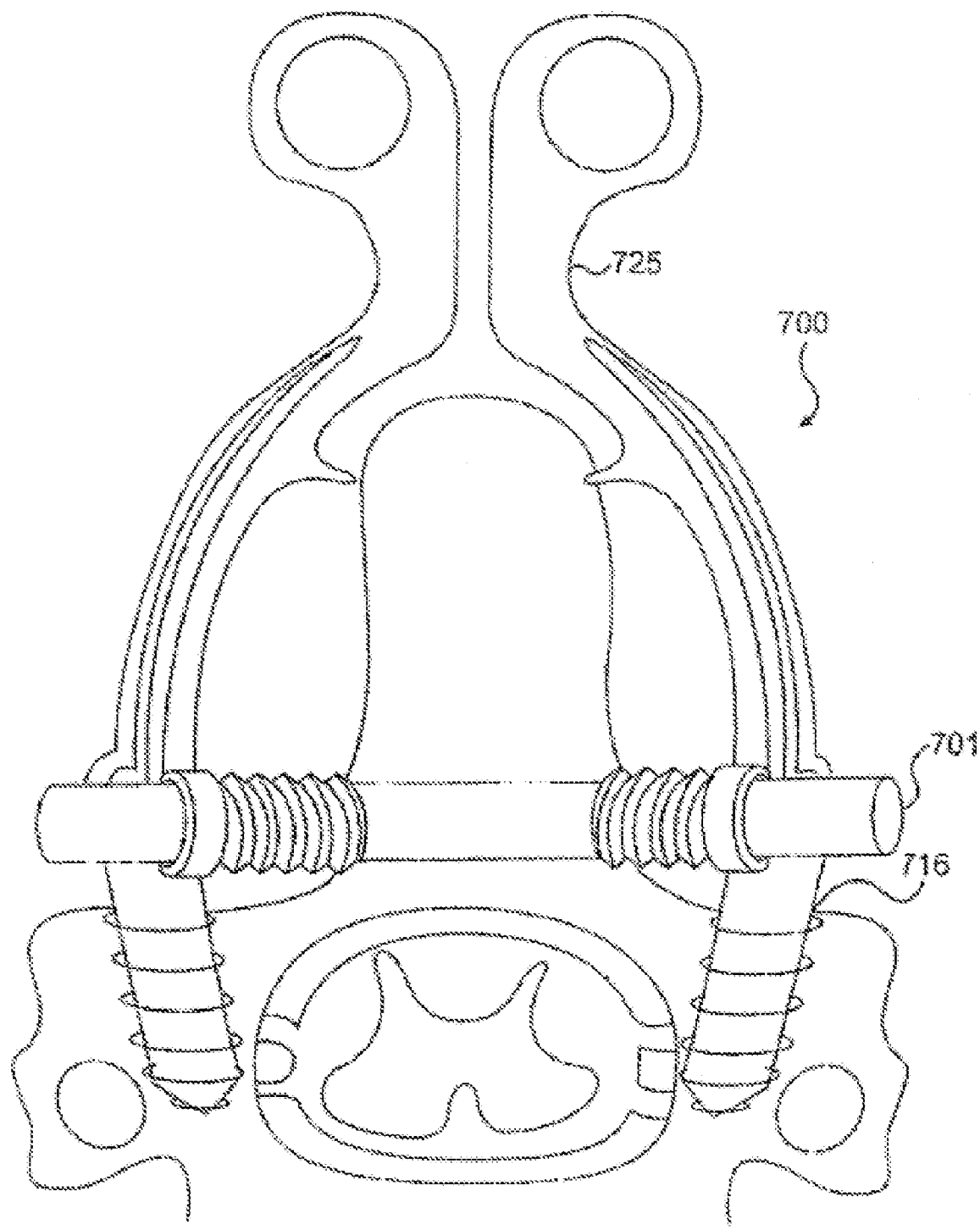
FIG. 35 shows a connector being guided with forceps.

In an alternative embodiment shown in FIG. 35, forceps 625, preferably a vice grip forcep, may be used to position and precisely align connector 601 relative to the connector assembly 602. The blunt proximal end 606 of the rod may be placed in the connector assembly fastened 616 to the lateral mass. The tapered distal end 605 of connector 601 may be forced into the perforated entry site of the spinous process by applying pressure to forcep 625. Forcep 625 may be used to guide and push the rod through the vertebral spinous process, as shown in FIG. 35.

In another exemplary embodiment, connector 601 having a sprocket 11 may be used to drill a hole through the vertebral body. A motor or other mechanical means may be used to drive a gearing mechanism 13, which in turn rotates connector 601. The rotating tapered threaded tip of the connector 601 consequently penetrates and drills a hole through the spinous process. In an exemplary embodiment, drilling may occur while connector 601 is supported and guided by vice grip forcep 625. Vice grip forcep 625 may be used to hold, direct and advance the shaft of connector 601 through the spinous process.

After connector 601 is bilaterally fastened to two connection assemblies 602, a top loading nut or screw may be tightened on each post 618 to secure connector 601. System connectors 617 may then be bilaterally coupled to connector 601 to complete the stabilization system. For instance, the system connectors 617 may be connected superiorly to the cranium and may engage connector 601 and/or connector assembly 602.

A method according to an alternative embodiment of the invention would utilize the integrated fixation member 142 that is depicted in FIG. 13. In this method, the preferred steps are preferably slightly reordered. First, placement of the screws into the lateral mass or ring or C1 and into the lateral mass or pedicle of C2, or into the lateral masses of the lower cervical or thoracic vertebrae would be performed.

Second the monolithic construct including the plate portion 380 and the integrated appendages 350, 352, which are surrogates for the rods 450 and 452 described with reference to the first embodiment of the invention, is applied over the screw heads.

Third, the craniospinal reduction is performed.

Fourth, the plate portion 380 is screwed to the skull with the central screw 42. The top loading nuts of fastening assemblies 406, 408 are then tightened down over the screw heads of the vertebral screws.

In all other respects, this method is identical to the method first described above.

The aforementioned spinal stabilization procedures may be minimally invasive only requiring a small surgical exposure. Specifically, the procedure need only expose the portion of the vertebrae and/or cranium to be attached to the spinal stabilization system. For example, the method for fusing the occipitocervical junction of the present invention only requires exposing the subocciput, C1 ring and C2 lamina. Incisions may be performed under fluoroscopic guidance to further minimize the surgical aperture. Additionally, neither implantation of the spinal stabilization device of the present invention nor implantation of the osteointegration apparatus 700 requires dissection of muscles away from the tip of the C2 spinous process. This minimizes the injury to the muscle attachments that hold up the neck. Vertebral attachment systems may be placed upon the posterior ring of the C1 vertebrae to anchor the C1 vertebra, obviating the necessity of inserting C1 lateral mass screws.

Prior to implanting the osteointegration apparatus 700, the patient may be positioned so as to normalize the angle of the skull base with respect to the spine. This may be accomplished by applying gentle traction, extension of the cranium on the cervical spine, posterior translation or any other mechanical manipulation of the anatomy of the patient. The osteointegration apparatus 700 may then orthotopically lowered onto the stabilized anatomical region and/or spinal fixation system. For methods involving the fixation of the occipitocervical junction, the osteointegration apparatus 700 may be laid over an exposed subocciput, C1 fixator screws and/or the prepared lamina of C2.

In an exemplary embodiment, an abrasive tool, such as a drill, may be used to sculpt a bone surface so as to create a more perfect union between the osteointegration apparatus 700 and anatomy of the patient. A sheet of pressure indicator-contact paper may be placed under the construct device to determine what areas or points of the osteointegration apparatus 700 are not conformal and what underlying bone may be removed or sculpted to create a substantially complete and/or continuous contact and conformality with the osteointegration apparatus 700.

When conformality is acceptable, portions of the cranium or spine may be decorticated to enhance osteointegration. For example, during occipitocervical stabilization, the suboccipital skull and the laminae of the first and second vertebrae may be decorticated with a high speed drill, to allow penetration of blood vessels into the osteointegration apparatus 700 and to provide a substrate rich in bone morphogenic protein (BMP) upon which to lay the osteointegration apparatus 700. The osteointegration apparatus 700 may be positioned over the spinal stabilization fasteners and may be fastened directly to one or more vertebrae, cranium and/or components of the spinal stabilization system. As shown in the exemplary embodiment of FIG. 30(*a*), the osteointegration apparatus 700 may be laid over the C1 screws and directly fastened to the C1 and/or C2 vertebra. Fasteners, such as screws, may also be placed through the osteointegration apparatus 700 into the subocciput to further enhance cranial fixation. Fasteners may also be positioned in the C2 lamina, lateral mass or spinous process. Optionally, fasteners may also be placed through the pedicle onto the body of C2 or through the lateral mass into the lateral mass of C1 in a C1-C2 transarticular technique.

It may be necessary to adjust the degree of extension by repeating open reduction of the craniospinal angle. Fluoroscopy may be used to confirm conformality, and adequate normalization of the neuraxial and/or clivo-axial angle. When there appears to be substantially complete contact between the osteointegration apparatus 700 and bone, locking elements, such as C1 lock nuts, may be tightened to more fully secure the osteointegration apparatus 700.

An autologous graft and/or allograft may be placed within the central region, i.e. cradle, of the osteointegration apparatus 700 facilitate fusion between the subocciput, C1 and C2. Exposed surfaces of the osteointegration apparatus 700 may also be covered in morsellised graft or graft substitute.

The incision may be closed over a drain in three to four layers, and a brace may surround the surgical region for about two to four weeks in order to allow for adhesion between the osteointegration apparatus 700 and surrounding tissue, thereby enabling spinal stabilization. Because the osteointegration apparatus 700 facilitates adhesion and osteointegration, the need for deeply penetrating screws is obviated.

Method for Treating a Neurological Disorder by Spinal Stabilization

The system and method for spinal stabilization of the present invention, specifically the system and method for stabilizing the occipitalcervical junction, may be used to treat neurological disorders that arise from abnormal biomechanical stress and strain of the brainstem. Without wishing to be bound by theory, abnormal biomechnically induced neuraxial stress and strain may contribute to or cause neurological disorders. Deformities at the level of the brainstem may cause pain, observed neurological deficit, and, over time, may altered neurological behavior. Specifically, bio-mechanically-induced stresses at the level of the brainstem may result in sleep disorders, abnormal gastroesophageal function (including GERDS), vision and reading difficulties, a multitude of behavioral disorders, of abnormal functioning of the autonomic nervous system, of scoliosis, abnormal gait and posture, and of abnormal urinary and sexual functioning. Without wishing to be bound by theory, stress due to biomechanical deformity, even in the absence of compression, may alter cell membrane physiology and may cause a change in neurological behavior. By mechanically normalizing the neuraxial stress and strain on the brainstem and upper spinal cord using spinal stabilization, it may be possible to treat the neurological disorder. Therefore, by stabilizing the occipitalcervical junction, it may be possible to correct abnormalities of the neuraxial angle and clivo-axial angle and thereby treat a neurological disorder. Without wishing to be bound by theory, neurological disorders may be genetically linked to or have a pathophysiological causation in relation to abnormalities of the neuraxial angle and clivo-axial angle. Therefore, it may be possible to treat one or more neurological disorders, such as positional orthostatic tachycardia, dizziness, head and neck pain, sensory disturbance, and bulbar findings, caused by hypermobility of the craniocervical junction induced by an abnormal clivo-axial angle, i.e. the angle between the clivus and the posterior axial line, such as a clivo-axial angle of less than about 140° in the cranial functional setting. In an exemplary embodiment, the invention may be used to treat a neurological disorder that underlies or otherwise contributes to a phenotypical feature or expression in patients diagnosed with any neurological disorder, including the exemplary neurological disorders described in present application, such as autism spectrum disorder.

Patients who have been diagnosed with or present symptoms associated with a neurological condition may be examined to determine whether abnormal brainstem compression or strain may be causing or contributing to their neurological symptoms. The present method for treating a neurological disorder may involve obtaining radiographic images of the occipitocervical junction, evaluating the neuraxial angle, neuraxial strain and/or neuraxial stress, determining the probability of whether a neuraxial deformation may be contributing to and/or causing the neurological disorder and treating the neurological disorder by stabilizing the occipitocervical junction, including reducing or correcting a neuraxial deformity, such as an abnormal neuraxial angle. A medical imaging computational device and/or computer readable software program may be used to determine the relationship between an abnormal neuraxial angle, abnormal clivo-axial angle, abnormal neuraxial stress and strain, and a neurological disorder.

The method for diagnosing and/or treating a neurological disorder may involve obtaining a radiographic image, such as an MRI, CT scan, CT with myelography, or x-rays of the occipitocervical junction. The calculation of biomechanically induced stress and strain may be accomplished by using dynamic radiographs or other imaging means to measure the degree of maximum stress, such as might occur in flexion of the craniospinal junction or flexion of adjacent bone members. In an exemplary embodiment, the radiographic image may clearly show the brainstem and/or spinal cord, as well as the anatomy of the skull base and upper spine at the occipitocervical junction. Preferably, a plurality of images showing the length and curvature of the brainstem and/or spinal cord from a variety of different perspectives, including a dorsal and ventral perspective, may be obtained. The most advantageous view for examining and determining the clivo-axial angle and neuraxial angle is the sagittal view of T2 weighted images in the neutral and flexed positions, centered at the craniospinal junction. Diffusion tensor imaging, cerebrospinal flow images, and spectroscopic MRI may also be of assistance in the determination of biomechanically induced pathophysiology.

These radiographic images may be captured by and/or transferred to a medical imaging computational device that supports, runs and/or is controlled by a computer readable software medium designed specifically to calculate or measure the neuraxial angle, clivo-axial angle, neuraxial stress, neuraxial strain, and combinations thereof, as well as determine the relationship of one or more of these properties with respect to a neurological disorder, specifically the probability as to whether the aforementioned properties either partially or substantially induce or contribute to a neurological disorder. In an exemplary embodiment, the medical imaging computational device and software medium may be programmed to identify and/or measure one or more aspects of one or more anatomical features of the captured images, including the occipitocervical junction, brainstem and/or spinal cord. The medical imaging computational device and software medium may be capable of calibrating the captured images so as to enable accurate measurements and/or calculations of various anatomical features. For example, it may be possible to measure the length of an outside perimeter, insider perimeter or midline of the brainstem and spinal cord as well as the width or thickness of multiple regions of the brainstem and spinal cord. The medical imaging computational device and software program may further be capable of comparing and/or mathematically manipulating these measurements to obtain meaningful calculations indicative and/or determinative of the presence of abnormal stresses and strains of the brainstem caused by anatomical deformities of the craniospinal junction that may in turn cause or contribute to a neurological disorder. In an exemplary embodiment, this may be accomplished by measuring the neuraxial angle to calculate the neuraxial stress and strain. In addition, measurements of the length of medulla and upper spinal cord on the ventral and dorsal surface (for the fourth ventral) may be taken. This allows the immediate calculation of stress and strain and thereby probability of altered conductivity and altered behavior. Without wishing to be bound by theory, the medullospinal angle of the neuraxis, i.e. neuraxial angle, accurately reflects the deleterious biomechanical stresses within the brainstem and upper spinal cord that may cause an alteration of gene expression, cell membrane physiology and neurological behavior. The medullospinal angle $\alpha$, also known as the neuraxial angle at the medullospinal junction, is that angle subtended at the epicenter of the arc of the medulla oblongata and spinal cord, centered at the craniospinal junction (defined by McRae's Line), and delimited superiorly by the pontomedullary junction, and inferiorly by a point in the spinal cord is equidistant from the center (McRae's Line) to the pontomedullary line (See FIG. 36). The medullospinal angle measures the loss of linearity of the brainstem and spinal cord, and is reflective of the subsequent stress and strain generated by the angulation of the neuraxis over the odontoid process at the craniospinal junction. The clivo-axial angle, which measures the angle between the dorsal aspect of the clivus and the dorsal aspect of the axis, i.e. C2 vertebra, is a surrogate measurement reflecting the concomitant angulation of the neuraxis resulting from abnormalities of the craniocervical junction, such as from basilar invagination. Secondarily, the medical imaging computational device and software program may also measure the clivo-axial angle to provide an estimate of the neuraxial stress and strain.

In an exemplary embodiment, the computer readable software medium and medical imaging computational device may be used to analyze the dynamic relationships of a patient's anatomy, including the angle between the bone members encasing the CNS, neuraxial angle, clivo-axial angle and/or neuraxial strain and stress. The neuraxial stress and strain may be caused by an abnormal neuraxial angle, abnormal flexion, ligament weakness, non-physiological movement, or any process that results in abnormal stretching of the neurons comprising the neuraxis. Without wishing to be bound by theory, amongst other biochemical changes, it is believed that neuraxial stress and strain may cause altered permeability of $Na^+$ and $Ca^{++}$ channels, loss of neuronal electro-negativity and subsequent loss of conductivity.

In an exemplary embodiment, the medical imaging computational device and software medium may be programmed to estimate or calculate neuraxial stress and strain using a number of different methods. Additionally, because strain and stress may occur simultaneously in multiple directions, neuraxial strain and stress may be analyzed in the x, y and z dimensions. In general, strain, $\epsilon$, is defined as a change in length divided by an original length, as expressed in equation 1.

$$\epsilon = \Delta L/L_0 \qquad \text{Equation 1}$$

Based on this formula, in one exemplary embodiment, it may be possible to calculate neuraxial strain by measuring the increase in neuraxial angulation that occurs in the presence of a skull based deformity, especially during flexion of the neck. Specifically, the method may involve calculating the increased length of the brainstem (medulla oblongata) as compared to the normal position within the base of the skull.

Figure 36:
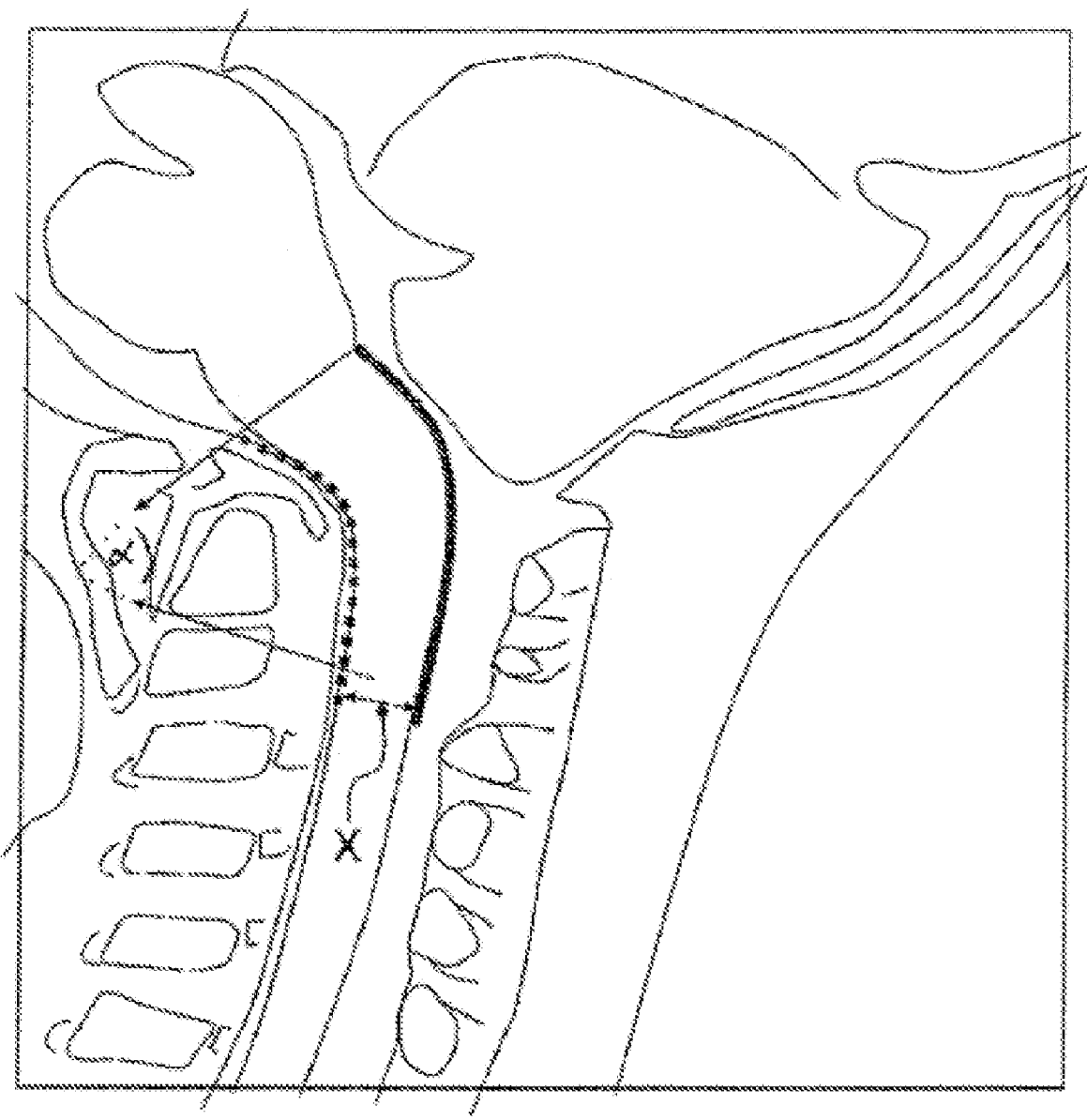
FIG. 36 shows an anatomical cross-sectional image of a brainstem.

According to this method, assuming that the brainstem and spinal cord subtends a neuraxial angle, $\alpha$, as shown in FIG. 36, which is subtended at the epicenter, then the length, l, of the dorsal columns will increase in flexion by virtue of the increased radius, r. That is, the dorsal columns, lying more distally from the epicenter are x cm more distant from the epicenter than the anterior surface (the black line) from the epi-center, and therefore, the dorsal columns are longer by the ratio of $2\pi(r+x)/2\pi r$ $$= r+x/r \qquad \text{Equation 2}$$

Applying the increased length of the dorsal columns/original length, the strain c that develops with a medullary kink is given by:

$$\epsilon = (r+x/r)/r \qquad \text{Equation 3}$$

Where r is the radius of the arc subtended by the curve caused by the kyphosis of the brainstem, and where x approximates the thickness of the spinal cord (about 1 cm) or brainstem (about 1.8 cm).

Given that the medullary curve occurs both in the brainstem (about 2 cm in length) and the upper spinal cord (about 2 cm in length), then the inner surface of the curved arc is about 4 cm. An arc subtending an angle of about 57° would have a radius, therefore, equal to the length of the arc, or about 4 cm. Therefore, for a uniform length of the neuraxis, the radius is given by, $$r = \alpha(\text{in degrees})/57° \cdot 4 \text{ cm} \qquad \text{Equation 4}$$

and the strain is therefore given by, $$\delta\epsilon = [(\alpha/57 \cdot 4 \text{ cm}) + x/(\alpha/57 \cdot 4 \text{ cm})]/[\alpha(\text{in degrees})/57° \cdot 4 \text{ cm}] \qquad \text{Equation 5}$$

Neuraxial stress may be subsequently determined based on the calculated strain value or may also be independently determined.

Generally, the angle between the skull base ventral and contiguous to the brainstem and the spine ventral and contiguous to the upper spinal cord is normally in the range of 165°+/−10° depending upon whether the neck is flexed or extended. A neuraxial angle and/or clivo-axial angle of less than 135° may indicate the likelihood of deleterious stresses in the CNS; a computer readable software medium and medical imaging computational device may consequently prompt a recommendation to normalize the relationship between the concatenated bone encasing elements and stabilizing these elements so as to normalize the stresses of the CNS.

In another exemplary embodiment, neuraxial strain may be calculated without measuring the neuraxial angle. A simpler means of estimating the change in neuraxial strain may involve analyzing the relationship between an inside curvature of the brainstem, i.e. the inner ventral surface of the brainstem, and a longer outer curvature of the brainstem, i.e. outer dorsal surface of the brainstem.

As shown in the exemplary embodiment of FIG. 36, the dotted line represents a line of best fit through the ventral aspect of the brainstem/spinal cord, i.e. neuraxis, and approximates the both the ventral and dorsal length of the neuraxis before deformation. The solid line of FIG. 36 that runs substantially parallel to dotted line represents a line of best fit over the elongated dorsal aspect of the neuraxis. An approximation of neuraxial strain may be calculated by dividing the difference in the length of these lines by the length of the dotted best fit ventral line.

Figure 37:
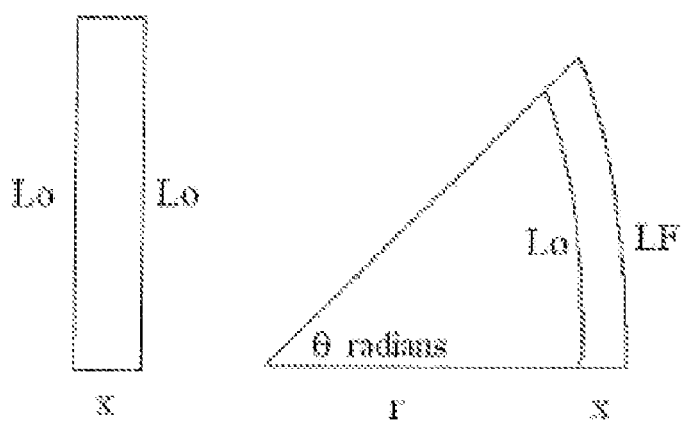
FIG. 37 is a calculation demonstrating that strain may be expressed as the thickness of the neuraxis divided by the length of the radius of the arc subtended by the angle σ over the deformity.

In a third exemplary embodiment, neuraxial strain can be calculated from the thickness of the neuraxis. Referring to FIG. 37, LF represents the length of the dorsum of the neuraxis after stretching over a deformity, x represents the thickness of the neuraxis at the region of the deformity, and r represents the length of the radius from the center of the arc of rotation of the neuraxis to the ventral surface of the neuraxis, subtended by the angle σ radians. Since the arc $L_O$, subtended by one radian, is equal in length of the radius r, strain c may be equal to the thickness of the neuraxis divided by the length of the radius of the arc subtended by the angle σ over the deformity, as shown in Equation 6.

$$\epsilon = x/r \quad \text{Equation 6}$$

With abnormal angulation of the neuraxis (medullospinal kyphosis), radius r becomes smaller and the thickness of the neuraxis at the apex of deformity becomes the dominant variable in assessing the strain across the dorsal half of the neuraxis.

This expression of neuraxial strain may be used to determine the electro-conductivity of a system. In general, the relationship of strain and electro-conductivity is non-linear. In the pathological range of strain, (that is, approximately $\epsilon=0.17$-$0.21$) conductivity, C, decreases with increased strain in an exponential fashion. That is, the change, δ, of C is inversely proportional to the exponential of the change, δ, of strain c. The new expression can be inserted into the expression for neuronal conduction amplitude, and other derivative equations, to reflect alteration of conduction amplitude. It is therefore possible to determine the relationship between strain and a change in neurological physiology. In a subset of patients, neurological physiology will be related to behavior. That is to say, neurological function and behavior, at least in a subset of patients, is a function of the deformative stress across the neuraxis.

Experimental data demonstrates that neuronal conduction amplitude is related to strain. Allowing 100% conductance at zero strain, and zero conduction at excessive strains (ε of >about 0.3), then conduction amplitude C can be shown to satisfy a quadratic expression that can be most simply expressed in this format, thus:

$$C = 1 - k \cdot \varepsilon^2 \quad \text{Equation 7}$$
$$= 1 - k \cdot (x/r)^2 \quad \text{Equation 8}$$

where ε is the strain of the neuraxis, x is the thickness of the neuraxis at the point of maximum deformation, r is the length of the radius to the arc of the ventral aspect of the neuraxis (See FIG. 37), and where k is a constant for a particular neuronal system that is algebraically related to the strain at which the particular neuronal system ceases to conduct an impulse. K may vary, namely increase, according to rapidity of strain (See FIG. 37), frequency of strain, modulus of elasticity of the neuraxial tissue, the ambient cerebrospinal fluid pressure, and will vary up or down according to the ionic state of the bathing fluid (CSF), and many other factors.

Many other polynomial expressions could be used to more closely represent the conduction amplitude for given conditions.

Figure 38:
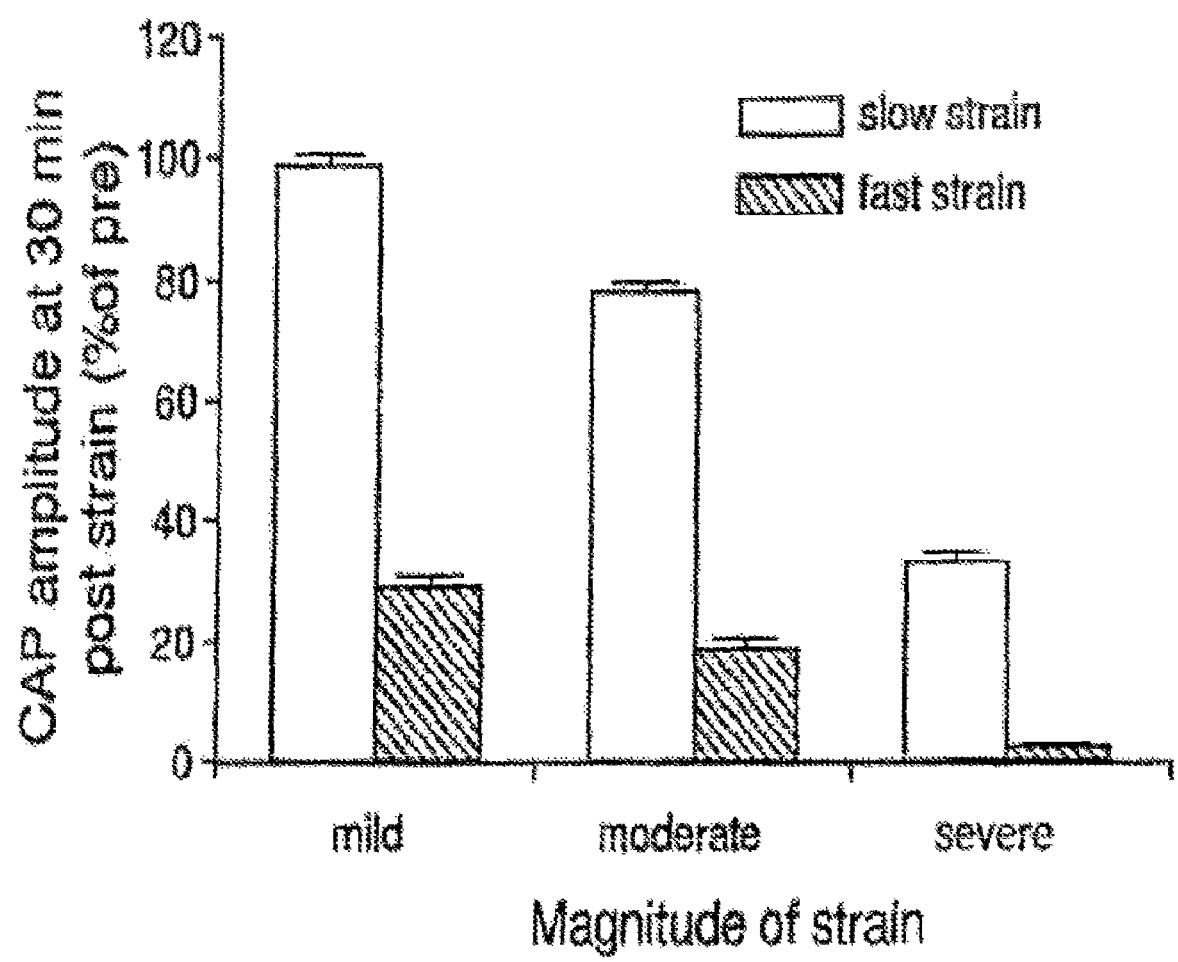
FIG. 38 is a graph of conduction amplitude as a function of strain.

In FIG. 38, animal research has shown that conduction amplitude decreases with magnitude of strain, and that amplitude decreases to a greater degree with the speed at which the strain is applied.

Without wishing to be bound by theory, it is believed that some behavioral changes may be related to abnormal conductional amplitude of specific neural tracts within the brainstem and spinal cord (neuraxis). The probability of abnormal behavior, Φ, relates inversely to the decrement in conduction amplitude, such that as conduction amplitude decreases, the probability of abnormal behavior increases. The following algorithms may be used to calculate this probability of abnormal neurological behavior as a function of conduction and neuraxial strain.

$$\Phi = f(C)^{-1} \quad \text{Equation 9}$$

An aggregate of abnormal conduction amplitudes within various neuronal tracts can be related to behavior change Φ, expressed thus:

$$\Phi = (f\Sigma^n(C)/n)^{-1} \quad \text{Equation 10}$$

where n is the number of the various pertinent neural fiber tracts inherent in any behavior. For instance, articulation of speech involves the nucleus ambiguous fibers, fibers to the hypoglossal nucleus and ponto-cerebellar fibers.

Substituting the equivalent expression for conduction amplitude, then the overall behavior change will be a function of various conduction amplitudes across the pertinent nerve tracts or groupings:

$$\Phi = f\Sigma^n(1-k \cdot \epsilon^2) \quad \text{Equation 11}$$

where k is a constant for a given nerve environment, relating to the strain ε at which conduction amplitude approaches zero, and n is a series of pertinent neural tracts.

Altered neuronal function (hence neurological behavior) is a function of the aggregate of strain, rate of strain, anatomically specific conduction decrement and time. The behavior change Φ will relate to the rate of decay of conduction amplitudes.

Therefore, $$\Phi = \left\{ f \sum^n (1 - k\varepsilon^2) \right\} \cdot f(t) \}^{-1} \quad \text{Equation 12}$$

$$= 1 \Big/ \left\{ f \sum^n [1 - k(x/r)^2] \right\} \cdot f(t) \quad \text{Equation 13}$$

where x is the distance between the pertinent fiber tract and the ventral surface of the neuraxis. For instance, x for a fiber tract in the midsection of the neuraxis, is equal to half of the width of the neuraxis, whereas a nerve tract on the dorsum of the neuraxis would have a magnitude equal to the thickness of the neuraxis.

And where r is the radius to the arc drawn along the ventral surface of the neuraxis (FIG. 37). Now k is proportional to rate of strain application, such that k will increase directly with rate of strain of the neuraxis.

The formula is based on the supposition of a relationship between the probability of behavioral change and various factors, such as the aggregation of von Mises stress on composite nerve fibers, such as the deformative stress of the nerve fibers of the cortical spinal tract, dorsal spinal tract, dorsal column tract, autonomic function tract, and respiratory function tract. Without wishing to be bound by theory, neural conductivity is diminished by deformative stresses, and neurological dysfunction is related to abnormal stress inducing modulation of the brainstem and upper spinal. Additionally, the formulation above reflects only the effects of biomechanical stress on neurological behavior, and does not assume to convey the effects of the multitude of other factors, such as, but not limited to, disorders of embryology, metabolism and endocrinology, the effects of toxins, tumor or pharmacology, altered circulation, anatomy and trauma.

The aforementioned mathematical algorithms can be incorporated in a computer readable software medium or medical imaging computational device to measure neuraxial strain, neuraxial stress, and predict the probability of developing abnormal behavior, such as a neurological disorder, in a given subject. Specifically, in a population of subjects with pain, bulbar symptoms, myelopathy, and an abnormal clivo-axial angle, abnormal neuraxial angle, and/or abnormal neuraxial strain and stress, the computer readable software medium and/or medical imaging computational device may calculate a value, based on images of the patient's brainstem and spinal cord, that can be compared with tables of predetermined values to provide a relative probability of the subject expressing abnormal behavior as a result of the observed neuraxial deformation. The computer readable software medium and medical imaging computational device may also potentially be used as a useful diagnostic tool for neuroradiologists to determine whether a patient's existing neurological disorder may be attributed to or exacerbated by abnormal neuraxial deformation. In an exemplary embodiment, the software medium and medical imaging computational device may be used to: accurately measure various anatomical features of a patient, and analyze the dynamic relationships of a patient's anatomy, including: calculating the angle between the bone members encasing the CNS, neuraxial angle, clivo-axial angle and/or magnitude of neuraxial strain and stress, making a calculation as to where the physical stress due to biomechanical deformity should be lessened to alter gene expression and normalize cell membrane physiology to relieve the neurological deficit and concomitant alteration of behavior, determining the probability of whether the patient's neurological disorder may be substantially caused by or contributed to abnormal neuraxial deformation, recommending a course of treatment to correct the neuraxial deformation, including specifying the angle of correction necessary to rectify the neuraxial deformation, providing visual displays showing the neuraxial deformation before and after a proposed corrective surgical procedure or any combination thereof. A surgeon may subsequently surgically correct the neuraxial deformation based on the information and calculations provided by the computer readable software medium and medical imaging computational device to correct to enable spinal stabilization and/or treat a neurological disorder. Specifically, the surgeon may stabilize craniospinal junction in a manner that normalizes the stresses of the CNS and returns to normal the cell membrane physiology and gene expression. The neuraxial deformation may be corrected using the spinal stabilization device of the present invention or any conventional spinal stabilization device. In an exemplary embodiment, the neuraxial deformation may be reduced by surgically correcting the clivo-axial angle such that is adjusted to about 145° to about 175°, more preferably about 150° to about 175°, and more preferably about 155° to about 175°, and most preferably, about 150° to about 170°.

In an exemplary embodiment, the computer readable medium and medical imaging computational device may computationally assess the strain or stress within the brainstem using an algorithm that determines the center line of the medulla, calculating the neuraxial angle, prompting surgical stabilization recommendations upon finding an abnormal neuraxial or clivo-axial angle, for example a clivo-axial angle of less than about 135°, computing the change in strain or stress that results from the abnormal neuraxial angle, associating the strain or stress with a probability of altered neurological function and/or behavioral change, recommend a surgical treatment means for stabilization of the craniospinal junction. In general, the method for treating neurological disorders may involve any combination of the any of the steps of any of the aforementioned embodiments.

Without wishing to be bound by theory, it is believed that particular neurological pheotypical behavior may be related to the particular neurons involved, the overall length of time of biomechanical neuronal deformity and the severity of deformity. Therefore, behavior phenotype is a function of the aggregate of anatomically specific neuronal dysfunction. The assessed or measured biomechanically induced stress across the CNS may mathematically relate in a non-linear manner to alteration of gene expression and cell membrane physiology. By correcting the aforementioned abnormal neuraxial strain and stress, the present invention may present a treatment for physical abnormalities resulting from changes in gene expression and altered cell membrane physiology, resulting in changes in neurological function and concomitant changes in behavior. Additionally, the stresses altering gene expression and membrane physiology may be maintained at a more normal level of functioning by the immobilization of the bone encasements around the CNS in a normal or close to normal relationship. By decreasing biomechanically induced stresses in the CNS, it may be possible to favorably alter neuronal gene expression and cell membrane physiology with the result that neurological function at the level of the brainstem and upper spinal cord may improve.

What is claimed is:

1. A cranial attachment device comprising:
    a clamp that is adapted to clamp around an edge of a cranial bone wherein the clamp constrains an inner surface of the cranial bone and an opposing outer surface of the cranial bone adjacent to the cranial bone edge, and wherein the clamp comprises:
        a first member having a surface conforming to the inner surface of the cranial bone, wherein said first member comprises a first hole;
        a second member having a surface conforming to the outer surface of said cranial bone, wherein said second member opposes and is spaced apart from said first member by a distance adapted for securely receiving the cranial bone; and
        a third member that encloses the edge of said cranial bone, wherein said third member is connected to said first and second members; and
    a fastener, wherein said fastener is positioned through said first hole and anchors said clamp to the cranial bone.

2. The device of claim 1, wherein said fastener comprises a second hole positioned through a width of the fastener, wherein said second hole is adapted to receive a spinal stabilization rod member.

3. The device of claim 2, wherein said fastener is a triple screw member comprising:
    a first portion comprising a first threaded surface for engaging cranial bone;
    a second portion for engaging said clamp;

a third portion comprising a second threaded surface; and
a nut member secured to said third portion, whereby said nut member may be tightened in order to secure a second surgical instrument.

4. The device of claim 2, wherein said second member comprises a second hole aligned with said first hole.

5. The device of claim 1, wherein the cranial attachment device further comprises a spinal rod that is integrally formed with an exterior surface of the third member such that the longitudinal axis of the spinal rod is substantially aligned with the longitudinal axis of the first and second members.

6. The device of claim 5, wherein the spinal rod has a bifurcated configuration and wherein two of the clamps are integrally formed on two distal ends of the bifurcated spinal rod, thereby lowering the profile of the cranial attachment device.

7. The device of claim 1, wherein the distance between the first and second member is about 5 mm to about 15 mm.

8. A spinal stabilization system comprising:
a rod member for use in spinal stabilization;
a cranial attachment device attached to the rod member, wherein the cranial attachment device comprises:
at least one clamp that is adapted to clamp around an edge of a cranial bone wherein the clamp constrains an inner surface of the cranial bone and an opposing outer surface of the cranial bone adjacent to the cranial bone edge, and wherein said clamp comprises:
a first member having a surface that conforms to and engages the inner surface of a cranial bone, wherein said first member comprises a first hole;
a second member having a surface that conforms to and engages the outer surface of said cranial bone, wherein said second member opposes and is spaced apart from said first member by a distance adapted for securely receiving the cranial bone; and
a third member that encloses the edge of said cranial bone, wherein said third member is connected to said first and second members; and
a fastener positioned through said first hole, wherein said fastener anchors said clamp to the cranial bone.

9. The system of claim 8, further comprising a plate positioned adjacent to the cranial clamp, wherein said fastener is positioned through a hole of said plate and attaches the plate to the cranial bone.

10. The system of claim 8, wherein the fastener is attached to said rod member and said clamp and wherein said fastener is a triple screw member comprising:
a first portion comprises a first threaded surface for engaging cranial bone;
a second portion inserted within said first hole;
a third portion comprising a second threaded surface; and
a nut member secured to said third portion, whereby said nut member may be tightened in order to secure a second surgical instrument.

11. The system of claim 8, wherein the system further comprises at least two or more of the clamps and wherein the two or more clamps are removably attached to the rod member to enable attachment at multiple points along a perimeter of a cranial defect.

12. The system of claim 8, wherein the rod member is integrally formed with an exterior surface of the third member such that the longitudinal axis of the spinal rod is substantially aligned with the longitudinal axis of the first and second members.

13. The system of claim 8, wherein the rod member has a bifurcated configuration and wherein the system comprises two or more of the clamps, and wherein at least one clamp is integrally formed on two distal ends of the bifurcated spinal rod, thereby lowering the profile of the spinal stabilization system.

14. A method for using a spinal stabilization system comprising:
attaching at least one clamp to a cranial bone so as to clamp around an edge of the cranial bone and constrain an inner surface of the cranial bone and an opposing outer surface of the cranial bone adjacent to the cranial bone edge, and wherein said clamp comprises:
a first member comprising a first hole;
a second member; and
a third member connected to said first and second members;
wherein the step of attaching said clamp to said cranial bone comprises:
positioning the cranial bone between the first and second members such that the first member contacts the inner surface of the cranial bone, the second member contacts the outer surface of the cranial bone and the third member encloses the edge of the cranial bone; and
inserting a fastener through said first hole and into said cranial bone.

15. The method of claim 14, further comprising the step of anchoring a first surgical instrument to said cranial bone by attaching said first surgical instrument to said fastener.

16. The method of claim 15, wherein said first surgical instrument is a rod member for enabling spinal stabilization, wherein said fastener comprises:
a second hole that passes through a width of said fastener and
a threaded region that engages with a nut for securing said rod member,
wherein said step of anchoring said first surgical instrument comprises inserting said rod member through said second hole and securing said rod member by tightening said nut relative to said threaded region.

17. The method of claim 15, further comprising the step of anchoring a second surgical instrument to said cranial bone by attaching said second surgical instrument with said fastener.

18. The method of claim 15, wherein the first surgical instrument is a rod member and wherein the exterior surface of the third member is integrally formed on a distal end of the rod member and wherein the method involves attaching the clamp to the edge of a cranial defect so as to lower the profile of the spinal stabilization system.

19. The method of claim 14, further comprising the step of positioning two or more of said clamps along an edge of a cranial defect.

20. The method of claim 19, further comprising the step of removably attaching and selectively positioning the at least two or more of the clamps along the rod member.

* * * * *